(12) United States Patent
Madar et al.

(10) Patent No.: US 11,471,222 B2
(45) Date of Patent: Oct. 18, 2022

(54) MODELLING A STRUCTURE IN A BODY

(71) Applicant: Navix International Limited, Tortola (VG)

(72) Inventors: Eyal Henri Madar, Haifa (IL); Shlomo Ben-Haim, Milan (IT); Yehuda Landau, Ramat-Gan (IL); Andrew Adler, Ottawa (CA); Oleg Kuybeda, Portland, OR (US)

(73) Assignee: Navix International Limited, Road Town (VG)

( * ) Notice: Subject to any disclaimer, the term of this patent is extended or adjusted under 35 U.S.C. 154(b) by 163 days.

(21) Appl. No.: 17/134,655

(22) Filed: Dec. 28, 2020

(65) Prior Publication Data

US 2021/0186625 A1  Jun. 24, 2021

Related U.S. Application Data

(60) Provisional application No. 63/047,298, filed on Jul. 2, 2020, provisional application No. 63/012,290, filed
(Continued)

(51) Int. Cl.
*A61B 34/20* (2016.01)
*A61B 5/053* (2021.01)
(Continued)

(52) U.S. Cl.
CPC .......... *A61B 34/20* (2016.02); *A61B 5/0044* (2013.01); *A61B 5/02028* (2013.01);
(Continued)

(58) Field of Classification Search
CPC ....... A61B 34/20; A61B 5/0538; A61B 90/37; A61B 5/053; A61B 5/0044;
(Continued)

(56) References Cited

U.S. PATENT DOCUMENTS

2005/0124908 A1   6/2005   Balalcazar et al.
2007/0270707 A1   11/2007  Balalcazar
(Continued)

FOREIGN PATENT DOCUMENTS

DE   8900090    3/1989
EP   3668393    6/2020
(Continued)

OTHER PUBLICATIONS

Kingma et al. "Adam: A Method for Stochastic Optimization", Computer Science;Conference Paper at the 3rd International Conference for Learning Representations, San Diego 2015, Machine Learning: 1-15, Published on Dec. 22, 2014.
(Continued)

*Primary Examiner* — Mark D Remaly

(57) ABSTRACT

Methods and systems of computing parameter values of one or more model parameters are described. The model models structural and dielectric properties of a structure in a human or an animal body. An exemplary method includes: accessing voltage measurements made at different places in the vicinity of the structure by one or more in-body field sensing electrodes in response to currents applied to one or more field supplying electrodes; and computing the parameter values by adjusting the parameter values to fit predicted voltage values to the accessed voltage measurements, wherein the predicted voltage values are predicted from the model for the currents applied to the field supplying in-body electrodes.

34 Claims, 16 Drawing Sheets

Related U.S. Application Data on Apr. 20, 2020, provisional application No. 62/953,224, filed on Dec. 24, 2019.

(51) Int. Cl.

| | |
|---|---|
| *A61B 5/00* | (2006.01) |
| *A61B 90/00* | (2016.01) |
| *A61B 5/02* | (2006.01) |
| *A61B 34/10* | (2016.01) |
| *G06F 3/14* | (2006.01) |
| *A61B 5/0522* | (2021.01) |

(52) U.S. Cl.
CPC ............ *A61B 5/053* (2013.01); *A61B 5/7203* (2013.01); *A61B 90/37* (2016.02); *A61B 5/0522* (2013.01); *A61B 2034/105* (2016.02); *A61B 2034/2053* (2016.02); *A61B 2505/05* (2013.01); *G06F 3/14* (2013.01)

(58) Field of Classification Search
CPC . A61B 5/02028; A61B 5/7203; A61B 5/0536; A61B 2034/105; A61B 2505/05; A61B 2034/2053; A61B 2017/00026; A61B 5/0522; A61B 2017/00053; G16H 50/50; G16H 20/40; G06F 3/14
See application file for complete search history.

(56) References Cited

U.S. PATENT DOCUMENTS

| | | | |
|---|---|---|---|
| 2008/0306359 A1 | 12/2008 | Zdeblick et al. | |
| 2010/0106154 A1 | 4/2010 | Harlev et al. | |
| 2010/0179421 A1* | 7/2010 | Tupin ..................... | A61B 5/05 600/426 |
| 2010/0286550 A1 | 11/2010 | Harlev et al. | |
| 2013/0172718 A1 | 7/2013 | Choi et al. | |
| 2014/0005512 A1 | 1/2014 | Manwaring et al. | |
| 2014/0039291 A1 | 2/2014 | Freeman et al. | |
| 2014/0107508 A1 | 4/2014 | Harlev et al. | |
| 2019/0365280 A1 | 12/2019 | Shmayahu et al. | |

FOREIGN PATENT DOCUMENTS

| | | |
|---|---|---|
| WO | WO 98/01069 | 1/1998 |
| WO | WO 03/063680 | 8/2003 |
| WO | WO 2006/012181 | 2/2006 |
| WO | WO 2008/097767 | 8/2008 |
| WO | WO 2010/129095 | 11/2010 |
| WO | WO 2014/022683 | 2/2014 |
| WO | WO 2014/054045 | 4/2014 |
| WO | WO 2018/092070 | 5/2018 |
| WO | WO 2019/035023 | 2/2019 |
| WO | WO 2020/008416 | 1/2020 |
| WO | WO 2020/212527 | 10/2020 |

OTHER PUBLICATIONS

International Search Report and the Written Opinion dated Oct. 28, 2019 From the International Searching Authority Re. Application No. PCT/IB2019/055731. (16 Pages).
Eng et al. "Evaluation of EIT Images Using Esophageal Electrodes", International Society for Electrical Bioimpedance & European Institute of Innovation & Technology, ICEBI & EIT 2016, Stockholm, Sweden, Jun. 20, 2016, Slide Show, 20 P., Jun. 20, 2016.
Jossinet et al. "Electrical Impedance Endotomography", Physics in Medicine and Biology, 47(13): 2189-2202, Published Online Jun. 20, 2002.
Jossinet et al. "Electrical Impedance Endo-Tomography: Imaging Tissue From Inside", IEEE Transactions on Medical Imaging, 21(6): 560-565, Jun. 2002.
Kwon et al. "A Local Region of Interest Imaging Method for Electrical Impedance Tomography With Internal Electrodes", Computational and Mathematical Methods in Medicine, 2013(Art.ID 964918): 1-9, Published Online Jul. 8, 2013.
Liu et al. "Minimally Invasive Electrical Impedance Tomography—Promising Way to Decrease Diagnostics Uncertainty", 2006 Proceedings of the 1st IEEE International Conference on Nano/Micro Engineered and Molecular Systems, Zhuhai, China, Jan. 18-21, 2006, p. 1250-1253, Jan. 18, 2006.
Martinsen et al. "Invasive Electrical Impedance Tomography for Blood Vessel Detection", The Open Biomedical Engineering Journal, 4: 135-137, Published Online Jul. 9, 2010.
Wan et al. "Incorporating A Biopsy Needle as An Electrode in Transrectal Electrical Impedance Imaging", 34th Annual International Conference of the IEEE EMBS, San Diego, CA, USA, Aug. 28-Sep. 1, 2012, p. 6220-6223, Aug. 28, 2012.

* cited by examiner

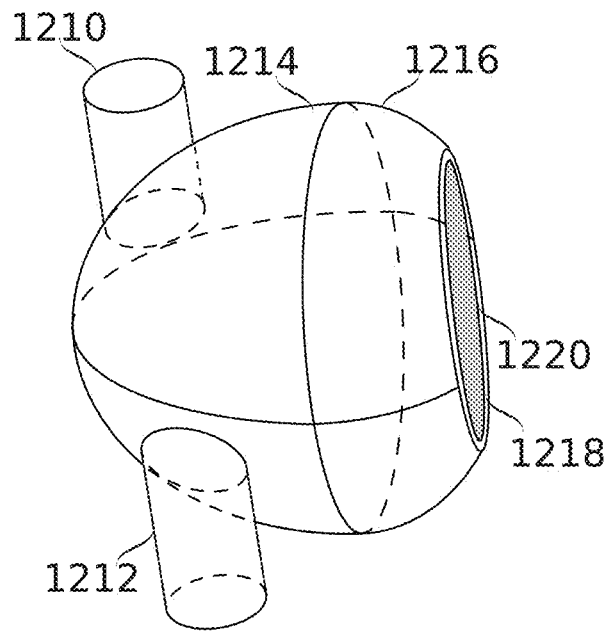
FIG. 1C
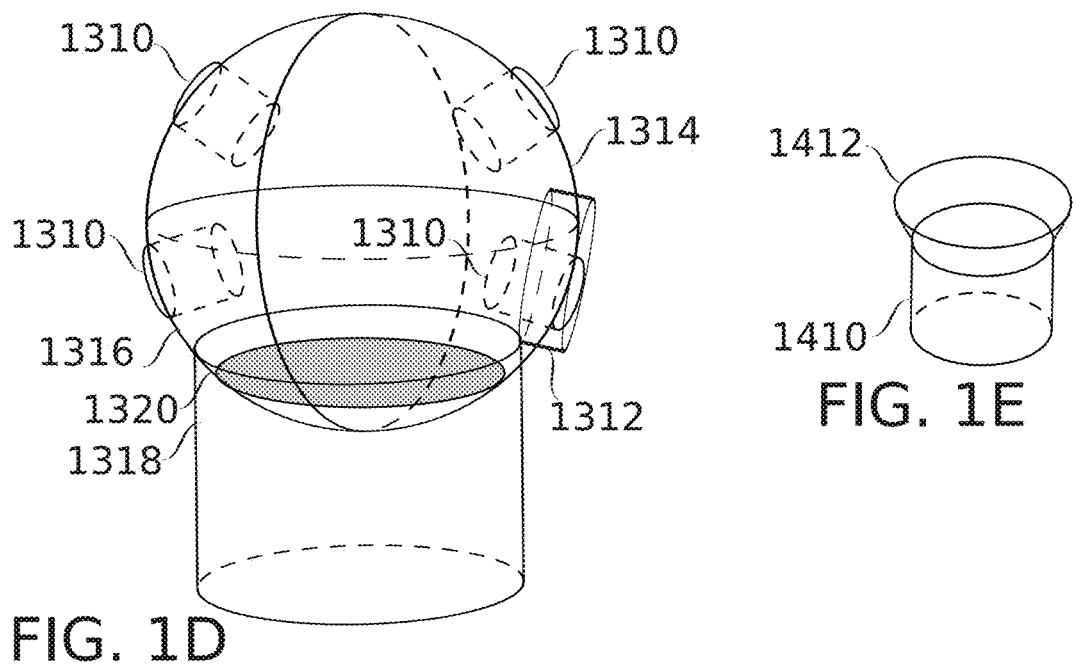
FIG. 1D
FIG. 1E

MODELLING A STRUCTURE IN A BODY

RELATED APPLICATIONS

This application claims the benefit of priority under 35 USC § 119(e) of U.S. Provisional Patent Application Nos. 63/047,298 filed on Jul. 2, 2020, 63/012,290 filed on Apr. 20, 2020 and 62/953,224 filed on Dec. 24, 2019, the contents of which are incorporated by reference as if fully set forth herein in their entirety.

FIELD AND BACKGROUND OF THE INVENTION

The present invention, in some embodiments thereof, relates to the field of anatomical imaging and more particularly, but not exclusively, to modelling of structures internal to a human or animal body.

Systems and methods for Electrical Impedance Tomography (EIT), as known in the art, involve injecting electrical currents at electrodes placed on the surface of a body and measuring, using other electrodes placed on the surface of the body, the potential (voltage), induced by the electric field supplied by the current injecting electrodes. From the measured voltages, 3D images or dielectric maps of tissues and organs inside the body can be generated based on the fact that different materials in the body (e.g. bone, fat, other tissue) have different dielectric properties.

It is also possible to generate images using electrodes placed inside the body, for example electrodes may be disposed on a catheter placed in a cavity in the body. In certain surgical procedures, it is also desirable to obtain information, such as the position, orientation, or other geometrical properties of a structure inside a body such as a catheter, surgical tool or implant.

SUMMARY OF THE INVENTION

According to an aspect of some embodiments of the present disclosure, there is provided a method of computing the shape of a structure within a human or animal body for real-time use in a medical procedure, the method including: accessing a model which models the structure as a spatially related collection of structural and dielectric properties, at least one of the properties being specified as at least one corresponding parameter; accessing location-associated voltage measurements made in the vicinity of the structure by one or more in-body field sensing electrodes: including a plurality of measurements for each sensing electrode at a corresponding plurality of associated locations, and wherein the measurements are responsive to currents applied to one or more field-supplying electrodes; and computing parameter values for the at least one parameter by adjusting the parameter values to fit predicted voltage values at model-defined locations to the accessed voltage measurements at their associated locations, wherein the predicted voltage values are predicted from the model for the currents applied to the field supplying electrodes; and provide the model with its parameter values for use in display, thereby providing an indication of the structural environment within which the location-associated voltage measurements were obtained.

According to some embodiments of the present disclosure, the model includes at least two parameters: one contributing only to the modeling of a first portion of the structure, and another contributing to the modeling of the first portion as well as an additional portion of the structure.

According to some embodiments of the present disclosure, the model includes at least two parameters: one contributing to modeling of a first portion of the structure and not a second portion of the structure, and the other contributing to modeling of the second portion, but not the first.

According to some embodiments of the present disclosure, the model includes at least two parameters: one contributing to the modeling of each portion of the structure, and one affecting only a sub-portion of the structure.

According to some embodiments of the present disclosure, the model includes at least three parameters: a first and a second parameter, each respectively contributing only to the modeling of first and second portions of the structure, respectively, and a third parameter, which contributes to the modeling of both the first and second portions.

According to some embodiments of the present disclosure, the model includes a first parameter which is associated to an error cost for some of its values; and wherein the adjusting takes the error cost into account.

According to some embodiments of the present disclosure, the model includes a first parameter and a second parameter, and a computable relationship between the first and second parameters is associated to an error cost for some of its values; and wherein the adjusting takes the error cost into account.

According to some embodiments of the present disclosure, parameters of the model define parameterized geometrical shapes assigned to a respective plurality of portions of the model, and the adjusting adjusts the geometrical shapes to approximate the positions of surfaces of the structure.

According to some embodiments of the present disclosure, the number of accessed voltage measurements used in the computing exceeds the number of parameters by a factor of at least three.

According to some embodiments of the present disclosure, the number of accessed voltage measurements used in the computing exceeds the number of parameters by a factor of at least ten.

According to some embodiments of the present disclosure, the number of parameters is below 500, and above 25.

According to some embodiments of the present disclosure, the number of parameters is below 100, and above 6.

According to some embodiments of the present disclosure, the method includes iteratively: accessing of the location-associated voltage measurements while new location-associated voltage measurements are being obtained; re-computing the parameter values using the new location-associated voltage measurements; and providing new versions of the model with its parameter values for use in display.

According to some embodiments of the present disclosure, the new location-associated voltage measurements are obtained from locations of the structure represented in a previous display of the model, but not among locations for which location-associated voltage measurements were previously available.

According to some embodiments of the present disclosure, the represented locations of the structure were, in the previous display of the model, at least 1 cm away from the closest locations for which location-associated voltage measurements were previously available.

According to some embodiments of the present disclosure, the at least one parameter includes one or more model parameters defining dielectric properties of the structure.

According to some embodiments of the present disclosure, the at least one parameter includes two or more parameters defining dielectric properties of respective different portions of the structure.

According to some embodiments of the present disclosure, the dielectric properties comprise dielectric properties corresponding to the tissue of one or more of: heart cardiac muscle, vascular wall, heart valve annulus, and heart valve leaflet.

According to some embodiments of the present disclosure, the one or more field supplying electrodes comprise a plurality field supplying electrodes, wherein the current applied to each field supplying electrode was at a different respective frequency such that each field supplying electrode supplied an electric field at the frequency of the respective applied current.

According to some embodiments of the present disclosure, when the voltages were measured, each of the one or more field sensing electrodes sensed voltages in response to each of the electric fields supplied at the different frequencies.

According to some embodiments of the present disclosure, the one or more field sensing electrodes were disposed on one or more tools positioned inside the body at the time that the accessed voltage measurements were measured, and configured to move within the body.

According to some embodiments of the present disclosure, when the accessed voltage measurements were measured, the at least one tool configured to move within the body was moving inside the body.

According to some embodiments of the present disclosure, the accessed voltage measurements comprise voltage measurements recorded at different times using the same one or more field sensing electrodes.

According to some embodiments of the present disclosure, at each of the different times at which voltage measurements were recorded, the one or more field sensing electrodes are disposed at different positions in the body.

According to some embodiments of the present disclosure, when the accessed voltage measurements were measured, voltage measurements were sampled at a sampling rate of between 300 kHz and 500 kHz.

According to some embodiments of the present disclosure, the method further includes performing signal processing on the voltage measurements and updating the voltage measurements at a rate of at least 100 times a second.

According to some embodiments of the present disclosure, when the accessed voltage measurements were measured, applied current measurements indicative of the currents applied to the one or more field supplying electrodes were sampled at a sampling rate of between 300 kHz and 500 kHz.

According to some embodiments of the present disclosure, the method further includes performing signal processing on the current measurements and updating the applied current data at a rate of at least 100 times a second.

According to some embodiments of the present disclosure, one of the at least one parameter corresponds to an orientation or a position of the modelled structure relative to the one or more tools.

According to some embodiments of the present disclosure, the at least one parameter include one or more position parameters corresponding to a position of the modelled structure, each position parameter corresponding to a position coordinate.

According to some embodiments of the present disclosure, the at least one parameter include one or more orientation parameters corresponding to an orientation of the modelled structure, each orientation parameter corresponding to an orientation coordinate.

According to some embodiments of the present disclosure, the structure is a surgical implement.

According to some embodiments of the present disclosure, the structure includes an internal tissue surface.

According to some embodiments of the present disclosure, structure is a wall of a body cavity, and wherein the tissue surface is an internal surface of the wall.

According to some embodiments of the present disclosure, the structure is a leaflet in a heart cavity and wherein the tissue surface is a surface of the leaflet.

According to some embodiments of the present disclosure, when the accessed voltage measurements were measured, the one or more field supplying electrodes and one or more field sensing electrodes were disposed within a cavity of a heart and on a tool and in a plane; and wherein the at least one parameter includes a parameter representing a distance between the tool and the internal tissue surface, and a parameter representing an angle between the plane of the electrodes and the internal tissue surface.

According to some embodiments of the present disclosure, the at least one parameter includes a parameter representing a distance between the tool and the internal tissue surface, and a parameter representing an angle between the plane of the electrodes and the internal tissue surface, and wherein the internal tissue surface is modelled as a plurality of planar surfaces, each surface having a respective model parameter representing a distance between the tool and the surface, and a respective model parameter representing an angle between the tool and the surface.

According to some embodiments of the present disclosure, the at least one parameter includes a parameter representing the thickness of the wall.

According to some embodiments of the present disclosure, the at least one parameter includes a parameter representing a dielectric property of the internal tissue surface.

According to some embodiments of the present disclosure, the at least one parameter includes a parameter representing a dielectric property of a material on the side of the wall outside of the body cavity.

According to some embodiments of the present disclosure, the method further includes identifying the material on the other side of the wall based on a computed value of the model parameter representing a dielectric property of a material on the other side of the wall.

According to some embodiments of the present disclosure, the method further includes identifying a specific portion of the wall of the cavity based on the computed values of the at least one parameter.

According to some embodiments of the present disclosure, the method further includes identifying the body cavity based on the computed values of the at least one parameter.

According to some embodiments of the present disclosure, the body cavity is a heart cavity, and identifying the specific body cavity includes identifying the heart cavity.

According to some embodiments of the present disclosure, computing the parameter values is performed in real-time as the accessed voltage measurements are measured.

According to some embodiments of the present disclosure, the parameter values are computed for each of a plurality of candidate models.

According to some embodiments of the present disclosure, each candidate model models the structure as a different respective candidate structure, and wherein each candidate structure is defined by a different respective set of at least one parameter.

According to an aspect of some embodiments of the present disclosure, there is provided a system for determining the values of one or more model parameters associated with a model of an object in a region of an organ of a human or animal body, the system including:

a processor configured to implement a method described above, a memory for storing the voltage measurements, the position data, the current data, and the values of the one or more model parameters.

According to some embodiments of the present disclosure, the system further includes: a plurality of electrodes disposed on one or more tools; an electric field generator configured to apply currents to the electrodes, and an electric field receiver configured to receive voltages measured at the electrodes.

According to an aspect of some embodiments of the present disclosure, there is provided a method of computing parameter values of one or more model parameters of a model, wherein the model models the structural and dielectric properties of a structure in a human or an animal body, the method including: accessing voltage measurements made at different places in the vicinity of the structure by one or more in-body field sensing electrodes in response to currents applied to one or more field supplying electrodes; and computing the parameter values by adjusting the parameter values to fit predicted voltage values to the accessed voltage measurements, wherein the predicted voltage values are predicted from the model for the currents applied to the field supplying in-body electrodes.

According to some embodiments of the present disclosure, the accessed voltage measurements are indicative of voltages sensed by the one or more field sensing electrodes in response to electric fields generated by currents applied to the one or more field supplying electrodes, wherein, when the accessed voltage measurements were measured, the one or more field supplying electrodes were disposed to supply an electric field that interacted with the structure and the one or more field sensing electrodes were disposed inside the body and positioned relative to the structure such that the field sensing electrodes were disposed to measure a voltage resulting from the electric field interacting with the structure.

According to some embodiments of the present disclosure, the method further includes: accessing current data indicative of the respective currents applied at the one or more field supplying electrodes when the accessed voltages were measured; and accessing position data indicative of positions of the field supplying and field sensing electrodes at the time the voltages were measured, wherein computing the parameter values includes computing the parameter values using the accessed voltage measurements, the current data, and the position data.

According to some embodiments of the present disclosure, the one or more model parameters comprise model parameters defining one of a shape, a size, a dimension, and an aspect of shape of the modelled structure.

According to some embodiments of the present disclosure, the one or more model parameters comprise model parameters defining one or more of a position and an orientation of the modelled structure.

According to some embodiments of the present disclosure, the one or more model parameters comprise two or more model parameters each defining one of: a shape, a size, a dimension, an aspect of shape, a position, or an orientation of respective different portions of the structure.

According to some embodiments of the present disclosure, the one or more model parameters comprise one or more model parameters defining dielectric properties of the structure.

According to some embodiments of the present disclosure, the one or more model parameters defining dielectric properties of the structure comprise two or more parameters defining dielectric properties of respective different portions of the structure.

According to some embodiments of the present disclosure, the one or more dielectric properties are one or more of: conductivity, complex conductivity, real or imaginary part of conductivity, permittivity, complex permittivity, real or imaginary part of permittivity, impedance, complex impedance, and real or imaginary part of impedance.

According to some embodiments of the present disclosure, computing the values of the one or more model parameters includes accessing starting values for each of the one or more model parameters, setting the one or more model parameter values to the respective starting values and repeatedly: computing predicted voltage values modelling the voltages measured at the field sensing electrodes using: the current data, the position data, and the model parameter values; computing an error signal indicative of an error between the predicted voltage values and the accessed voltage measurements; and adjusting the one or more model parameter values using the error signal.

According to some embodiments of the present disclosure, the number of parameters for which values are computed is fewer than the number of voltage measurements comprised within the accessed voltage measurements.

According to some embodiments of the present disclosure, the method according to any preceding further includes accessing dielectric data indicative of one or more dielectric properties of the modelled structure and fixing the values of one or more corresponding model parameters based on the dielectric data.

According to some embodiments of the present disclosure, computing the predicted voltage values, computing an error signal, and adjusting the one or more model parameter values are repeated until a stopping criterion is reached.

According to some embodiments of the present disclosure, the structure includes a plurality of portions and wherein, for each portion of the structure, the model includes one or more parameters defining structural properties of the portion.

According to some embodiments of the present disclosure, the structure includes a plurality of portions and wherein, for each portion of the structure, the model includes one or more parameters defining dielectric properties of the portion.

According to some embodiments of the present disclosure, the one or more field supplying electrodes comprise a plurality field supplying electrodes, wherein the current applied to each field supplying electrode was at a different respective frequency such that each field supplying electrode supplied an electric field at the frequency of the respective applied current.

According to some embodiments of the present disclosure, when the voltages were measured, each of the one or more field sensing electrodes sensed voltages in response to each of the electric fields supplied at the different frequencies.

According to some embodiments of the present disclosure, the one or more field sensing electrodes were disposed on one or more tools positioned inside the body at the time that the accessed voltage measurements were measured.

According to some embodiments of the present disclosure, at least one of the one or more tools disposed inside the body is a catheter.

According to some embodiments of the present disclosure, at least one of the one or more tools disposed inside the body is configured to move within the body.

According to some embodiments of the present disclosure, when the accessed voltage measurements were measured, the at least one tool configured to move within the body was moving inside the body.

According to some embodiments of the present disclosure, the accessed voltage measurements comprise voltage measurements recorded at different times using the same one or more field sensing electrodes.

According to some embodiments of the present disclosure, at each of the different times at which voltage measurements were recorded, the one or more field sensing electrodes are disposed at different positions in the body.

According to some embodiments of the present disclosure, when the accessed voltage measurements were measured, voltage measurements were sampled at a sampling rate of between 300 kHz and 500 kHz.

According to some embodiments of the present disclosure, the method further includes performing signal processing on the voltage measurements and updating the voltage measurements at a rate of at least 100 times a second.

According to some embodiments of the present disclosure, when the accessed voltage measurements were measured, applied current measurements indicative of the currents applied to the one or more field supplying electrodes were sampled at a sampling rate of between 300 kHz and 500 kHz.

According to some embodiments of the present disclosure, the method further includes performing signal processing on the current measurements and updating the applied current data at a rate of at least 100 times a second According to some embodiments of the present disclosure, one or more of the field supplying electrodes was disposed on a surface of the body at the time the measurement was obtained.

According to some embodiments of the present disclosure, one or more of the field supplying electrodes was disposed inside the body at the time the measurement was obtained.

According to some embodiments of the present disclosure, the one or more field supplying electrodes disposed inside the body was disposed on the one or more tools.

According to some embodiments of the present disclosure, one of the one or more model parameters corresponds to an orientation or a position of the modelled structure in a reference frame fixed relative to the body.

According to some embodiments of the present disclosure, one of the one or more model parameters corresponds to an orientation or a position of the modelled structure relative to the one or more tools.

According to some embodiments of the present disclosure, the one or more model parameters include one or more position parameters corresponding to a position of the modelled structure, each position parameter corresponding to a position coordinate.

According to some embodiments of the present disclosure, the one or more model parameters include one or more orientation parameters corresponding to an orientation of the modelled structure, each orientation parameter corresponding to an orientation coordinate.

According to some embodiments of the present disclosure, the structure includes a blood vessel or a portion of a blood vessel, wherein the blood vessel is modelled by the model of the structure as a cylinder, and wherein one of the one or more model parameters corresponds to a diameter of the cylinder.

According to some embodiments of the present disclosure, the dielectric data contains values of a dielectric property of the volume surrounding the blood vessel, and values of one or more dielectric properties of the volume inside the blood vessel.

According to some embodiments of the present disclosure, the one or more model parameters comprise: one or more model parameters defining a dielectric property of the volume inside the blood vessel; and one or more model parameters defining a dielectric property of the volume surrounding the blood vessel.

According to some embodiments of the present disclosure, at least one of the one or more tools was disposed inside the blood vessel.

According to some embodiments of the present disclosure, the structure is a surgical implement.

According to some embodiments of the present disclosure, the dielectric data contains values of a dielectric property of one or more portions of the surgical implement.

According to some embodiments of the present disclosure, the one or more model parameters comprise one or more model parameters each defining a dielectric property of a respective portion of the surgical implement.

According to some embodiments of the present disclosure, the surgical implement is an expanding implant and wherein one of the one or more model parameters corresponds to a degree of expansion of the modelled structure.

According to some embodiments of the present disclosure, a first model parameter corresponds to the degree of expansion of the modelled structure; a second model parameter corresponds to a position of the modelled structure, and a third model parameter corresponds to an orientation of the modelled structure.

According to some embodiments of the present disclosure, the second and third model parameters correspond to the position and orientation of the expanding implant relative to the body respectively.

According to some embodiments of the present disclosure, the second and third model parameters correspond to the position and orientation of the expanding implant relative to one of the one or more tools respectively.

According to some embodiments of the present disclosure, the structure includes an internal tissue surface.

According to some embodiments of the present disclosure, structure is a wall of a body cavity, and wherein the tissue surface is an internal surface of the wall.

According to some embodiments of the present disclosure, the structure is a leaflet in a heart cavity and wherein the tissue surface is a surface of the leaflet.

According to some embodiments of the present disclosure, when the accessed voltage measurements were measured, the one or more field supplying electrodes were disposed inside the cavity.

According to some embodiments of the present disclosure, when the accessed voltage measurements were measured, the one or more field supplying electrodes and one or more field sensing electrodes were disposed on a tool and in a plane, optionally wherein the tool is a Lasso catheter.

According to some embodiments of the present disclosure, when the accessed voltage measurements were measured, the tool was contacting the internal tissue surface.

According to some embodiments of the present disclosure, the one or more model parameters comprise a parameter representing a distance between the tool and the internal tissue surface, and a parameter representing an angle between the plane of the electrodes and the internal tissue surface.

According to some embodiments of the present disclosure, the internal tissue surface is modelled as a plurality of planar surfaces, each surface having a respective model parameter representing a distance between the catheter and the surface, and a respective model parameter representing an angle between the catheter and the surface.

According to some embodiments of the present disclosure, the internal tissue surface is modelled as a composite surface by combining the plurality of planar surfaces.

According to some embodiments of the present disclosure, the internal tissue surface is modelled as a planar surface.

According to some embodiments of the present disclosure, the internal tissue surface is modelled as a portion of a cylindrical surface.

According to some embodiments of the present disclosure, the internal tissue surface is modelled as a portion of a spherical surface.

According to some embodiments of the present disclosure, the one or more model parameters comprise a parameter representing the thickness of the wall.

According to some embodiments of the present disclosure, the one or more model parameters comprise a parameter representing a dielectric property of the internal tissue surface.

According to some embodiments of the present disclosure, the one or more model parameters comprise a parameter representing a dielectric property of a material on the side of the wall outside of the body cavity.

According to some embodiments of the present disclosure, the method further includes identifying the material on the other side of the wall based on a computed value of the model parameter representing a dielectric property of a material on the other side of the wall.

According to some embodiments of the present disclosure, the method further includes identifying a specific portion of the wall of the cavity based on the computed values of the one or more model parameters.

According to some embodiments of the present disclosure, the method according to claim 58 or further includes identifying the body cavity based on the computed values of the one or more model parameters.

According to some embodiments of the present disclosure, the body cavity is a heart cavity, and identifying the specific body cavity includes identifying the heart cavity According to some embodiments of the present disclosure, adjusting the one or more model parameter values includes adjusting to reduce a magnitude of the error signal.

According to some embodiments of the present disclosure, adjusting the one or more model parameter values to reduce a magnitude of the error signal includes determining new values for the one or more model parameters using an optimization process and the error signal and setting the one or more parameter values to the respective new values.

According to some embodiments of the present disclosure, the method further includes computing new predicted voltage values using the respective new values of the one or more parameter values.

According to some embodiments of the present disclosure, the optimization process is gradient descent process.

According to some embodiments of the present disclosure, the optimization process is an Adam optimization process.

According to some embodiments of the present disclosure, computing the parameter values is performed in real-time as the accessed voltage measurements are measured.

According to some embodiments of the present disclosure, the parameter values are computed for each of a plurality of candidate models.

According to some embodiments of the present disclosure, each candidate model models the structure as a different respective candidate structure, and wherein each candidate structure is defined by a different respective set of one or more model parameters.

According to an aspect of some embodiments of the present disclosure, there is provided a method according to claim 72 wherein computing the values of the sets of model parameters for each candidate model includes carrying out the method described above, for each candidate model.

According to some embodiments of the present disclosure, for each candidate model, computing predicted voltage values, computing an error signal, and adjusting the one or more model parameter values is repeated until a stopping criterion is reached.

According to some embodiments of the present disclosure, the method accordingly to further includes selecting one of the plurality of candidate models to model the structure based on the respective number of repetitions of: computing predicted voltage values; computing an error signal; and adjusting the one or more model parameter values, according to claim 10 that are required before the stopping criterion is reached.

According to some embodiments of the present disclosure, selecting one of the plurality of candidate models includes selecting the candidate model that requires the fewest number of repetitions before the stopping criterion is reached.

According to some embodiments of the present disclosure, the method further includes classifying the modelled structure based on the candidate structure of the selected candidate model.

According to some embodiments of the present disclosure, classifying includes determining a geometric property of the modelled structure based on a corresponding geometric property of the candidate structure.

According to an aspect of some embodiments of the present disclosure, there is provided a system for determining the values of one or more model parameters associated with a model of an object in a region of an organ of a human or animal body, the system including: a processor configured to implement a method according any preceding claim; and a memory for storing the voltage measurements, the position data, the current data, and the values of the one or more model parameters.

According to some embodiments of the present disclosure, the system further includes: a plurality of electrodes disposed on one or more tools; an electric field generator configured to apply currents to the electrodes, and an electric field receiver configured to receive voltages measured at the electrodes.

According to an aspect of some embodiments of the present disclosure, there is provided a non-transitory computer readable medium carrying instructions that, when executed by one or more processors, cause the processors to carry out a method described above, According to some embodiments of the present disclosure, the method further includes: applying currents to the one or more field supplying electrodes to generate an electric field; measuring voltages at the one or more field supplying electrodes in response to the supplied electric field; and storing data including the voltages measured at each field sensing electrode, and wherein the accessing voltage measurements includes accessing the stored data including the voltages measured at each field sensing electrode.

According to some embodiments of the present disclosure, the method further includes moving at least one of the one or more tools to a new position relative to the structure; applying currents to the one or more field supplying electrodes to generate an electric field; measuring voltages at the one or more field supplying electrodes in response to the supplied electric field; and storing data including the voltages measured at each field sensing electrode.

According to some embodiments of the present disclosure, the method further includes storing data including the currents applied at each field supplying electrode, and wherein accessing the current data includes accessing the stored data including the currents applied at each field supplying electrode.

According to some embodiments of the present disclosure, the one or more field sensing electrodes are moving as the currents are applied and voltages are measured.

According to some embodiments of the present disclosure, a number of voltage measurement samples are recorded at a rate of between 300 kHz and 500 kHz.

According to some embodiments of the present disclosure, the voltage measurement samples are demultiplexed at a rate of at least 100 times a second.

According to some embodiments of the present disclosure, storing data including the voltages measured at each field sensing electrode includes updating the voltage measurements with the demultiplexed measurements at a rate of at least 100 times a second.

According to some embodiments of the present disclosure, the method further includes: positioning one or more tools inside the body and relative to the structure, wherein the field supplying electrodes and field sensing electrodes are disposed on the one or more tools; and defining one or more field supplying electrodes and one or more field sensing electrodes, wherein the current is applied at the one or more field supplying electrodes and the voltage is measured at the respective one or more field sensing electrodes.

According to an aspect of some embodiments of the present disclosure, there is provided a method of determining structural properties of a structure in a human or animal body, the method including: accessing data indicative of: spatial locations of field sources positioned relative to the structure to generate an electric field that interacts with the structure; currents injected by each of the field sources; spatial locations of field sensors positioned inside the body and relative to the structure to sense a voltage resulting from the electric field interacting with the structure; voltages measured by the field sensors in response to the injection of fields by the field sources; and determining the structural properties by determining values of parameters representing the structural properties by comparing the accessed data to calculated voltage data, wherein the calculated voltage data is voltages calculated for various locations of field sources and sensors and the accessed injected currents.

According to some embodiments of the present disclosure, the accessing data includes accessing data indicative of known dielectric properties of at least a portion of the structure, and the calculated voltage data is calculated based on the known dielectric properties.

According to some embodiments of the present disclosure, the parameters comprise one or more parameters representing a dielectric property of at least a portion of the structure.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system" (e.g., a method may be implemented using "computer circuitry"). Furthermore, some embodiments of the present disclosure may take the form of a computer program product embodied in one or more computer readable medium(s) having computer readable program code embodied thereon. Implementation of the method and/or system of some embodiments of the present disclosure can involve performing and/or completing selected tasks manually, automatically, or a combination thereof. Moreover, according to actual instrumentation and equipment of some embodiments of the method and/or system of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In some embodiments of the present disclosure, one or more tasks performed in method and/or by system are performed by a data processor (which may also be referred to herein as a "digital processor", in reference to data processors which operate using groups of digital bits), such as a computing platform for executing a plurality of instructions. Reference herein to "a processor" in the singular includes—unless otherwise distinguished—processors implemented by a plurality of processing units; including, for example, processing units co-located within a singly-packaged processing device, and separately packaged processing units interconnected through a communication network.

Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well. Any of these implementations are referred to herein more generally as instances of computer circuitry.

Any combination of one or more computer readable medium(s) may be utilized for some embodiments of the present disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable storage medium may also contain or store information for use by such a program, for example, data structured in the way it is recorded by the computer readable storage medium so that a computer program can access it as, for example, one or more tables, lists, arrays, data trees, and/or another data structure. Herein a computer readable storage medium which records data in a form retrievable as groups of digital bits is also referred to as a digital memory. It should be understood that a computer readable storage medium, in some embodiments, is optionally also used as a computer writable storage medium, in the case of a computer readable storage medium which is not read-only in nature, and/or in a read-only state.

Herein, a data processor is said to be "configured" to perform data processing actions insofar as it is coupled to a computer readable memory to receive instructions and/or data therefrom, process them, and/or store processing results in the same or another computer readable storage memory. The processing performed (optionally on the data) is specified by the instructions. The act of processing may be referred to additionally or alternatively by one or more other terms; for example: comparing, estimating, determining, calculating, identifying, associating, storing, analyzing, selecting, and/or transforming. For example, in some embodiments, a digital processor receives instructions and data from a digital memory, processes the data according to the instructions, and/or stores processing results in the digital memory. In some embodiments, "providing" processing results comprises one or more of transmitting, storing and/or presenting processing results. Presenting optionally comprises showing on a display, indicating by sound, printing on a printout, providing haptic (e.g., vibratory and/or pressure-force) indications, or otherwise giving results in a form accessible to human sensory capabilities.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example, and for purposes of illustrative discussion of embodiments of the present disclosure. In this regard, the description taken with the drawings makes apparent to those skilled in the art how embodiments of the present disclosure may be practiced.

In the drawings:

FIGS. 1A-1C schematically represent conversion of a model template (FIG. 1A) to a model instance (FIG. 1B) and optionally a display of the model instance (FIG. 1C), according to some embodiments of the present disclosure;

FIG. 1D schematically illustrates a model template for a left atrium of a heart, according to some embodiments of the present disclosure;

FIG. 1E schematically illustrates a model template for a frustoconical ostium of a blood vessel (e.g., a pulmonary vein), connected to a cylindrical blood vessel, according to some embodiments of the present disclosure;

DESCRIPTION OF SPECIFIC EMBODIMENTS OF THE INVENTION

Figure 1A:
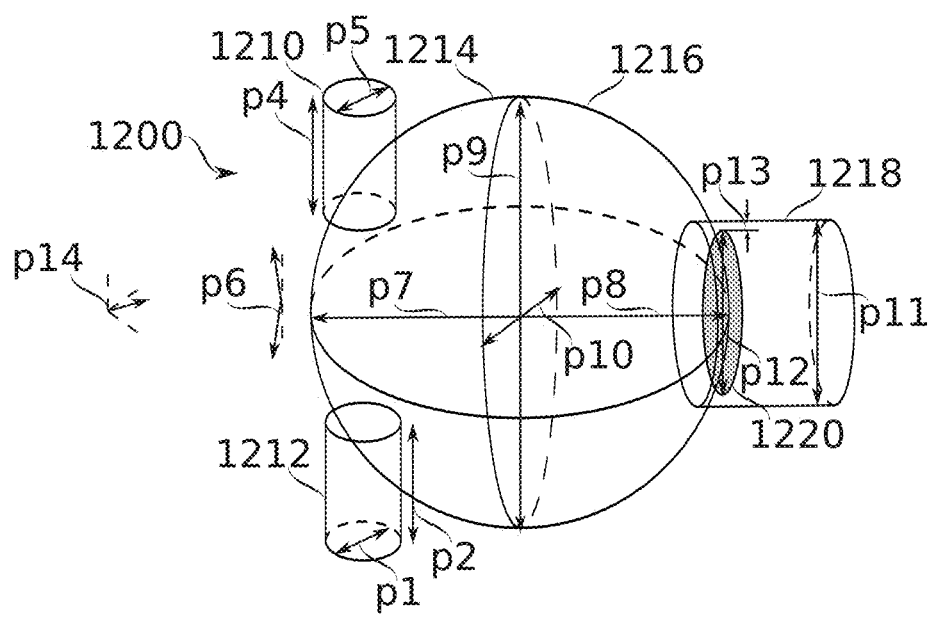

The present invention, in some embodiments thereof, relates to the field of anatomical imaging and more particularly, but not exclusively, to modelling of structures internal to a human or animal body.

Overview

A broad aspect of some embodiments of the present disclosure relates to methods and systems for determining or estimating structural properties (geometry) and/or dielectric properties of a structure in a human or animal body. In some embodiments, the structure is modelled by a model which is defined by model parameters that represent the structural properties of the structure, and by model parameters that represent the dielectric properties of the structure. In some embodiments, the determining uses a model template. The model template may comprise both structural and dielectric properties. The model template may comprise distinctly parameterized portions which contribute together to model the whole of a modeled structure.

The determination and/or estimate of the properties is expressed in the form of a model defining values assigned to parameters. The parameters represent the structural and/or dielectric properties of the modeled structure.

Structural properties include, for example, shape, size, and/or configuration (e.g., distances and directions between structural elements). Dielectric properties include, for example, conductivity, impedance, resistivity, or any dielectric properties known to the skilled person. Dielectric properties of a portion of the structure may be defined by the material composition of that structure. A model template comprises at least model parameters and indications of their significance (e.g., in defining shapes, material properties, and the like). The model template may define relationships between parameters (and these relations may themselves be parameters). There may also be values set as constants, and whatever additional information may be needed, e.g., to convert instances of the model template to images or otherwise put model instances to use. Herein, the model templates are also referred to simply as "models". Assigning values to the parameters specifies a model instance. Each property may describe or be applicable to the whole of the modeled structure, or to a portion of the structure. The collection of properties of portions of the structure contributes to the model template to describe a whole modeled structure made up of the portions.

Defining each model parameter of the model template may involve choosing/defining one or more structural and/or dielectric properties of the modeled structure to be represented by that parameter. For example, the structure may be a blood vessel, and the structural properties may include an inner diameter of the blood vessel, and/or an outer diameter of the blood vessel. Dielectric properties may include dielectric properties of the blood inside the blood vessel, and/or dielectric properties of the tissue outside of the blood vessel.

Mutual Constraints on Structural and Dielectric Properties

An aspect of some embodiments of the present disclosure relates to the joint determination of values of structural properties and dielectric properties which apply to a model instance.

Disclosed methods and systems relate to determining, for a model instance, values of one or more of the model parameters. This may involve determining values of model parameters representing dielectric properties of the structure, structural properties of the structure, or both There is, in particular, a relationship between the values of certain dielectric properties and certain structural properties which may be applied to the interpretation of electrical (e.g., voltage) measurements in terms of model parameter values. A certain measurement may be consistent with a co-varying range of values of dielectric properties, which are optionally defined by material composition, and structural properties, such that if either parameter is assigned a constraint in the value(s) it can assume, the value other parameter is also thereby constrained. For purposes of illustration, the relationship can be thought of as a function m=ƒ(s,d), where m is the value of the electrical measurement, s is the value of some structural parameter, and d is the value of some material composition defined dielectric parameter. With the electrical measurement m known, a constraint on s may constrain the range of values of d consistent with m=ƒ(s,d), and vice-versa. There may be, for example, a DC resistance due to a wall of biological tissue, the effects of which are measured, e.g., by its influence on impedance measurements (an influence which will, for example, tend to increase in strength with proximity). The wall of biological material has a certain thickness (structural parameter) and resistivity (dielectric parameter). Other factors remaining unchanged, the magnitude of the resistance will generally be proportional to both the resistivity and the wall thickness. Fixing the dielectric constant to some value or within some range thus introduces a constraint on what complementary value(s) of the wall thickness could have contributed to produce some actual electrical measurement value.

In some embodiments, parameter values are determined by finding a values that minimize or otherwise reduce an error between voltages that are measured in response to electric fields that interact with the structure, and calculated voltages which are calculated based on the model of the structure (i.e. based on the model parameters and their values). The resulting determined parameter values, together with any remaining parameter values that have been set, e.g., to a default or other constant value rather than being determined based on the measurement, therefore give an indication of the corresponding structural properties and dielectric properties of the actual structure.

Optionally, a value of one or more of the model parameters is fixed outside of the error-minimizing operations, while other parameter values (a parameter subset) are adjusted to match the model instance to the measurements. For example, model parameters representing dielectric properties of a structure may be fixed values that are assumed to be known (and not determined using the disclosed methods), whilst the values of the other model parameters, such as those representing a shape or configuration of the structure, or other dielectric properties of the structure that aren't assumed to be known, may be determined using the disclosed methods. Additionally or alternatively, model parameters representing the shape and/or size of a model may be fixed values, whilst the values model parameters representing dielectric properties of the structure may be determined using the disclosed methods. In some examples, both one or more parameters representing a structural property of the structure and one or more parameters representing a dielectric property of the structure may be fixed at constant values, whilst the values of one or more remaining structural and/or dielectric parameters are determined using the disclosed methods.

In more detail, one or more model parameters may be fixed based on predetermined values for that parameter. As an example, model parameters representing dielectric properties of a structure may be fixed based on predetermined information, such as data indicative of the dielectric properties of the structure. Additionally or alternatively, other model parameters, such as those representing a size of a structure, may be fixed based on predetermined information regarding the size of the structure. For example, the structure may be a surgical implement with known dimensions, and so the values of respective model parameters representing the dimensions of the structure may be fixed based on these known dimensions. Fixed model parameters may be fixed explicitly in terms of a corresponding constant in the model, or implicitly in terms of numerical values in the model resulting from a combination of constants or in a structure of the model. It would be understood that reference to fixing a model parameter refers to setting that parameter to a constant value. Additionally or alternatively to fixing values for model parameters, model parameters to be determined may be constrained to a predefined range, which may be defined based on approximate knowledge of the corresponding property of the structure. In such embodiments, methods disclosed herein may be used to determine a value of those constrained model parameters within the respective predefined range.

Optionally, structural and material property-type dielectric properties are conjoined into a single property in the model template, since it is not always necessary to resolve them separately—for example the influence of a wall on a measurement used to determine a lumenal shape may be similar whether it is thick and of low resistance, or thin and of high resistance. Furthermore, the actual thickness of the wall may be of secondary interest. In that case, the two parameters are optionally conflated into a single joint parameter in the model template.

Accordingly, dielectric properties of modeled tissue portions such as a cardiac wall or blood vessel wall may be specified as material property dielectric properties (a property associated with the composition of the material of the blood vessel wall as such), or as bulk dielectric properties influenced also by structure. Material property dielectric properties are independent of how much of the tissue is present: they are also referred to herein as the "specific" dielectric properties, with "specific" being understood in the sense of "characteristic of the species". Bulk dielectric properties depend also on how much of a material is present.

In embodiments of the present disclosure, bulk dielectric properties may be derived from separate parametric representations of, e.g., thickness and specific dielectric properties, and/or parametric representations which conjoin geometry with specific dielectric properties. For example, resistance of a material thickness is a bulk dielectric property, which may be represented as simply that—a resistance—but alternatively may be derived from the resistivity of a material (as a species), and how much material is present. In some embodiments of the present disclosure, the "thickness" of a tissue wall is modeled as a "bulk impedance" in terms of its effects on electrical readings.

Optionally, a structural parameter such as thickness (in millimeters, for example) is derived by making a reasonable (e.g., selected on the basis of published measurements) assumption about the specific (species-characteristic) dielectric properties of the material, and determining which thickness of tissue would combine with those dielectric properties to produce electrical measurements actually obtained. However, this may be performed after error minimization is performed, with original model fit relying just on the bulk property.

Part-Wise Parametric Model Templates From Electrical Measurements

An aspect of some embodiments of the present disclosure relates to the part-wise definition of a model template in terms of parameters which define certain parts of the model template. The parts join together in the definition of the model template (and its instances) as a whole.

Reference is made herein to model parameters representing structural properties of a structure, such as shape, size, and/or configuration (e.g., position and orientation, including relative positions and orientations of parts defined by the model template). Reference is also made to model parameters representing dielectric properties of a structure. Model parameters may represent structural properties or dielectric properties of the whole of the structure, or for a portion of the structure, the parameters for the portions of the structure collectively describing the structure, and/or describing aspects thereof within some more global model template, optionally a hierarchical model template.

In some examples, a model template may comprise one or more model parameters representing dielectric properties of a portion of a structure, and may further comprise one or more model parameters representing structural properties, such as a size or shape, for that same portion. In this manner, different portions of a structure may have one or more associated model parameters representing structural properties of that portion, and one or more associated model parameters representing dielectric properties of that portion. In other words, the model may comprise two or more parameters representing dielectric properties of respective different portions of the structure, and may further comprise two or more parameters representing structural properties, such as a shape and size, of those respective portions of the structure. The model may further comprise model parameters representing the relative arrangement of different portions of the structure.

Potential advantages of the parametric modelling approach are to keep a model's complexity at a low enough level to facilitate real-time calculation and updating. In some embodiments, the number of parameters is kept to, e.g., below 500, below 200, below 100, below 50, below 25, or below 12 parameters. The number of parameters may at the same time be at least, e.g., 200, 100, 50, 25, 12, or 6 parameters. There is, however, no particular limitation on a low number of parameters. In some embodiments, then number of measurement inputs used for determining parameter values outnumbers the number of free parameters for which model values are calculated by a factor of at least, e.g., 3, 5, 10, 20, 50 or 100.

Although electrical measurements are predictably influenced by the environment in which an electrical field is travelling, it is potentially computationally intensive to find a model which usefully describes that environment. Given a model candidate, it is typically relatively straightforward and computationally inexpensive to evaluate it against what is known—once. Computational expense expands quickly, however, when a large number of models have to be calculated in order to find one that's useful. In general, the search space grows exponentially with the number of free parameters available. Accordingly, there is a potential advantage in keeping parameter numbers low, so that fewer models need to be tried before a suitable one is found. Moreover, parameters which are selected should preferably "capture the error"— that is, the difference between picking the parameter value optimally and picking it poorly should be large in terms of impact on the model's overall fitness to what is known.

Accordingly, in some embodiments, the model's structural parameters are defined through combinations of 3-D geometrical surfaces. Optionally, the 3-D geometrical surfaces of a model's template are chosen to be computationally inexpensive approximations of a typical shape of the structure be modeled.

Another potential advantage of the parametric approach is to allow extrapolation of larger portions of the shape of a structure using measurements which may be confined (at least initially) to a relatively small portion of the whole. In particular, parameters may influence the whole of a model (e.g, its overall scale), individual parts of a model (e.g, the radius of a certain aperture), or subsets comprising individual parts of the model. Optionally, a parameter specified for one individual part may also constrain a parameter for another part. For example, a model template may specify two half-ellipsoids joined at their mid-sections. The mid-sections are constrained to have the same shape (e.g., axis lengths), even though the remaining axis of each ellipsoid is independently adjustable. Mutual constraints may be more indirect: for example, the apertures of two blood vessels entering into a heart chamber may be specified to be on opposite sides of the chamber, or with a minimum spacing between them.

Parameters can also be differentially weighted in their influence on different parts of the model. For example, there may be two (for example; optionally three or more) "global curvature" parameters, with each having a center of strongest influence on opposite (or otherwise spaced-apart) sides of a lumen. At these centers, the respective global curvatures are given maximum weight, e.g., they may effectively determine the local radius of curvature of the lumen wall. In between the centers, the relative weights of the parameters change, so that the wall curvature of a model instance varies, e.g., continuously, between one center of "parametric influence" and the other. This is another way of representing a lumen's curvature, compared, e.g., to assigning lengths to an ellipsoid's orthogonal axes.

A potential advantage of this type of parameterization is that new parameters (new "centers") can be introduced in the model template wherever appropriate to help diminish variance between actual measurements and simulated measurements produced from model instances. In some embodiments, model instances themselves are adjustable in their number of parameters, e.g., a number of parameters characterizing a curvature is adjusted upward or downward according to how well the adjustment reduces fitting error. Generally, adding a parameter will make a better fit possible, but the improvement may be negligible or difficult to realize. The parameter count can be kept relatively small, for example, by only increasing parameter count in a model instance when an error-reducing advantage above some threshold is realized. Optionally, parameter count limits are influenced by another factor, such as the number of available data points which provide information about a particular region of the modeled volume. In effect, such models are based on a template that is "quantitatively dynamic" in the structure of its parameterization, in that it allows the introduction of new parameters, but under control of the model template's definition, rather than as a simple linear function of the number of data points available.

Model templates can also be "qualitatively dynamic"; that is, switchable stepwise between a plurality of parametric definitions. This is a way of managing anatomical variation, for example. Optionally, a plurality of parametric variants of a model template are defined, e.g., a variant specifying parameters for four pulmonary veins, and a variant specifying parameters for three pulmonary veins. Error fitting may comprise testing instances of both variants and selecting the one producing an instance that fits the data best. In this case, pulmonary vein count may be seen as "just another parameter" of the model template. Additionally or alternatively, there may be an operation outside of the error fitting algorithm that identifies, e.g., that there are three instead of four distinct "holes" which the electrical measurements indicate; thereafter, just the three-vein variant of the model template is selected as a basis for error minimizing.

Parametric Reduction of Model Template Complexity

An aspect of some embodiments of the present disclosure relates to the reduction of a potentially very large number of electrical measurements to a relatively small number of parameters to be calculated (assigned values) in order to generate a model instance that describes a structure. Synergistically, the number of measurements actually needed to produce a model instance with reasonable fidelity to the structure is potentially reduced, since the reduced degrees of freedom of a relatively small number of parameters requires fewer inputs in order to provide a basis for value selection.

For example, some electrical measurement-based mapping methods involve calculating a dielectric value for every element or voxel in a finite element model, which makes the problem under-specified unless a very large number of measurements are available, and potentially with a spatial distribution that includes visits to or near each element or voxel.

The presently disclosed methods allow for the whole of or portions of a structure to be modelled as having structural properties and dielectric properties given by respective model parameters, where each of the model parameters of the model is defined by choosing a structural property or a dielectric property to be represented by that model parameter. Since parameters can represent the whole of or portions of a structure, each parameter represents a property affecting a relatively large region of space. As a result, fewer parameters are required to accurately model the structure.

Parametric Induction of Model Instance Geometry

An aspect of some embodiments of the present disclosure relates to the use of parametric model instances to represent unvisited regions of a structure, based on measurements in visited regions of the structure that constrain what is likely (or possible) for parameters affecting unvisited regions.

Anatomical structures may be usefully treated as "self-similar" in a certain sense—for example, a heart which is relatively small (compared to some reference example) in one structural aspect is likely to be relatively small in other structural aspects. Thus, a measurement of the distance across one axis of a lumen of a model instance may be used to set a global scaling that sets the sizes of other axes of the model instance (at least until more information becomes available). Similarly, anatomical structures can be assumed, at least as a baseline result, to have stereotypical placements of their major parts: for example, overall orientation of an organ; and the relative positions of its parts, e.g., chambers of a heart, and the directions from which other lumens such as blood vessels and appendages connect to them. Thus, a few measurements in one region of an anatomical structure can be used to inductively model a remainder of the anatomical structure, even if that remainder effectively did not actually influence the electrical measurements available so far. This is an advantage which a parametric modelling appropriate potentially has over a purely voxel-modelling or point-cloud based approach. It can show not only what is known, but also what is reasonable (as encoded by the model template) in view of what is known.

It is recognized that what is reasonable is not necessarily the case—that a model instance based on partial information is also likely to include errors. However, model values can be refined, in some embodiments, based on further data. Moreover, in some embodiments, the model values may be updated as new data is acquired (e.g, upon visiting an area, or even moving into proximity to it) such that at least some errors are corrected before they actually impact the procedure. A model instance which comprises an early parameterization of a heart (model instance created after only a small amount of data is collected) is potentially at least somewhat in error about what it shows, particularly for features which have not actually been visited. However, until those sites have been visited, there may be little that can be done to them which will create real problems. Furthermore, the model template may be designed with ordinary anatomical knowledge in view, so that the model at least shows in what general directions and to about what distance a physician may move an intralumenal tool (e.g., a catheter probe bearing one or more electrodes) in order to reach the only-approximately indicated features. Upon reaching them, measurements made using that same tool have potentially become available; and the parameterization can, accordingly, be refined—now with more complete information. In effect, errors about unvisited structures are rendered potentially harmless to the actual activities of a procedure, because enough is known to at least find them, and then the act of visiting them itself provides enough information to correct the error.

For this to be realized, however, the model instance needs to be updated. For some practical uses, moreover, the model instance should be updated in real time—preferably at a rate fast enough to correct potential errors before they become relevant to the attention of the physician performing the procedure. Here, a parametric representation of a structural model of an organ provides potential advantages, since the vector space needing exploration (e.g., by an error-minimizing algorithm) is constrained in its dimensionality to the number of parameters which the model template defines. This potentially reduces the computational effort required to make each new iteration of the model instance.

Elements of Methods of the Present Disclosure

In some embodiments of the present disclosure, there is disclosed a method for computing parameter values of one or more model parameters of a model, wherein the model models the structural and dielectric properties of a structure in a human or an animal body. The method comprises accessing electrical measurements (e.g., of voltage) made at different places in the vicinity of the structure by one or more in-body field-sensing electrodes in response to currents applied to one or more field-supplying electrodes. The method further comprises computing the parameter values, by adjusting the parameter values to fit predicted voltage values to the accessed voltage measurements, wherein the predicted voltage values are predicted from the model for the currents applied to the field-supplying in-body electrodes.

Data Measurements

In some embodiments, the one or more field-sensing electrodes were disposed on one or more tools positioned inside the body at the time that the accessed voltage measurements were measured. In some embodiments, one or more of the field-supplying electrodes was disposed inside the body and optionally disposed on the one or more tools at the time that the voltages were measured. In some embodiments, one or more of the field-supplying electrodes was disposed on a surface of the body at the time the measurement was obtained.

In some embodiments, the accessed electrical measurements are indicative of voltages sensed by one or more field-sensing electrodes in response to electric fields generated by currents applied to one or more field-supplying electrodes. At the time the measured voltage data was recorded, the one or more field-supplying electrodes and one or more field-sensing electrodes were disposed on one or more tools positioned relative to the structure such that the field-supplying electrodes were disposed to supply an electric field that interacted with the structure and the field-sensing electrodes were disposed to measure a voltage resulting from the electric field interacting with the structure. The voltage measurements that are accessed may otherwise be referred to herein as measured voltage data. That is, the method comprises accessing voltage measurements, which may otherwise be referred to as accessing measured voltage data.

In some embodiments, the method further comprises accessing current data indicative of the respective currents applied at the one or more field-supplying electrodes when the accessed voltage data was measured, accessing position data indicative of positions of the field-supplying and field-sensing electrodes at the time the voltages were measured, and computing the values of one or more model parameters using the voltage data, the current data, and the position data.

The measured voltage data is indicative of voltages sensed by one or more field-sensing electrodes in response to electric fields generated by currents applied to one or more field-supplying electrodes. The generated electric fields are generated using the field-supplying electrodes, by applying currents to the field-supplying electrodes, meaning that the field-supplying electrodes supply the electric field as a result of the currents applied to the filed supplying electrodes. The electric fields supplied by the field-supplying electrodes give rise to voltages which are sensed by the field-sensing electrodes. A field-sensing electrode may produce an electrical signal based on the sensed voltage, and the signal may be measured to determine the value of the voltage sensed by the electrode. For example, a voltmeter (or other suitable measuring apparatus) may be connected to the field-sensing electrode to measure the sensed voltage, thus producing a measured voltage value from the voltage sensed by the electrode. The measured voltage data may be accessed in real-time for use in the disclosed methods, i.e. accessed at the same time as when the voltages are measured by the one or more field-sensing electrodes. Alternatively, the voltages may be measured at an earlier time to when the data is accessed, such as one hour, one day, or one week before the measured voltage data is accessed for use in the disclosed methods. Specifically, the voltage data may be measured during a surgical or other medical procedure, which is then stored and is accessed at a later time separate to the procedure. It would be appreciated that the time difference between measuring and accessing the voltages may be longer than one week, or may be any intermediate time between real-time and one week. The voltage data may be acquired during a surgical or other medical procedure, which is then stored and accessed for use in the disclosed methods at the same or a later time, and subsequent to accessing the voltage data, further voltage data may be acquired as part of the same surgical procedure. This process may be repeated any number of times during the same surgical procedure.

Where reference is made to generating electric fields and supplying electric fields, it would be understood that electric fields are generated using the field-supplying electrodes, for example by applying currents to the field-supplying electrodes. The field-supplying electrodes themselves therefore supply the electric field as a result of the current applied to those electrodes.

In some embodiments, at the time the voltages were measured, the one or more field-supplying electrodes and the one or more field-sensing electrodes were disposed on one or more tools positioned relative to the structure such that the field-supplying electrodes were disposed to supply an electric field that interacted with the structure and the field-sensing electrodes were disposed to measure a voltage resulting from the electric field interacting with the structure. For example, the one or more field-supplying and field-sensing electrodes are disposed on one or more tools which may be positioned inside the structure, or near the structure, for example in the same cavity as the structure or in an adjacent cavity (such as a heart chamber). The one or more tools may be catheters, optionally Lasso® catheters, basket catheters, spiral catheters, or pig tail catheters. Alternatively or additionally, one or more of the tools disposed inside the body may be an implant positioned relative to the structure. The implant may be a left atrium appendage occluding device, atrial septum defect occluding device, or a device configured to repair or replace a portion of a heart such as an aortic valve, mitral valve, or tricuspid valve. In some examples, some of the field-sensing electrodes and/or the field-supplying electrodes are disposed on the body. In some embodiments, in addition to one or more of the one or more tools disposed inside the body being an implant, the structure may also be an implant inside the body. Consequently, in this case, there are at least two implants, the first implant being one of the one or more tools carrying the field-supplying and or field-sensing electrodes, and the second implant being the structure that is modelled.

The voltage data may be acquired using one or more field-supplying electrodes supplying electric fields and one or more field-sensing electrodes sensing voltages resulting from the supplied electric fields. Acquiring the voltage can be performed using various arrangements of the field-supplying and field-sensing electrodes. The following examples are illustrative examples of electrode arrangements that may be used to acquire the measured voltage data.

In a first example, alternating electric currents are applied to a single field-supplying electrode so as to generate an electric field in the region of the structure. The applied current may be applied to the field-supplying electrode at a given frequency, and amplitude. One or more field-sensing electrodes sense the generated electric field and as a result, the respective voltages on field-sensing electrodes change. The respective voltages on the one or more field-sensing electrodes are measured, and the measured voltages form a data set. Current data that is indicative of the current applied to the field-supplying electrode may also be stored. The current data may be indicative of the identity of the field-supplying electrode and of the frequency and magnitude of the applied current. The current data may comprise values of the applied currents known in advance of the application, or the current data may comprise measured values of the actual currents applied to the field-supplying electrodes, wherein the actual measured values may be slightly different to the values intended to be applied to the electrodes.

The first example may be extended to applying currents to a plurality of field-supplying electrodes at a given frequency at the same time. In some examples, the phase of the currents applied to each of the field-supplying electrodes may be controlled, such that the phases are different. In other words, a plurality of field-supplying electrodes simultaneously excite electric fields at the same frequency, with a controlled phase difference between the generated electric fields that are simultaneously excited. Voltages are measured using the field-sensing electrodes in response to the electric fields supplied via the plurality of field-supplying electrodes at the same frequency. Thus, a plurality of different voltage measurements may be made at the same time using each field-sensing electrode, each measurement being a voltage resulting from an electric field generated at a different phase. In these examples, the measured voltage data may include voltages measured at each field-sensing electrode at a given time for each of the electric fields generated simultaneously at the same frequency and at different phases. The current data may include the amplitude and the phase of currents applied at each field-supplying electrode.

Furthermore, in some examples a field-supplying electrode may supply electric fields and resulting voltages at a field-sensing electrode may be measured at a plurality of different times. For example, at each of a plurality of different times, an alternating current of a given frequency may be applied to a different single field-supplying electrode, and at each time, a voltage measurement may be made using a different one of a plurality of electrodes. In another example, at each of a plurality of different times, an alternating current of a given frequency may be applied to a different plurality of field-supplying electrodes, and at each time, a plurality of voltage measurements may be made using a different plurality of field-sensing electrodes. The measured voltage data may therefore comprise voltage measurements made at different times, wherein the voltage measurements made at each time are voltages measured using different ones of the field-sensing electrodes resulting from electric fields generated using different ones of the field-supplying electrodes. In one specific example, a tool may comprise 10 electrodes and one of which acts as a field-supplying electrode whilst the remaining electrodes are field sensing. The field-supplying electrode may be different for different voltage measurements made at different times.

In another example, electric currents are applied to a plurality of field-supplying electrodes at the same time (i.e. simultaneous excitation of each of a plurality of field-supplying electrodes). The current applied to each field-supplying electrode may be of a different frequency, such that each field-supplying electrode supplies an electric field at a different respective frequency. In this example, a plurality of electric fields are generated at the same time, each at a different frequency. One or more field-sensing electrodes sense the generated electric fields and are used to measure voltages resulting from the respective electric fields. Specifically, each of the one or more field-sensing electrodes may be used to simultaneously measure voltages resulting from one or more, and preferably all, of the electric fields at the different frequencies. For example, signal processing can be performed on the received signals at each field-sensing electrode (e.g. using a demultiplexer) to determine voltage measurements at each frequency. In this sense, it can be considered that a field-sensing electrode is configured to sense voltages in response to electric fields supplied at a plurality of different frequencies by means of being connected to such a signal processor. In other words, the signal processor configures the electrode to be able to sense voltages at a plurality of different frequencies at the same time. Thus, in reality whilst it is the signal processor that is configured to measure voltages at different frequencies which are sensed by electrodes, this is referred to throughout as the electrodes being configured to sense voltages at different frequencies. An example of signal processing that could be used to separate the signals at respective frequency is to analyze the frequency spectrum of the measured signals, for example using a Fourier transform, as is well known to the person skilled in the art. It would be appreciated that this example equates to a plurality of simultaneous and independent instances of the first example discussed above, wherein each instance has electric fields generated and voltages measured at a different respective frequency. The measured voltages form a data set that comprises the voltages measured at each field-sensing electrode at each frequency, in response to the excitation of the plurality of field-supplying electrodes at each respective frequency. Current data that is indicative of the current applied to each of the field-supplying electrodes may also be stored. The current data may be indicative of the magnitude and/or frequency and/or phase of the applied current at each field-supplying electrode, and identification of each of the respective field sensing and field-supplying electrodes. This example may be extended to applying currents to a plurality of field-supplying electrodes at a plurality of different frequencies, wherein for each frequency, there are a plurality of field-supplying electrodes supplying electric fields at that frequency. In some examples, the phase of the currents applied to each of the field-supplying electrodes for a given frequency may be controlled, such that the phases are different.

It would be appreciated that an electrode can function as a field-supplying electrode at a first frequency, and can simultaneously function as a field-sensing electrode at all the frequencies. In some embodiments, a voltage measurement made by an electrode at the same frequency supplied by that electrode is noisy to such an extent that it is preferable not to use such measurements for finding model parameters. Thus in some examples comprising a plurality of electrodes, each of the plurality of electrodes functions as a field-supplying electrode at a different respective frequency and simultaneously functions as a field-sensing electrode for each of the other frequencies corresponding to the electric fields supplied by the remaining plurality of electrodes.

In some embodiments, one or more ground electrodes are also provided in conjunction with a corresponding field-supplying electrode. Whilst the field-supplying electrode functions as a field source, i.e. supplying an electric field, the ground electrode functions as a field sink. A single ground electrode may be used in conjunction with a single corresponding field-supplying electrode, or a single ground electrode may be used in conjunction with a plurality of different field-supplying electrodes exciting electric fields at the same or different frequencies. Alternatively, there may a respective ground electrode for each different frequency. The ground electrode(s) may be a surface electrode positioned on the surface of the body, such as attached to the skin of a patient, or the ground electrode(s) may be disposed on one of the one or more tools disposed inside the body. In some specific embodiments, the field-supplying electrodes and field-sensing electrodes are disposed on a tool comprising 3 or more, preferably 10 or more, electrodes arranged in a circle. That is, the electrodes may be disposed along the circumference of a notional circle defined by the structure of the tool carrying the electrodes. The distance between each pair of adjacent electrodes in the circle may be equal, so that the electrodes are arranged at regular points along the circumference of a circle. A first electrode on the tool may function as the field-supplying electrode and an adjacent or opposite electrode may function as the ground electrode, while the remaining electrodes on the tool may function as field-sensing electrodes. In other specific embodiments, the each one of the plurality of electrodes supply an electric field at a different respective frequency, and simultaneously measure voltages at the frequencies excited by the other electrodes, whilst a respective ground electrode for each different frequency is disposed on the surface of the body or on a tool inside the body. Voltage measurements made using the field-sensing electrodes may be voltages measured between the respective field-sensing electrode and a ground electrode.

In the examples discussed above, it is possible that an electrode transmitting at a given frequency (i.e. functioning as a field-supplying electrode at a given frequency) may also simultaneously act as a field-sensing electrode for that same frequency. In other words, an electrode transmitting at a frequency can also be used to measure a voltage at the same transmitted frequency at the same time.

The measured voltage data is a data set comprising voltage values sensed at each field-sensing electrode and the identification of the respective field-sensing electrode. The voltages in the set are sensed in response to electric fields supplied by one or more field-supplying electrodes. In the case of excitation of a plurality of electrodes at different frequencies, the data set may comprise the measured voltage values indicative of voltages sensed at the field-sensing electrodes at the different frequencies, as well as the respective frequencies and identification of the field-sensing electrode at which the voltage was read. Each data set may include voltage measurements that were acquired at different points in time using one or more field-sensing electrodes, for example where at each separate point in time, the one or more field-supplying electrodes and/or one or more field-sensing electrodes are disposed at different locations relative to the structure. Additionally or alternatively, the data set may include voltages that were measured at the same point in time at multiple different frequencies using one or more field-sensing electrodes.

Specifically, using the examples described above, the voltage data may be acquired using a plurality of electrodes disposed at a single position and at a single point in time. For example, one or field-supplying electrodes may supply electric fields and resulting voltages are sensed by a plurality of field-sensing electrodes, or multiple field-supplying electrodes may supply electric fields at different frequencies and resulting voltages for the different frequencies are measured using one or more field-sensing electrodes. In these examples, the measurements may be made for only one position of each electrode relative to the structure and the measured voltage data may comprise the voltages measured at the single positions of the field-sensing electrodes.

Alternatively, voltage data may be acquired using the electrode arrangements in the examples described above, wherein voltage measurements are made at different points in time, wherein at each separate points the electrodes are in different locations relative to the structure. The locations are determined and associated to the voltage data (electrical measurements), building up a map which associates locations to the electrical conditions (e.g., voltages) which are measured to exist at those locations. Thus associated, the voltage data (electrical measurements) are also referred to herein as being "location-associated" (that is, they are recorded as belonging to a specified location). The locations are typically specified within some spatial coordinate system (e.g., a Cartesian coordinate system).

As an illustrative example, a single field-supplying electrode may supply an electric field and resulting voltages are measured using a single field-sensing electrode. One or both of the electrodes may be moved around such that measurements can be made at a plurality of different locations for either or both of the electrodes. In this example, the measured voltage data comprises a plurality of voltage measurements, each taken for one or both of the electrodes at different positions. It would be appreciated that measuring voltages by moving electrodes around relative to a static structure (all things being equal) and taking measurements at different electrode positions at different times produces measured voltage data in the same manner as using a plurality of electrodes and measuring voltages at a single point in time for the plurality of electrodes at different positions. In other words, it is possible to generate measured voltage data for voltages measured at different positions of the field-sensing electrodes and/or field-supplying electrodes using a plurality of electrodes each at different positions and measuring voltages at a single point in time for those positions, or using one or more electrodes and measuring voltages at multiple points in time whilst changing the positions of the electrodes. In both of these examples, the measured voltage data comprises measured voltages taken using electrodes disposed at different positions. Methods described herein may be independent of the specific methods used to acquire the measured voltage data, since the specific measurements acquired do not necessarily depend on which of the above examples is used to measure voltages sensed by the field-sensing electrodes.

As a more general example of electrodes that move to different positions within the body and voltages that are measured at those different positions, one or more field-supplying and/or one or more field-sensing electrodes may be disposed on a roving tool that moves through the body or a portion of the body as the voltage measurements are made. Specifically, the roving tool may be moving whilst signals are repeatedly measured using the field-sensing electrodes, and so each voltage measurement is made at a different respective position of the electrode(s) disposed on the tool. In some embodiments, voltage measurements may be sampled at a specific rate as the tool moves, that is voltage measurements are made a certain number of times in a given period of time. The sampling rate may be sufficiently high such that during each measurement, the electrodes are substantially in the same position. It would be understood that the higher the sampling rate, the smaller the distance travelled by the tool and thus the electrode disposed on the tool during each measurement.

As would be understood by the skilled person, the sampling rate is at least twice as high as the highest frequency at which electric fields are to be measured. In some examples, the sampling rate is between 300 kHz and 500 kHz, and in some examples the sampling rate can be up to 1 MHz or more. A certain number of samples may be recorded at the sample rate, or samples may be recorded for a certain amount of time at the sampling rate. The sampled signals may be multiplexed signals for electric fields generated at different frequencies and/or phases, and the signals may be demultiplexed using signal processing techniques as would be known to the skilled person. An example of signal processing that could be used to separate the signals at respective frequencies and/or phases is to analyses the frequency spectrum of the measured signals, for example using a Fourier transform. Performing the signal processing on the multiplexed signals therefore provides voltage measurements for each field-sensing electrode at each respective frequency and/or phase.

In one specific example, a set of 625 samples is recorded at a sample rate of 500 kHz. The samples are multiplexed signals for different frequencies and/or phases, which are demultiplexed using a discrete Fourier transform, for example. The processing provides, for each field-sensing electrode, an amplitude of the measured signal at each respective frequency and/or phase of the generated electric fields, thereby providing the measured voltage data for each electrode at each frequency and/or phase. Sets of samples may be repeatedly taken at the sampling rate, which are then demultiplexed using the signal processing at a rate of at least 100 Hz (i.e. the demultiplexing process may occur 100 times a second, each time for a different set of 625 samples). The measured voltage data can therefore be updated with new measurements recorded at each field-sensing electrode at each frequency and/or phase at the rate of at least 100 times a second.

In some examples, the demultiplexing rate and the rate at which voltage measurements are updated is 400 times a second. For example, 625 samples are recorded at a sampling rate of 500 kHz, which lasts for a duration of 1.25 ms. These samples are then demultiplexed and added to the measured voltage data, and then 1.25 ms later (after the 625 samples were recorded), 625 new samples are recorded and demultiplexed. Samples are recorded demultiplexed and resulting measurements added to the measured voltage data every 2.5 ms (i.e. at a rate of 400 times per second). Demultiplexing may also be used in the same manner to determine the applied currents at each field-supplying electrode at the respective frequency and/or phase, and the applied current data may be updated accordingly at a rate of at least 100 times a second, optionally 400 times a second.

The measured voltage data may comprise measured voltages, or may otherwise comprise other quantities indicative of measured voltages which have been derived from the measured voltages, such as electric field measurements, impedance measurement or any other measurement derivable from a voltage sensed at the field sensing of electrodes. The currents are typically time varying currents, for example varying at a given frequency or within a frequency range, for example to generate radio frequency (RF) fields, more specifically within a frequency range of 1 to 1000 kHz, preferably 10 to 400 kHz, 1 to 100 kHz or more specifically 15 to 65 kHz. Frequencies up to 4 MHz may also be used.

With reference to the accessed position data, the position data is indicative of positions of the field-supplying and field-sensing electrodes at the time the voltages are measured. The position data may comprise information indicative of the positions of a plurality of electrodes used to measure the voltage data at a single point in time (i.e. when the electrodes are at a single position), or may comprise information indicative of the positions of one or more electrodes as the electrodes are moved around and voltages are measured at multiple points in time for multiple different positions of each electrode. The position data may be explicit in terms of positions of the electrodes. For example, the position data may include position coordinates for each electrode in a reference frame, the reference frame being fixed to one of the tools carrying the electrodes, or the coordinates may be defined relative to an external reference system (outside the body). For example, the reference frame may be defined with respect to a belt, a jacket, or other garment incorporating electrodes that is worn by a subject (i.e. on the body) during data acquisition. Another example is a reference frame defined with respect to a static catheter positioned in the body. The positions of electrodes disposed on the catheter may be defined with respect to a reference frame fixed on the body, and the positions may be determined using medical imaging, such as X-ray, ultrasound, or Electrical Impedance Tomography.

In some embodiments, two or more intrabody tools each carrying electrodes may be used. In some embodiments, at least one of the tools is stationary relative to the body, providing a reference frame fixed to the body as in the case of the surface electrodes fixed to the body, and at least one of the tools may move during data acquisition. In more general terms, in some embodiments, data is collected using one stationary group of electrodes (on the stationary tool) substantially fixed in relation to the body and one group of electrodes that move from one position to the next (on the moving tool), with voltage measurements being recorded for different positions of the moving tool. The one or more field-supplying and one or more field-sensing electrodes can, in accordance with different arrangements, be distributed in any suitable manner between the electrodes disposed on the one or more tools. In these embodiments, the position data may include coordinates of the electrodes on the moving tool in a coordinate system defined relative to the stationary tool. In other words, a reference frame in which the electrode positions are provided may be fixed to the stationary tool.

In some examples the positions of the electrodes may be defined in a coordinate system that is not fixed to any known reference frame, such as a reference frame external to the body, fixed to the body or fixed to a tool. The electrode positions may instead be defined in a coordinate system that is independent of a tool or body and is not defined relative to an external reference outside of the body. A common reference frame may be determined using electrodes that move to different positions and take voltage measurements at different times. A coordinate system is determined in which the positions of all the electrodes at all the different times can be found, thereby providing a common reference frame for all the electrode positions that does not rely on landmarks inside or outside of the body to define the coordinate system.

One particular example of finding a common reference frame for moving electrodes is using the "V-to-R" or "measurement-to-location" navigation and imaging system as described in International Patent Publication No. WO 2019034944 A1, in which voltage measurements made using the field-sensing electrodes are used to determine a position of those electrodes in a common reference frame. This is done by transforming a cloud of voltage measurements (referred to as the V-cloud) that are acquired at different sets of positions of the electrodes, into positions of the electrodes at which the measurements were taken (referred to as the R-cloud).

In some examples, one way of finding the common reference frame involves making a plurality of voltage measurements for a plurality of different respective locations of the electrodes, such that enough points exist in the V-cloud (there are enough measurements at different electrode positions) to produce a voltage-to-position transformation of sufficient accuracy. In other words, the electrodes may be repeatedly moved to different positions and voltage measurements made for the electrodes at those positions until enough measurements have been made to generate an R-cloud (by transforming the voltage measurements (the V-cloud)) with a sufficiently large number of points. The transformation to the R-cloud may then be used to find the position of each electrode in a common reference frame for the existing voltage measurements and for future measurements. A reference frame may be defined based on the cloud of positions, for example with an origin at the center of the R-cloud, and so the positions of the electrodes for each voltage measurement can be determined in this reference frame. Whilst this frame of reference may not be known, for example relative to an external reference, the common frame of reference is the same for all voltage measurements taken at all the different positions of the respective electrodes. The positions of the electrodes when subsequent voltage measurements made (e.g. when a tool carrying the electrodes is moved to a new position) can then be determined in the common reference frame using the transformation.

Any other suitable coordinate system and reference frame apparent to the skilled person may be used to define the positions of the electrodes, defined relative to a known reference frame or internally defined for the measured positions, for example with an origin fixed on a selected one of the measured positions or a center of mass of all measured positions.

In some examples, the position data may be implicit rather than being expressed by a numerical value in the data set, for example, in terms of an identifier of an electrode that links the voltage measurement made at that electrode, or the current applied at that electrode, with a corresponding position of the electrode, The identifier may be implicit, for example, the place of the electrode in a known sequence of electrodes or measurements (i.e. an index value), and/or the identifier of an electrode may be a pointer to data indicative of the position of that electrode, for example at a given time.

With reference to the accessed current data, the current data is indicative of the currents applied to the one or more field-supplying electrodes when the voltage data was measured. In other words, the currents applied to the one or more field-supplying electrodes at the time the voltages were measured at the field-sensing electrodes are stored in a data set and accessed for computing the values of one or more model parameters. The current data may comprise the magnitude and/or frequency (and/or phase if there is more than one field-supplying electrode) of the currents applied to each of the one or more field-supplying electrodes at the time the voltage data was measured. The current data may include current values for currents applied to multiple field-supplying electrodes (at the same or at different frequencies) at the same point in time. Additionally or alternatively, the current data may include values for currents applied to one or more field-supplying electrodes (at the same or at different frequencies) at different points in time, for example where at each separate point in time, the one or more field-supplying electrodes and/or one or more field-sensing electrodes are disposed at different positions relative to the structure.

In some embodiments, the method further comprises accessing dielectric data corresponding to values of one or more dielectric properties of the modelled structure. Accessing the dielectric data may involve accessing the predefined values from a database. The dielectric properties may be any one or more of: conductivity, complex conductivity, real or imaginary part of conductivity, magnitude or phase of conductivity, permittivity, complex permittivity, real or imaginary part of permittivity, magnitude or phase of conductivity, impedance, complex impedance, real or imaginary part of impedance and magnitude and phase of impedance. In these embodiments, the model parameters representing dielectric properties of the structure may be fixed based on the dielectric data. For example, the dielectric data may be indicative of the value of conductivity (or other suitable dielectric property) of the whole of or of one or more portions of the structure, and so the corresponding model parameter may be fixed at this value. In these embodiments, the dielectric parameters are thus kept constant and are not determined based on the accessed voltage, current, and position data. In some embodiments, the dielectric data may indicate a predefined range for a value of conductivity (or other dielectric property) of the structure or a portion thereof, and so a corresponding model parameter may be constrained to be a value within this predefined range, meaning that the parameter is optimized to be a value within that range.

Parameter Value Calculation

In some embodiments, calculating the values of one or more model parameters comprises accessing starting values for each of the parameters and setting the parameter values to be the respective starting values. These embodiments further include computing predicted voltage values, which may otherwise be referred to as model voltage data. The predicted voltage values/model voltage data model the voltages measured using the one or more field-sensing electrodes based on the respective current data indicative of currents applied at the one or more field-supplying electrodes; the position data, and the starting values of the model parameters. These embodiments further include computing an error signal which is indicative of the difference between the model voltage data and the measured voltage data. Based on the error signal, the parameter values may be updated in order to reduce a magnitude of the error signal for subsequent model voltage calculations. In some embodiments, updating the model parameter values involves using an optimization process to determine new parameter values. The optimization process may use the previous values and the error signal, as well as other relevant factors depending on the specific optimization process in order to determine new parameter values. In some embodiments, the optimization process uses gradient descent. In some embodiments, the optimization process uses Adam optimization.

In some embodiments, in addition to error signals calculated between simulated (model-derived) voltages and measured voltages, there may be cost functions associated with one or more parameters which influence how the parameter is allowed to vary. Costs associated with these cost functions may be combined with the error signal to be jointly minimized. Preferably, in combining parameter cost function results and error signal results, the error signal based on voltage calculations is weighted to dominate the combined result throughout ranges where the parameter values are "reasonable", while the cost functions should escalate to dominate the combined result for parameter combinations which correspond to anatomically unreasonable configurations of the structure.

The cost functions may be introduced into the model to help encourage model parameters into anatomically plausible ranges. For example, there are typical relative arrangements of the blood vessel roots which open into a heart chamber, and typical relative arrangements of heart valves relative to these and other structural features. At the same time, normal anatomical variation exists. To express these priors, a cost function may be introduced into a model which penalizes unusual or implausible arrangements of structural features. For example, the superior and inferior vena cava typically enter the right atrium from opposite sides. A cost function may begin to impose a cost as their relative positions and/or angles increasingly deviate from this expectation. The cost need not be imposed for any slight deviation; e.g., the cost function can begin to be imposed, or at least be imposed significantly, only after a certain range of reasonable values is exceeded. For example, the cost of non-oppositely oriented vena cava entries into the right atrium is only added after their axes angle is less than 160°.

Optionally, at least a low cost is imposed for deviating from some ideal even within the range of normal values. This potentially establishes enough of a cost gradient to stabilize the choice of model parameter values against jumping around to different local minima, e.g., when the error signal gradient itself is not strong enough to dominate the distinction between two parameter value options. This sort of cost-function gradient-based stabilization—even if unnecessary to the final result—may be of particular value when the model is used to generate displays at intervals while it is still also annealing to a low-error state. A physician may appreciate being presented with a relatively smooth transition from a less-accurate (higher error signal) to a more-accurate (lower error signal) state of the model; this can be easier to follow cognitively. There may be a technical benefit to imposing a cost gradient to parameter values that improves the continuity of intermediate visualizations, even when this cost gradient has features which are unnecessary to (or even potentially interfere with) the performance (e.g., rate of error reduction per iteration) of simulation/measurement error reduction in the algorithm as such.

Additionally or alternatively, smoothing for purposes of presentation comprises interpolating between model states. For example, a physician may be presented with a model which is interpolated part-way between a previous set of model parameter values and a current least-error-producing set of model parameter values. The lag in error-fit quality of what the physician sees may be justified by helping to preserve a cognitive sense of continuity.

Where anatomical parameters are well characterized in advance (e.g., on the basis of pre-operative structural imaging methods such as MRI or CT-scanning), their associated cost functions may be made stricter by making variation from measured values more expensive, optionally including more expensive for smaller variations.

It should be understood that setting the parameters to the starting values applies only to the model parameters that have not been set at fixed values (i.e. setting the starting values only applies to those parameters to be optimized). For example, if the dielectric model parameters are fixed based on the accessed dielectric data which is indicative of pre-defined values of dielectric properties of the structure, then these fixed values are not set as other starting values and are not updated based on the model voltage data and the error between the model voltage data and the measured voltage data. In these examples, any fixed parameters may be used to constrain the model voltage data, by using these fixed values as appropriate in the calculation of the model voltage data.

As described above, one or more model parameters to be optimized may be constrained to a predefined range, meaning that the presently disclosed methods are used to determine a value of those model parameters within the respective predefined range. In these embodiments, the starting values of the constrained model parameters may be set at values within the respective predefined range, optionally at the center point of the respective range.

In some embodiments, the process of computing model voltage data and the error signal is then repeated based on the new, updated parameter values. In some embodiments, the parameter values may be repeatedly updated until a stopping criterion is reached. After the stopping criterion has been reached, the parameter values may be outputted.

It should be noted in particular that the stopping criterion leading to output need not be controlled only by the degree of error reduction achieved. For example, once a basic level of parameter value stability has been reached, results in the form of output are optionally output at time intervals, or simply according to the number of iterations that have been performed (even single iterations). Nor need production of output be exclusive to also continuing with error reduction calculations, in which case the "stopping" criterion is viewed rather as an "update output" criterion.

Furthermore, during a procedure, there may become available additional electrical measurement data as the procedure proceeds. Optionally, repetitions of calculations use not only updated parameter values, but also new measured voltage data (new electrical measurements) as it becomes available.

Potential synergies arise from the asynchronous combination of new measurement acquisition, continuous rapid model instance updates made available for display, and continuous iterations to reduce, for an internally represented model instance, error between actual measurements and model-predicted measurements; for example, within the context of an ongoing procedure; e.g., as described in the section describing parametric induction of model instance geometry.

Parameterization of the Model Template

Parameters of a model template may be chosen to model a selected anatomical shape according to a generalized schema of its features. A typical structure to be modeled by a model template is a body lumen, for which such type of structure the lumens of the heart provide illustrative examples.

Several "primitive" geometrical shapes are parameterized by a modest number of well-known geometrical properties such as one or more radii and/or axis lengths. These shapes and their parameters are potentially useful for defining a model template. For example, a right atrium of a heart may be parameterized generally as an ellipsoid, with apertures for the superior and inferior vena cava and an aperture for the tricuspid valve. The ellipsoid may be parameterized by its three major axes and orientation, and the apertures each parameterized in turn, e.g., as cylinders of a certain radius, position, and orientation, the aperture itself being defined at the intersection of said cylinder with the ellipsoid.

Parameterized shapes need not be limited to geometrical "primitives" such as cones, blocks, planes and ellipsoids; e.g., they can be defined by meshes of polygonal shapes, by control points of splines, or by another method. It is nevertheless a potential advantage to at least partially define the model template of a structure in terms of an assembly of explicitly defined sub-structures (e.g., valves, blood vessels, chamber wall sides with characteristic general shapes), each of which individually has relatively few parameters (e.g., 3 or fewer for the shape itself, plus parameters that define position and orientation). This reduces the degrees of freedom which must be "searched" in order to find a model which ultimately provides a good fit to the electrical measurements. Optionally, degrees of freedom can be added to a model template during one or more of a plurality of successive calculation iterations; e.g., as the amount of available data increases, as a need for resolution increases (e.g., while a physician uses a tool to interact with a target region of an anatomical structure) and/or as electrical measurements simulated from a model instance approach more closely electrical measurements actually being obtained. Optionally (e.g., to maintain performance), degrees of freedom in areas of less current interest may be reduced (the model simplified), so that computational resources are spent where it is of current benefit to a procedure. For example, upon performing an interatrial septal crossing from a right atrium to a left atrium using a catheter, details of the right atrium and/or interatrial septum which were important earlier become less important. The parameter values which specify them are optionally "frozen" (the parameters are converted to constant values). Optionally, even some values are omitted once the degree of detail they permit ceases to matter to the current phase of a procedure. For example, a septal wall which has been modeled with a spline comprising 25 or more control points in order to assist locating a crossing point is optionally reduced in complexity to be represented by 16 or fewer control points; or even a different type of 3-D surface function such as a plane or ellipsoidal section.

Returning to the example of the right atrium model template: For the ellipsoid there may optionally be substituted another parametric shape, e.g., comprised of one or more parametric surfaces defined individually as surfaces in 3-D space (for example, as a plane, ellipsoid surface section, cylinder surface section, or surface splines), and optionally joined collectively by operations such as merging and/or mutual clipping at parametric surface intersections.

Similarly, the apertures may be parameterized differently than described in the first example. In the case of the apertures being defined via 3-D shape intersections, for example, another 3-D shape may be chosen in place of the cylinder, such as a sphere, ellipsoid, or cylinder with an elliptical or other non-circular cross-section. Optionally, the model uses 3-D shape intersections simply to cut surface areas out of one surface where it intersects another. Optionally, 3-D shape intersections are used to define regions where two different 3-D shapes join up. For example, a cylinder corresponding to the inner wall of a blood vessel may be intersected with an ellipsoid corresponding to the inner wall of a heart chamber. The model template may specify that surfaces within the inter-penetrating volumes of the two 3-D shapes are removed, leaving a partial cylinder joined to a partial ellipsoid to model the location where the blood vessel is joined to the wall of the heart chamber.

Apertures may additionally or alternatively be parameterized as for example, as surface cutouts rather than as 3-D shape intersections.

There is not even a particular limitation to having just one parameterized shape at a given position. Valve leaflets, for example, occupy an aperture which is alternately open and closed. The valve may be modeled as occupying a plurality of states, and optionally transitions between those states may be modeled. The model parameters may, but are not necessarily required to link different states as belonging to a single object (e.g., the valve leaflets). Greater fidelity to the actual lumenal shape may potentially be achieved by using more parameters in the model template to increase the potential level of detail available. In some embodiments, this is achieved by adding more parameters to parts that a template defines. For example, a circular cross section has one parameter of length; an elliptical cross-section: two. More complex shapes with additional parameters can be defined, e.g., using splines or other mathematical functions. Additionally or alternatively, more complex shapes can be defined by, e.g., unions and/or intersections of geometrical primitives or other shapes such as cones, blocks, ellipsoids, and spline surfaces. For example, funnel-shaped ostia of blood vessels leading into and/or out of the heart may be parameterized as cone portions attached to cylinder portions. A model template may be dynamically defined to begin with relatively few parameters, and add them systematically, e.g., as the amount of available measurement data increases, and/or as error calculations decrease enough to indicate that the model instance is approximately correct within the limits of its parametric resolution. Adding complexity only after an initial fit to the data is made potentially helps reduces the cost of the solution search—since the more complex model can begin from a solution (model instance) which is already close being to correct. When model instance determination is being performed mid-procedure, this potentially contributes to achieving a faster update rate.

Similarly, model templates may be defined with finer features, such as ridges or apertures of smaller blood vessels, that can be "turned off" (their parameters ignored) during a first stage of parameter value determination, and then turned on once the basic shape of the model instance has been generated.

Because the measurements being used to refine the generic model template into a more particular model instance are specifically electrical measurements (e.g., of voltage, current, and/or a derived feature such as impedance), values of parameters reflecting the electrical properties of the environment being modeled (dielectric properties) are also important.

Typical value ranges for tissues of different types are generally known, but within these ranges there can be a normal variation, e.g., due to tissue inhomogeneity (such as may occur in fibrotic vs. healthy heart muscle, for example). The thickness of a tissue (e.g, a heart wall) also plays a role in its effects on electrical measurements. However, to the measurement, this effect can alternatively "look like" a difference in dielectric properties, when the estimated thickness and actual thickness are different. To compensate for this, structures such as lumenal walls may be modeled in the model template as having both "inner" and "outer" shapes, which may be coupled to each other so that the region between them defines a tissue thickness. Dielectric properties may be constrained, e.g., to be constant in a particular structure or region thereof, so that the model forces thickness changes.

Further Examples of Structural Shape Parts

In some embodiments, the model parameters may include parameters representing a position of the structure relative to a reference frame. The position parameters may be a single 3-dimensional vector (e.g. with Cartesian or polar position coordinates), or may be three separate parameters, each defining one component (e.g. x, y or z, or radial, azimuthal, or inclination) of the position. Additionally or alternatively, the model parameters may include parameters representing an orientation of the structure in a reference frame. The orientation parameters may be represented as a single three-dimensional vector or as three separate parameters, each defining an angle of rotation (e.g. pitch, yaw and roll relative to respective rotation axes). While reference is made to a three-dimensional position, methods of the present disclosure may equally relate to one- or two-dimensional position. For example, the position of the structure may be defined by one, two, or three spatial coordinates. Similarly, the orientation of the structure may be defined by one, two, or three angles.

The position and/or orientation of the structure may be defined with respect to a reference frame fixed to the body or a reference frame that is independent of the body, such as a reference frame fixed to the one or more tools.

In some embodiments, the model parameters include parameters representing a shape of the structure. There may be a plurality of shape parameters, each shape parameter corresponding to an aspect of the shape of the model. For example, the shape parameters may include a radius of curvature of a curved portion of the structure, an angle subtended between two lines or planes, parameters of a spline defining a curved edge or surface of the structure, or distances or relative coordinates between defined points on the structure. Shape parameters may also include parameters describing a set of polygons which define the surface of a structure, such as 3-D coordinates for the corners of each of the set of polygons. The model parameters may include size or other dimension parameters, for example representing a length, width, depth, thickness, diameter of the structure or aspect of the structure. Model parameters may simultaneously be indicative of two or more structural properties. For example, a radius may be indicative of both a shape and a size of a structure or portion of a structure.

Relationships of Measurement Positions to Parameter Values

In some embodiments, the structure comprises a blood vessel or a portion of a blood vessel. In some of these embodiments, the blood vessel or portion thereof is modelled as a cylinder and the value of a parameter representing the diameter of the cylinder is determined, thereby providing an indication of the diameter of the blood vessel. In these embodiments, the model parameters representing the dielectric properties of the blood vessel may be fixed. For example, dielectric data may be accessed which contain predefined values of dielectric properties of the volume surrounding the cylinder, and/or predefined values of one or more a dielectric properties of the volume inside the cylinder. Corresponding model parameters may be fixed using the dielectric data. The dielectric data may be predefined values accessed from a database. Alternatively or additionally, these model parameters may not be fixed and the values of one or more dielectric properties (e.g. inside and/or outside the blood vessel) may be determined using the presently disclosed methods.

In these embodiments, the measured voltage data is acquired using electrodes disposed on a tool positioned in the blood vessel, and specifically in a certain portion of the blood vessel. In some such embodiments, it is possible to estimate the diameter of the blood vessel at multiple different positions along the length of the blood vessel by moving the tool along the blood vessel. Specifically, the tool carrying the electrodes can move along the blood vessel and can take voltage measurements at certain positions along the blood vessel at different respective times, and these measurements may be used to determine a value of a parameter representing the diameter of the blood vessel at the certain position along the length of the blood vessel. The tool can then be moved to a new position along the length (i.e. the tool can be moved longitudinally along the length of the blood vessel) and new voltage measurements can be taken in order to determine a value of a parameter representing the diameter at the new position. This method can be repeated for many different points along the length of the blood vessel in order to estimate the diameter at each of the points. The position data for each electrode at each point may be determined in a common reference frame for all electrodes at all positions, for example using the V-to-R method as described above.

In these embodiments, the dielectric properties of the blood vessel may be constant or substantially constant along the length of the blood vessel. Thus the model parameters representing the dielectric properties at each portion of the blood vessel may be fixed based on predefined dielectric data (which is constant for each portion), or may be fixed based on parameter values already determined for a different portion.

It can therefore be considered that the whole blood vessel or a portion thereof may be modelled as a plurality of cylinders of different diameters, wherein the diameter of each cylinder is determined from measurements taken by the tool inside the blood vessel at respective positions along the length of the blood vessel. Alternatively, the blood vessel or portion thereof may be modelled as a truncated cone, where the diameter variation is determined using the voltage measurements taken by the tool at different positions along the length of the blood vessel. Methods of the present disclosure can therefore be used to determine whether a blood vessel is narrowed in a particular place.

Parameterize Modeling of Tools In some embodiments, the structure is a surgical implement. In these embodiments, the model parameters representing the dielectric properties of the implement (or of different portions of the implement) may be fixed. For example dielectric data may be accessed which contains values of one or more dielectric properties of one or more portions of the surgical implement, which may be positioned in a portion of the body, such as a heart chamber. The dielectric data may include predefined accessed values, for example accessed from a database, and the corresponding model parameters may be fixed using the dielectric data. Alternatively or additionally, these model parameters may not be fixed and the values of one or more dielectric properties (e.g. of the whole or of different portions of the implement) may be determined using the presently disclosed methods. In some embodiments the surgical implement is an expanding implant such as a Watchman™ left atrial appendage occluding device. One or more of the model parameters may correspond to a degree of expansion of the implant.

In some embodiments, the model of the expanding implant comprises a first model parameter corresponding to the degree of expansion of the modelled structure, a second model parameter corresponding to a position of the modelled structure, and a third model parameter corresponding to an orientation of the modelled structure. As described above, the position and orientation may be defined in a reference frame fixed to the body or to a portion of the body, for example a position within the heart chamber, or may be defined relative to a tool inside or on the body. Alternatively, the surgical implement may move within a cavity within the body, and so the position and/or orientation of the implement may be defined relative to a previous position and/or orientation of the structure. Optionally, the previous position/orientation has been determined using the presently disclosed methods or using other methods, such as an external tracking system.

In some embodiments, the structure comprises an internal tissue surface. The structure may be a wall of a body cavity, and the tissue surface may be internal surface of the wall. The structure may be a leaflet in a heart cavity and the tissue surface may be surface of the leaflet.

In some embodiments, when accessed voltage measurements were measured, the one or more field-supplying electrodes were disposed inside the cavity. Optionally, the one or more field-supplying electrodes and one or more field-sensing electrodes were disposed on a tool and in a plane, and optionally the tool was contacting the internal tissue surface when the voltages were measured. In these embodiments, the tool may be a Lasso catheter.

In some embodiments, the one or more model parameters comprise a parameter representing a distance between the tool and the internal tissue surface, and a parameter representing an angle between the plane of the electrodes and the internal tissue surface.

In some embodiments, the internal tissue surface may be modelled as a plurality of planar surfaces, each surface having a respective model parameter representing a distance between the catheter and the surface, and a respective model parameter representing an angle between the catheter and the surface. Optionally the internal tissue surface may be modelled as a composite surface by combining the plurality of planar surfaces, e.g., using algorithms such as level set, active surface, or other algorithms configured to reconstruct a surface from distances and directions between the surface and nearby points.

In some embodiments, the internal tissue surface may be modelled as a planar surface, a portion of a cylindrical surface, a portion of an ellipsoidal surface, or a portion of a spherical surface.

In some embodiments, the one or more model parameters may comprise a parameter representing the thickness of the wall, and/or a dielectric property of the internal tissue structure, and or a dielectric property of a material on the side of the wall outside the body cavity. The material on the other side of the wall may be identified based on a computed value of the model parameter representing a dielectric property of a material on the other side of the wall. The body cavity or a specific portion of the wall of the cavity may be identified based on the computed values of the one or more model parameters. The body cavity may be a heart cavity, and identifying the body cavity may comprise identifying the heart cavity.

In some embodiments, the parameter values are computed for each of a plurality of candidate models. Each candidate model may model the structure as a different respective candidate structure, and each candidate structure is defined by a different respective set of one or more model parameters. Computing the values of the sets of model parameters for each candidate model may comprise carrying out the disclosed method for computing model parameter values for each candidate model. This may comprise, for each candidate model, computing predicted voltage values, computing an error signal, and adjusting the one or more model parameter values, and repeating until a stopping criterion is reached.

In some embodiments, one of the candidate models may be selected to model the structure based on the respective number of repetitions of: computing predicted voltage values; computing an error signal; and adjusting the one or more model parameter values, that are required before a stopping criterion is reached. Optionally, the candidate model that requires the fewest number of repetitions before the stopping criterion is reached is selected.

In some embodiments, the modelled structure may be classified based on the candidate structure of the selected candidate model. Optionally, classifying the modelled structure may comprise determining a geometric property of the modelled structure based on a corresponding geometric property of the candidate structure.

The methods described above are independent of the details of how and when the data is acquired.

In some embodiments, methods of the present disclosure further comprise operations to acquire the measured voltage data, the current data, and the position data. In particular, these embodiments are embodiments in which the measured voltage data is accessed in real time as the voltages are measured, as opposed to other embodiments in which the voltage data is measured and then accessed at a later time. Specifically, in these embodiments, the method as described above may further comprise applying currents to one or more field-supplying electrodes to generate electric fields, and measuring voltages sensed by the one or more field-sensing electrodes in response to the generated electric fields. The data indicative of the currents applied, and the voltages measured are then stored in respective data sets, or as respective parts of a single data set. In these embodiments, the methods may further comprise moving one or more of the electrodes to a new position, and repeating these operations of applying currents, measuring resulting voltages, and storing the voltages and currents for the new electrode position(s).

In some embodiments in which the measured voltage data is accessed in real time as the voltages are measured, the method of acquiring the measured voltage data, the current data, and the position data further comprises positioning each of the one or more tools relative to the structure, for example in the structure or in region near the structure. One or more field-supplying electrodes and one or more field-sensing electrodes are then defined, wherein the current is applied at the one or more field-supplying electrodes and the voltage is measured using one or more field-sensing electrodes. As described above, one, some, or all the electrodes may simultaneously supply and sense electric fields. For example, all the electrodes may simultaneously supply electrical currents of respective frequencies, and sense electrical currents of the fields supplied by the other electrodes. In some embodiments, fields applied by a field-sensing electrode is sensed by the same electrode, e.g., in addition to being sensed by all the other electrodes.

Elements of Systems of the Present Disclosure

In some embodiments of the present disclosure, a system for determining the values of one or more model parameters associated with a model of a structure in a human or animal body is provided. The system may be configured to carry the methods of the present disclosure. Specifically, the system comprises a processor configured to carry out any one or more of the disclosed methods, and further comprises a memory configured to store the voltage data, the position data, and the model parameter values.

In some embodiments, the system further comprises a plurality of electrodes disposed on one or more tools suitable for insertion into the body or placement on the body, and means for generating electric fields by applying currents to the electrodes, such as an electric field generator, and means for measuring voltages sensed by the electrodes, such as an electric field receiver.

Computer Readable Media and Data Access

In some embodiments of the present disclosure, there is provided a non-transitory computer readable medium carrying instructions that, when executed by one or more processors, cause the processors to carry out any one or more of the disclosed methods.

There is further provided, in some embodiments, a method of determining structural properties of a structure comprising accessing data indicative of spatial locations of field sources positioned relative to the structure to generate an electric field that interacts with the structure. The method further comprises accessing data indicative of currents injected by each of the field sources, and further comprises accessing data indicative of spatial locations of field sensors positioned relative to the structure to sense a voltage resulting from the electric field interacting with the structure. The method further comprises accessing data indicative of voltages measured by the field sensors in response to the injection of fields by the field sources. The method further comprises determining the structural properties by determining values of parameters representing the structural properties by comparing the accessed data to calculated voltage data, wherein the calculated voltage data is voltages calculated for various locations of field sources and sensors and the accessed injected currents.

In some embodiments, accessing data comprises accessing data indicative of known dielectric properties of at least a portion of the structure, and the calculated voltage data is calculated based on the known dielectric properties. In some embodiments, the parameters comprise one or more parameters representing a dielectric property of at least a portion of the structure.

Where reference is made to voltage measurements being made in the vicinity of the structure, it would be understood that this refers to a volume of space near to or surrounding the structure. As such, a tool placed in the vicinity of a structure may be placed near to the structure, and may be for example less than 5 cm away from the structure, optionally less than 2.5 cm away from the structure, preferably less than 1 cm away from the structure. Thus, measurements made in the vicinity of the structure are made using electrodes positioned near to the structure, for example less than 5 cm away from the structure, optionally less than 2.5 cm away from the structure, preferably less than 1 cm away from the structure.

Definitions of Terms and Scopes of Teachings Indicated by Examples

Where reference is made to 'in-body' electrodes, it would be understood that 'in-body' electrodes refers to electrodes that are disposed inside a body or are configured to be disposed inside a body. Optionally, the in-body electrodes are disposed inside the body only for the duration of carrying out a medical procedure, and are taken out of the body during or immediately after the procedure. For example, electrodes disposed on a tool (such as a catheter) that is configured to be inserted inside a body (and taken out) may be referred to as in-body electrodes. The term intra-body electrodes may equally be used.

Whilst reference is made herein to accessing measured voltage data using electrodes disposed in, and optionally on, the body, it would be appreciated that some embodiments of the present disclosure are directed to accessing measured voltage data that has already been measured at an earlier time. In these embodiments, accessing the voltage data comprises accessing stored measurements that are already recorded. Other embodiments may include operations of obtaining the voltage data using electrodes disposed relative to the structure as described herein.

Reference is made herein to a 'body'. It will be understood that any reference to a body refers to the body of a human or animal.

Different aspects and embodiments disclosed herein are provided with various different features. However, it would be readily understood that the disclosed embodiments are illustrative examples and are not limiting. Features associated with different embodiments may be combined in any suitable manner as necessary.

The present disclosure relates to modelling a structure in a human or animal body. The model of the structure is defined by one or more parameters that each or collectively define structural properties and/or dielectric properties of the structure. The structural property or properties, and the dielectric properties, of the structure represented by the parameters may depend on the nature of the structure itself. For example, the structure may be a surgical implement, such as a tool, disposed inside the body during a surgical procedure. The structural properties represented by the model parameters may therefore include, but are not limited to, a position or an orientation of the tool. It would be appreciated that such a model can therefore aid an operator when controlling a tool inside a body by providing information on the position and/or orientation of the tool. In some cases, the modelled tool may be configurable to change its size, shape and/or configuration, and the model parameters may include corresponding parameters defining aspects of the size, shape and/or configuration of the tool.

In other examples, the modelled structure may be a portion of the body itself, such as an organ, a region of an organ, or some other portion inside the body. In these examples, the structural properties represented by model parameters may therefore include, but are not limited to, a shape, size, thickness, and/or some other dimension of the structure, whilst dielectric properties of the structure or portion of the structure may include, for example, conductivity, resistivity, impedance, or any other dielectric property known to the skilled person. In some embodiments discussed below, the structure may be a blood vessel and the model may be characterized by parameters representing: a diameter of the modelled blood vessel; and dielectric properties of the blood inside the blood vessel and the tissue outside the blood vessel. It would be appreciated that such information provided by the model has many uses in the field of medicine and surgery. For example, determining a diameter of a blood vessel using the disclosed methods is useful in determining if there is stenosis (narrowing) of the blood vessel, or for determining the severity of the stenosis. Such information can be used to determine, for example, whether a stent is needed in the blood vessel.

Some known finite element methods involve calculating a dielectric map of the structure. Specifically, a finite element method is used to calculate values of a dielectric property for every voxel or element in a finite element model. Thus, in contrast to the presently disclosed methods, a structure is not modelled using parameters defining structural properties of the structure in these methods, rather dielectric values are evaluated for individual voxels. The individual voxels do not themselves define structural properties of the structure. It will be appreciated that in such known methods, increasing the resolution of the dielectric map results in an increased number of voxels for which the dielectric value must be determined. In order to provide a sufficiently detailed picture of a structure using known methods therefore requires values of a large number of voxels to be solved, wherein the number of voxels is typically much larger than the number of measurements used to determine the values. This is because each parameter of the finite element model only represents the local value of dielectric properties (i.e. the dielectric properties in that voxel alone).

In contrast to these methods, methods of the present disclosure determine values of parameters that are each defined as representing a specific structural property or a specific dielectric property of structure. Methods of the present disclosure are advantageous in that the number of parameters to be determined to model the structure in the body can be reduced, preferably to be fewer than the number of voltage measurements. Instead of calculating a dielectric map where the value of the dielectric property must be determined for each element of a finite element model, model parameters are evaluated which represent dielectric properties or structural properties for at least portions of a structure. For example if the structure is a heart chamber or includes a portion of a heart, a single parameter may represent a conductivity on the blood inside the heart, a further parameter may represent a conductivity of the heart wall and a further parameter may represent a conductivity of the tissue outside of the heart wall. If known, the dielectric data indicative of known dielectric properties of the structure can be used to constrain the model by fixing corresponding dielectric parameters in the model to be constant values, such that the present methods are used to determine structural properties of the structure (such as a shape or size of the heart or portion of the heart). Additionally or alternatively, if one or more structural properties of the structure are known, corresponding structural parameters may be fixed at constant values whilst the values of the remaining structural or dielectric parameters are determined using the optimization methods disclosed herein.

Thus, in contrast to known methods where each parameter to be found describes only a dielectric value of a single voxel in a dielectric map, which by itself does not convey any useful information regarding the structure, the disclosed methods model the structure using parameters that describe structural properties or dielectric properties of the structure as a whole, or of component portions thereof. Each model parameter is therefore by itself indicative of a structural property or a dielectric property of the structure, and significant information on the structure may be provided by each parameter. In the examples in which the model describes structural and dielectric parameters of different portions of a structure, the structure may comprise fewer than 20, optionally fewer than 10, and optionally fewer than 5 different portions of which one, some, or all of these portions may be modelled using respective model parameters. This means that the model may comprise one or more model parameters representing different structural or dielectric properties for each of a number of portions, wherein the number of portions is fewer than 20, optionally fewer than 10 and optionally fewer than 5.

In the following description, numerous specific details are set forth in order to provide a thorough understanding of the disclosure. However, it will be understood by those skilled in the art that the present disclosure may be practiced without these specific details. In other instances, well-known methods, procedures, and components have not been described in detail so as not to obscure the present disclosure. The terms 'injecting signal', 'injecting current', 'exciting signal' and 'exciting current' will be all used herein after to describe signals provided to electrodes used in systems and methods described below. Moreover, the term "field-supplying electrodes" used herein refers to electrodes at which current is applied or 'injected' in order to generate an electric field or fields which interact with the modelled structure. It is therefore considered that the field-supplying electrode supplies an electric field. The term "field-sensing electrodes" used herein refers to electrodes at which voltages are sensed, the voltages resulting from the electric fields supplied by the field-supplying electrodes. It will be appreciated that any given electrode may be a field-sensing electrode at one time and a field-supplying electrode at another time.

It will be understood that the present disclosure may be embodied in a system, a method, and/or a computer program product. The computer program product may include a computer readable storage medium (or media) having computer readable program instructions thereon for causing a processor to carry out aspects of the present disclosure.

The flowchart and block diagrams in the figures illustrate the architecture, functionality, and operation of possible implementations of systems, methods, and computer program products according to the disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In the following detailed description, the term catheter may refer to any physical carrier of one or more electrodes for insertion of the one or more electrodes into a living body—for example: endoscope, colonoscope, enteral feeding tube, stent, graft, implant, etc. More generally, a tool for insertion into a body, for example, surgical tool or implant, may be read in place of "catheter" in what follows. The electrodes on such a catheter or tool may be referred to as intra-body electrodes or in-body electrodes. A catheter may include or may be, for example: a guidewire with electrodes, a micro catheter with electrodes, a sheath with electrodes, a suture thread with electrodes, a spiral catheter with electrodes, a basket catheter with electrodes or a pig tail catheter with electrodes. In some embodiments, such a catheter may carry field-supplying electrodes only or field-sensing electrodes only. In these embodiments, two or more tools or catheters may be employed to carry out methods according to the present disclosure, wherein at least one tool carries field-supplying electrodes and at least one tool carries field-sensing electrodes. In other embodiments, a catheter or tool may carry a combination of both field-supplying and field-sensing electrodes, in which case methods of the present disclosure may be carried out using one or more catheters. In some embodiments, one or more catheters placed inside the body may be used in combination with one or more body surface electrodes. In these embodiments, body surface electrodes may function as the field-supplying electrodes and the intra-body electrodes function as the field-sensing electrodes, or vice versa. Alternatively, intra-body electrodes and body surface electrodes may both function as field-supplying and field-sensing electrodes.

The field-supplying electrodes may be connected to a signal source that is configured to apply/inject currents at the field-supplying electrodes in order to generate electric fields. The signal source may be configured to apply currents at a desired frequency, magnitude, duration of time, and phase. Similarly, the field-sensing electrodes may be connected to a signal receiver that records, i.e. measures and stores, voltages sensed by the field-sensing electrodes as a result of the electric fields supplied by the field-supplying electrodes. While reference is made here to the phase of the applied currents, it would be appreciated that phase refers to the phase difference between signals applied at different field-supplying electrodes. The term phase may therefore equally be considered a relative phase, being the phase difference between the signal applied to different electrodes. Accordingly, it would be appreciated that phase control may be used when more than one field-supplying electrode is used.

Whilst reference is made to electrodes disposed on tools (e.g. catheters) that are placed inside the body, in some embodiments, some of the field-supplying and/or field-sensing electrodes may be disposed outside the body, specifically placed on the surface of the body. In these embodiments, the electrodes may be body surface electrodes, or body surface pads disposed on the surface of the body. Embodiments of the present disclosure may employ intra-body electrodes only (e.g. electrodes disposed on a catheter), or a combination of intra-body electrodes and body surface electrodes.

The following description is made with reference to voltage measurements. However, it should be noted that embodiments of the present disclosure are not limited to voltage measurements and may deploy other measurements, such as current and/or impedance measurements. Impedance measurements may be obtained from voltage and current measurements on one or more electrodes. Voltage and current measurements may be real-valued (e.g., measure the absolute value of the voltage and/or current) or fully complex.

The following description is also made with reference to dielectric properties of the modelled structure.

The skilled person would understand that a dielectric property refers to a molecular property inherent in all materials capable of impeding electron movement and hence creating polarization within the material when exposed to an electric field. A dielectric property may be specified with respect to the species of the material (that is, as a "specific" dielectric property; for example, resistivity), or with respect to a bulk amount of the material (that is, as a property jointly influence by the amount of material and its specific dielectric properties; for example, resistance). A dielectric property of a material may refer to a property characterizing and/or influenced by (in whole or in part) the material's electrical polarization when the material is exposed to an electric field.

In general, a dielectric property is a material property that depends on the material composition of a material in question and is inherent in the material, even though it may change depending on the physical state and/or surroundings of the material, for example its temperature, pressure and the like. It would be understood that reference to the dielectric properties of the modelled structure may refer to any suitable dielectric property of the structure and includes (but is not limited to) the conductivity, conductance, resistivity, resistance, permittivity, capacitance, permeability, inductance, specific impedance and impedance. The dielectric property may be real or complex, or may be the real or imaginary part of the complex value. It should be understood that the real and imaginary parts of a complex value of a dielectric property can also be used to determine the magnitude and phase of the dielectric property. The dielectric property may therefore equally refer to the magnitude or phase of a dielectric property of the structure, which, as appreciated by the skilled person, can be derived from the real and imaginary parts of the complex value of the dielectric property.

Descriptions of Figures

Before explaining at least one embodiment of the present disclosure in detail, it is to be understood that the present disclosure is not necessarily limited in its application to the details of construction and the arrangement of the components and/or methods set forth in the following description and/or illustrated in the drawings. Features described in the current disclosure, including features of the invention, are capable of other embodiments or of being practiced or carried out in various ways.

Figure 1B:
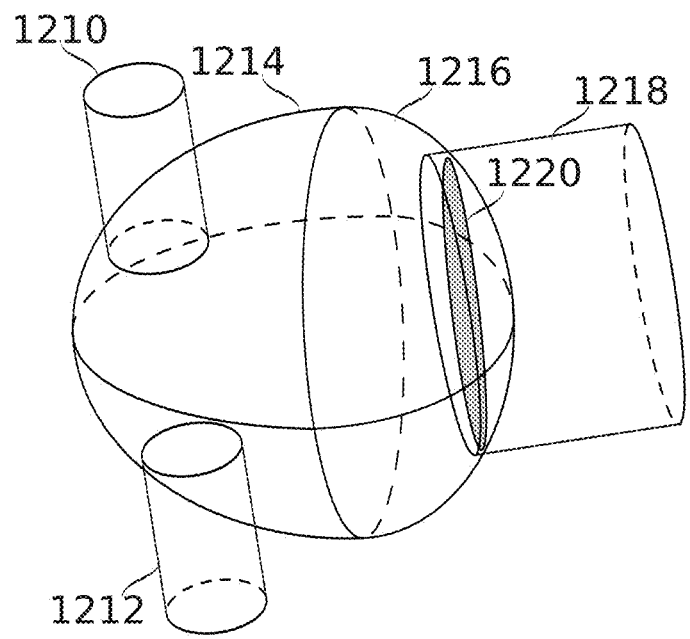

Reference is now made to FIGS. 1A-1C, which schematically represent conversion of a model template (FIG. 1A) to a model instance (FIG. 1B) and optionally a display of the model instance (FIG. 1C), according to some embodiments of the present disclosure.

FIG. 1A represents a part-wise defined parametric model template for a right atrium of, e.g., a human heart. The model shown defines cylindrical shapes 1210, 1212 for the superior and inferior vena cava respectively; two ellipsoidal halves 1214, 1216 defining the main lumen of the right atrium, another cylinder 1218 for the outer diameter of the valve annulus of the tricuspid valve, and a disc 1220 which serves as a simplified representation of the leaflets of the tricuspid valve. For simplicity of illustration, the parts of FIGS. 1A-1C have been drawn without indications of tissue wall thickness. The shapes shown may be taken to represent, in the model template, inner lumenal surfaces of the right atrium, while the wall thicknesses would be represented by shapes somewhat outset from what is shown.

Optionally (e.g., as shown in FIG. 1A), the parameters of the parametric model are seeded with initial values which approximate a reasonable "average" or "typical" shape of a right atrium; and/or which, upon iterative calculations of electrical measurement prediction error (e.g., as described in relation to FIG. 3B), readily descend an algorithmically defined "search gradient" to a configuration of minimal error. For example, the initial state of the model may be selected to be different enough from any likely end state to avoid being trapped in a local minimum of error reduction, but still close enough that the error minimizing algorithm can detect a gradient along which to modify the parameters to reduce measurement prediction error. Computational power permitting, the algorithm may be started and/or restarted from a plurality of starting configuration, to help reduce likelihood of trapping the algorithm in local minimum. Some error-minimizing algorithms known in the art have their own methods of adjusting to avoid local minimum trapping.

As for the parameters themselves, the model may be defined in several ways, of which the following descriptions are illustrative examples.

In general, each of the shapes 1210, 1212, 1214, 1216, 1218, 1220 is associated with position and orientation parameters, relative to some common frame of reference. The overall model template 1210 may be provided a global coordinate system (represented by a plurality of parameters p14 comprising, e.g., translation, rotation, and/or scaling parameters) which may itself be transformed to match the spatial coordinate system to which electrical measurements are referenced.

Several features of the right atrium important to the interpretation of electrical measurements can be taken as well-known, e.g., typical dielectric properties and wall thicknesses. These can be set as constant, or allowed to vary within relatively small (e.g., ±25%) ranges. Although there is variation among individuals, from region-to-region, and even from moment-to-moment (e.g., due to the beating of the heart), the relatively high contrast in dielectric properties, e.g., between blood, muscle, and connective tissue, is expected to dominate the error-minimizing procedure (e.g., due to sharp rises in impedance that occur near tissue walls), irrespective of estimate errors in assumptions about wall thickness and/or exact dielectric property values. As has been described hereinabove, wall thicknesses and dielectric properties can, in some embodiments, be conflated, for example into a "wall impedance" which can optionally be used in calculations.

However defined, these "wall thickness" parameters are optionally associated with any of the shapes 1210, 1212, 1214, 1216, 1218, 1220. It is noted in particular that apart from also being different than blood itself, blood vessel walls, heart chamber walls, valve annulus connective tissue, and valve leaflet connective tissue are each distinct from each other in their dielectric properties, e.g., due to their different material compositions, and/or due to their differing thicknesses.

More purely geometrical parameters (indicated in FIG. 1A as parameters p1-p14) associated with each of the parts optionally include the following. Some examples of parameters that extend "between" parts are also mentioned.

For the blood vessel cylindrical shapes 1210, 1212: an inner diameter p1, p5 (e.g., as described in relation to FIG. 5), and optionally a length p2, p4. In some embodiments, cylindrical shapes 1210, 1212 are constrained to positions which intersect the surface of half-ellipsoid 1214. Optionally, the shapes are furthermore constrained to be oriented preferably at about 180° (or another angle) from one another (p6), and to intersect half-ellipsoid 1214 preferably on opposite sides. These constraints can be implemented, for example, by incorporating to the measurement error-minimizing function (e.g., of FIG. 3B) a cost function separate from measurement error as such that introduces the effect of an increase in error as the baseline constraint is violated by larger and larger amounts. The penalty may be minimal or zero for small deviations, and grow larger as the deviation appears more and more "unreasonable" according to the assumptions of the model template.

For the half-ellipsoids 1214, 1216, optionally three orthogonal axes. The half-ellipsoids 1214, 1216 are furthermore constrained (optionally) to mate at a common cross-section (defined, e.g., by p8, p10). A third axis p7, p8 is defined separately for each half-ellipsoid. This may be a hard constraint, e.g., they may share two of their three axis length parameters in common.

Heart tricuspid valve 1220 and valve annulus 1218 are optionally constrained to vary together (e.g., proportionally) in diameters p12, p11, as well as in position and orientation. Optionally, one or more parameters (e.g., distance p13) are implemented to allow slight variations in relative diameter and/or orientation, offsets from concentricity, or other changes. Again, parameters for adjusting linked parts relative to one another are optionally associated with a penalty cost when a target value or target range is exceeded.

FIG. 1B shows a model instance which could be arrived at after fitting to suitable measurement data. Systems and methods of acquiring electrical measurement data (e.g., voltage and/or current measurements) are further described, for example, in relation to FIGS. 4, 9, 10, and 11A-12. The measurement data are also associated with positions. The positions may be known in terms of some absolute spatial coordinate system (in which case model fitting can be scaled to real-world scales), or relative, e.g., relative to a mathematically constructed system of positions, or some relative measurement scheme like distance along a parametrically defined path travelled by an electrode as it is advanced along and/or across a lumenal space.

If positions of electrical measurements taken were shown in the same frame of reference as FIG. 1B, they would generally be found within the lumenal spaces, potentially with some crossing out due to, e.g., the beating of the heart and/or errors enforced by the parametric limits of the model template. The illustrated result shows that shapes 1210, 1212 have increased in diameter, and somewhat rotated about the left-to-right axis extending through both of ellipsoid halves 1214, 1216. They remain generally parallel to each other, e.g., as a result of relative-orientation constraints mentioned in relation to FIG. 1A.

The ellipsoid halves 1214, 1216 have changed at least in the length of their unshared axis. Valve annulus cylinder 1218 has changed in diameter and orientation. Valve leaflet disk 1220 has skewed in angle compared to valve annulus 1218. Optionally, this skew is encouraged by an additional linkage criterion that pulls the valve into an orientation that matches the orientation of the circumference of intersection of valve annulus 1218 and ellipsoid half 1216.

In FIG. 1C, finally, the model instance represented in FIG. 1B has been converted to a model display. The valve annulus cylinder 1218 is removed, along with the portion of half-ellipsoid 1216 which was contained in cylinder 1218 beyond the circumference of intersection. Valve leaflet disk 1220 is aligned to a plane that is substantially parallel to this circumference (the circumference, however, may be non-planar). Finally, the intersection of cylinders 1210, 1212 with half-ellipsoid 1214 is managed by removing from each the region of mutual overlap that intrudes into the other beyond their respective circumferences of intersection.

The resulting shape, due to its parametrically limited degrees of freedom, can only be an approximation of the actual right atrium shape. However, it have potential utility as a guide to navigation, e.g., of a tool which is moving within it, which may be the same too that was used to map it, or another tool introduced to the lumen for purposes, e.g., of diagnoses and/or treatment.

The shape shown is not necessarily a "final" shape; it can be an intermediate model instance which refines further as there are:

Further iterations of the error-minimizing algorithm; and
Further inputs of electrical measurement data and their positions.

Useful effects, in some embodiments, of constraining the model template to a reduced parametric model include one or more of:

A "reasonable looking" model instance (in embodiments where it is displayed) is available early on; optionally within the first 100 measurements, after a first crossing of a lumenal space that establishes an estimate of global scale, or within a period during which no more than 10% of an overall lumenal interior surface has been visited by a measuring probe to within 1 cm or within 2 cm. Despite the relatively few and/or sparse availability of measurements, the parametric model shows general positions of key landmarks—optionally including landmarks that have not been visited or measured from.

Successive iterations on the model parameters can yield progress (error reduction/fit improvement) relatively quickly, and with relatively little computation, since: the number of free parameters is (1) restricted, and (2) optionally well-chosen (at the time of model template design) to control key features understood to be of importance to visualization and/or navigation.

As the number of measurements grows, the model instance optionally incorporates them and adapts. The model optionally iterates on its initial data over time to get a better error-minimizing fit, and also on new data as it becomes available. Calculations can be adapted to mitigate potential slow-downs due to an ever-increasing number of measurements, for example as described in relation to FIG. 3B

The number of parameters can optionally be modified to focus computational effort where desired in the parametric model; for example, to potentially increase the fidelity of modeling at times and/or places where detail is more important (or decrease it when/where it is less important). Optionally, the model predefines triggers for such modifications, e.g, upon a tool reaching a certain proximity to a modeled feature or portion thereof. Some functions such as spline surfaces are readily adapted to accept more or less control points (parameters) along their extents while maintaining a basic shape.

Reference is now made to FIG. 1D, which schematically illustrates a model template for a left atrium of a heart, according to some embodiments of the present disclosure.

In the model template illustrated by FIG. 1D, the four cylinders 1310 represent four pulmonary veins leading into the volume of the left atrium's main lumen. The main lumen itself is represented, again here by two half-ellipsoids 1314, 1316. Mitral valve leaflets are represented by disk 1320, while cylinder 1318 represents the mitral valve annulus. Cylinder 1312 represents an aperture into the left atrial appendage. FIG. 1D overall shows another configuration of parts which are similar individually, and optionally also in their interrelationships to those which were described in relation to FIGS. 1A-1C. It may be noted that the surface along which pulmonary veins 1310 are distributed is optionally replaced by a non-ellipsoidal surface, for example, a flat or cylindrical surface. Also, one or more of cylinders 1310 is optionally omitted (or, e.g., two of the cylinders merged into a differently parameterized shape) to represent the possibility of a normal anatomical variation. Other normal anatomical variations may be tested for, e.g., by substituting different parametrically defined shapes in place of the cylinder 1312 representing a left atrial appendage.

Reference is now made to FIG. 1E, which schematically illustrates a model template for a frustoconical ostium 1412 of a blood vessel (e.g., a pulmonary vein), connected to a cylindrical blood vessel 1410, according to some embodiments of the present disclosure. This is a slightly more complex parameterization than, e.g., the cylindrically represented pulmonary veins 1310 of FIG. 1D. Optionally, the frustoconical part is defined in part by parameters that define the cylinder itself (e.g., orientation and offset in space), partially by parameters of its own (e.g., its base radius and/or the pitch of its sides), and partially by its relationship to the cylinder, e.g., variable offsets in angle or position.

Figure 2:
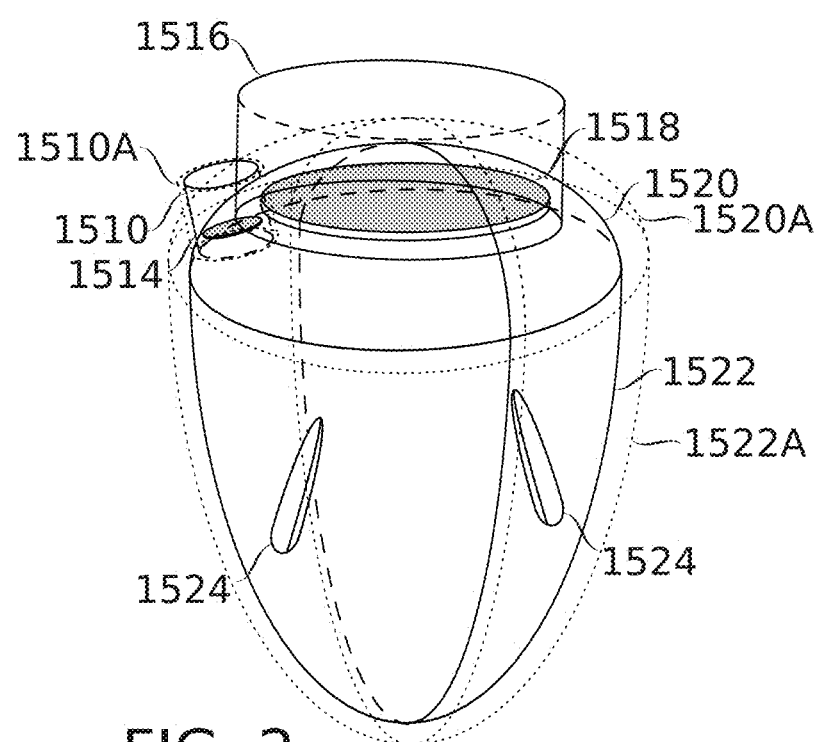
FIG. 2 schematically represents a left ventricle, according to some embodiments of the present disclosure.

Reference is now made to FIG. 2, which schematically represents a left ventricle. Half-ellipsoids 1520, 1522 (and their parameters) define the main inner lumen of the left ventricle; cylinder 1516 (and its parameters) represent the valve annulus. Optionally, papillary muscles are represented by shapes 1524 (e.g., modeled as partial ellipsoids). The aortic root is represented by cylinder 1510, and the aortic valve by disk 1514. Disk 1518 represents valve leaflets.

In this example, a parameter of tissue thickness is also depicted, in the form of ellipsoid halves 1522A, 1520A outset from ellipsoid halves 1522, 1520; cylinder 1510A; and thicknesses (cylindrical lengths) provided to disks 1514, 1518. A parameter of thickness (and/or a parameter combining tissue thickness and dielectric properties) should also be understood as associated with, e.g., the models of FIGS. 1A-1E, although not explicitly depicted in those cases. Thickness may be parameterized as a parametric shape in its own right (e.g., as an additional "shell"); or, alternatively, associated to a surface-defining shape as a property of the shape itself, either constant (the same over the whole shape) or changing (different at different shape surface positions).

It should be noted that the use of the half ellipsoid is only one of numerous options for modeling the main lumen of a heart chamber. Quadratic and cubic splines, for example, are functions which offer great flexibility for representing curvatures—for example, they can well-approximate ellipsoidal shapes, but also many others. Splines are also readily amended to incorporate more control points (parameters), and thus potentially correspondingly a closer approximation of simulated electrical measurements to actual electrical measurements.

Figure 3A:
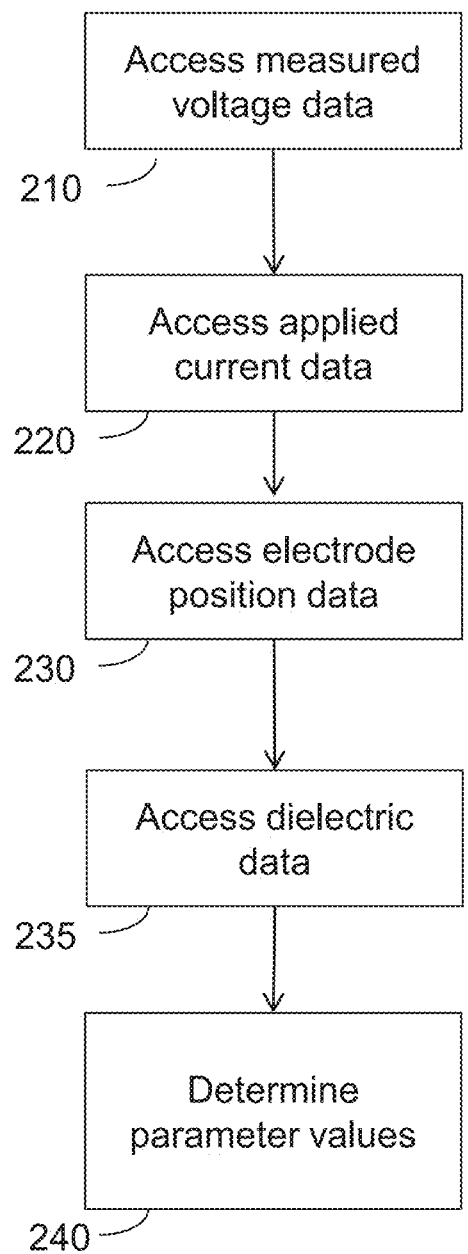
FIG. 3A depicts a flowchart for a method of determining the values of one or more model parameters for a model modelling a structure in a body.

Reference is now made to FIG. 3A, which is a flowchart schematically diagramming a method of determining the values of one or more model parameters for a model modelling a structure in a body, according to some embodiments of the present disclosure.

At block 210, in some embodiments, measured voltage data is accessed, wherein the measured voltage data comprises voltage values that, at the time of the measurement, are measured using one or more field-sensing electrodes in response to electric fields generated by currents injected at one or more field-supplying electrodes. At the time of measurement, the field-sensing electrodes and field-supplying electrodes are disposed on one or more tools positioned inside the body in any suitable arrangement as described above. For example, some or all of the electrodes may be disposed on one or more catheters or tools positioned inside the body. Alternatively, some of the electrodes may be disposed on the body, for example the electrodes may be surface pads disposed on the surface of the body. The measured voltage data comprises an indication of the specific field-sensing electrode at which the voltage reading is sensed. For example, the indication may be an index value for the electrode, or may be indicative of the position of the electrode. The measured voltage data may be comprised within a data set that also comprises values indicative of currents applied to the corresponding field-supplying electrodes (for example current values, electrode charge values, electric field values at the electrode in question). In other words, data for currents applied at field-supplying electrodes and data for resulting voltages measured using field-sensing electrodes may be stored in a single data set. Alternatively, the current data may be stored in a separate data set.

Details of how the measured voltages are obtained are provided below with reference to FIG. 4. It will be appreciated that methods of the present disclosure may include a precursor to block 210 of placing surface electrodes on a patient and/or inserting the intrabody electrodes into the patient. However, in some embodiments, the method excludes any surgical steps and is limited to receiving or accessing data sets of values indicative of voltage measured using the field-sensing electrodes (for example voltage values, impedance values, electric field values) and performing the disclosed data processing on the received data sets to determine parameter values for the model of the structure. For example, the data sets may have already been recorded at a previous time and stored in data storage, and the block 210 may involve accessing the data from data storage. In other examples, accessing the data may happen in real time as the voltage measurements are made. In other words, the operation of accessing the voltage data may involve receiving the measurements directly from the field-sensing electrodes. Alternatively, the electrodes at which the voltages are sensed may send signals to a processor to which the electrodes are connected. The processor may then record a voltage measurement based on the signal, and the operation of accessing the voltage data may involve receiving the measured voltages from the processor.

As discussed above, the voltages measured using the field-sensing electrodes (i.e. the voltages sensed by the field-sensing electrodes) are indicative of the electric field at the position of those electrodes. The electric field at the positions of the field-sensing electrodes results from the electric field supplied by the field-supplying electrodes that travels through or interacts with dielectric material in the region of the electrodes. It would be understood by the skilled person that the electric field strength at the field-sensing electrodes depends on factors such as the distance from the electric field source (the field-supplying electrodes) and the dielectric properties of the material that an electric signal passes through. Thus the voltages sensed by the field-sensing electrodes depend on the dielectric properties of the material in the region of the electrodes.

At the time the voltage measurements are taken, the field-supplying electrodes are disposed relative to the structure such that the electric field supplied by the electrodes interacts with the structure. The field-sensing electrodes are disposed relative to the structure such that the field-sensing electrodes can sense a voltage resulting from the generated electric field interacting with the structure. In other words, the electrodes are positioned near the structure such that the electric field supplied by the field-supplying electrodes interacts with the structure which gives rise to the resultant measured voltages. It would be understood that reference to the electrodes being near the structure may depend on the structure in question, and the types of electrodes used. In some embodiments discussed below with reference to FIG. 5, the structure is a blood vessel and the electrodes are disposed on a catheter disposed inside the blood vessel. In other embodiments, for example as discussed below with reference to FIG. 6, the structure is a surgical implant in a heart chamber, and the electrodes may be disposed on one or more tools positioned in the same heart chamber or in an adjacent heart chamber. In any case, it would be appreciated that at the time the measurements were made, the field-supplying and field-sensing electrodes were disposed on one or more tools positioned relative to the structure, and separate from the structure itself.

Reference is made herein to an electric field interacting with the structure. The skilled person with a knowledge of electromagnetism will understand how a structure with given dielectric properties interacts with an electric field to which the structure is subjected. For example, it would be understood that the conductivity of a structure affects the current that can pass through the structure, and thus affect the resultant voltage that can be sensed by field-supplying electrodes.

At block 220, in some embodiments, current data is accessed. The current data is indicative of the currents applied to the corresponding field-supplying electrodes at the time the voltage data was measured at the field-sensing electrodes.

At block 230, in some embodiments, position data for the electrodes is accessed. Specifically, the position data indicates the positions of the field-supplying and field-sensing electrodes at the time the voltage data accessed at block 210 was obtained. In some embodiments, the position data indicates the position of the electrodes relative to a reference frame fixed relative to the body. For example, some of the electrodes may be surface electrodes placed on the body, and their position is defined in a reference frame relative to the body. In some embodiments, some or all of the electrodes are disposed on one or more tools, and the position of each electrode is known relative to the respective tool on which it is disposed. The positions of the one or more tools may be defined with respect to a common reference frame, optionally, fixed relative to the body. In other embodiments, the positions of the electrodes may be defined relative to a reference frame fixed to one of the tools, and the reference frame may be independent of the body. In other embodiments, the positions of the electrodes are defined in a common reference frame that is independent of the tools or the body.

At block 235, in some embodiments, dielectric data for the structure is optionally accessed. Accessing the dielectric data may involve retrieving the data from a database. Specifically, the accessing may be carried out if dielectric properties of the structure are known or if the dielectric properties can be estimated. Based on the dielectric data, model parameters representing corresponding dielectric properties of the structure may be fixed, that is, set at fixed values. Alternatively, the model parameters representing the dielectric properties of the structure may be determined in addition to the model parameters representing structural properties of the structure. It would be appreciated that accessing dielectric data for certain portions of the structure and fixing parameters representing the dielectric properties of those portions may be performed in addition to determining values of parameters representing dielectric properties for certain other portions of the structure.

In embodiments where dielectric data is accessed (i.e. operations of block 235 are carried out) the dielectric data indicates values of one or more dielectric properties of the structure, such as conductivity, impedance, resistivity, permittivity or any other dielectric property known to the skilled person, and may include real, imaginary or complex values of that property. The dielectric data may provide dielectric information for different portions of the structure, or may be indicative of a distribution of dielectric properties of the structure. For example, in some embodiments the structure is a blood vessel, and the dielectric data includes a first value of a dielectric property inside the blood vessel and a second value outside the blood vessel. In other embodiments, the structure is a surgical tool and the dielectric data includes values of a dielectric property for one or more portions of the tool. The dielectric data may further include a distribution of values across different portions of the tool.

The values of the dielectric properties contained in the dielectric data may be based on knowledge of the material of the structure. For example if the structure is a surgical tool of a known material or materials, the dielectric properties of that material(s) may be known. If the structure is a portion of the body, such as a blood vessel, the values of the dielectric properties of the material inside (e.g. blood) and outside (e.g. body tissue) may also be known, at least approximately. Optionally, the values of the dielectric properties contained in the dielectric data may be estimated based on knowledge of the material of the structure.

In addition to or instead of accessing predefined dielectric data at block 235, other model parameters may be fixed based on predefined knowledge. For example, a shape or size of a structure or portion of a structure may be known (or estimated to sufficient accuracy), and corresponding parameters in the model may be fixed based on this knowledge.

At block 240, in some embodiments, parameter values for the parameters of the model are determined. In more detail, operations of block 240 comprise computing the values of the model parameters for the model of the structure, based on the voltage data accessed at block 210, the current data accessed at block 220, the position data accessed at block 230 and optionally the dielectric data accessed at block 235. The model of the structure is characterized by one or more parameters that define structural properties and dielectric properties of the model, which correspond to structural properties and dielectric properties of the modelled structure. The parameter values determined at block 240 therefore provide information on the structural properties of the actual structure in the body, such as one or more of: the position, orientation, shape, and dimension of the structure in the body, as well as dielectric properties of the structure. Further details of how the values of the model parameters are determined is provided below with reference to FIG. 3B.

Figure 3B:
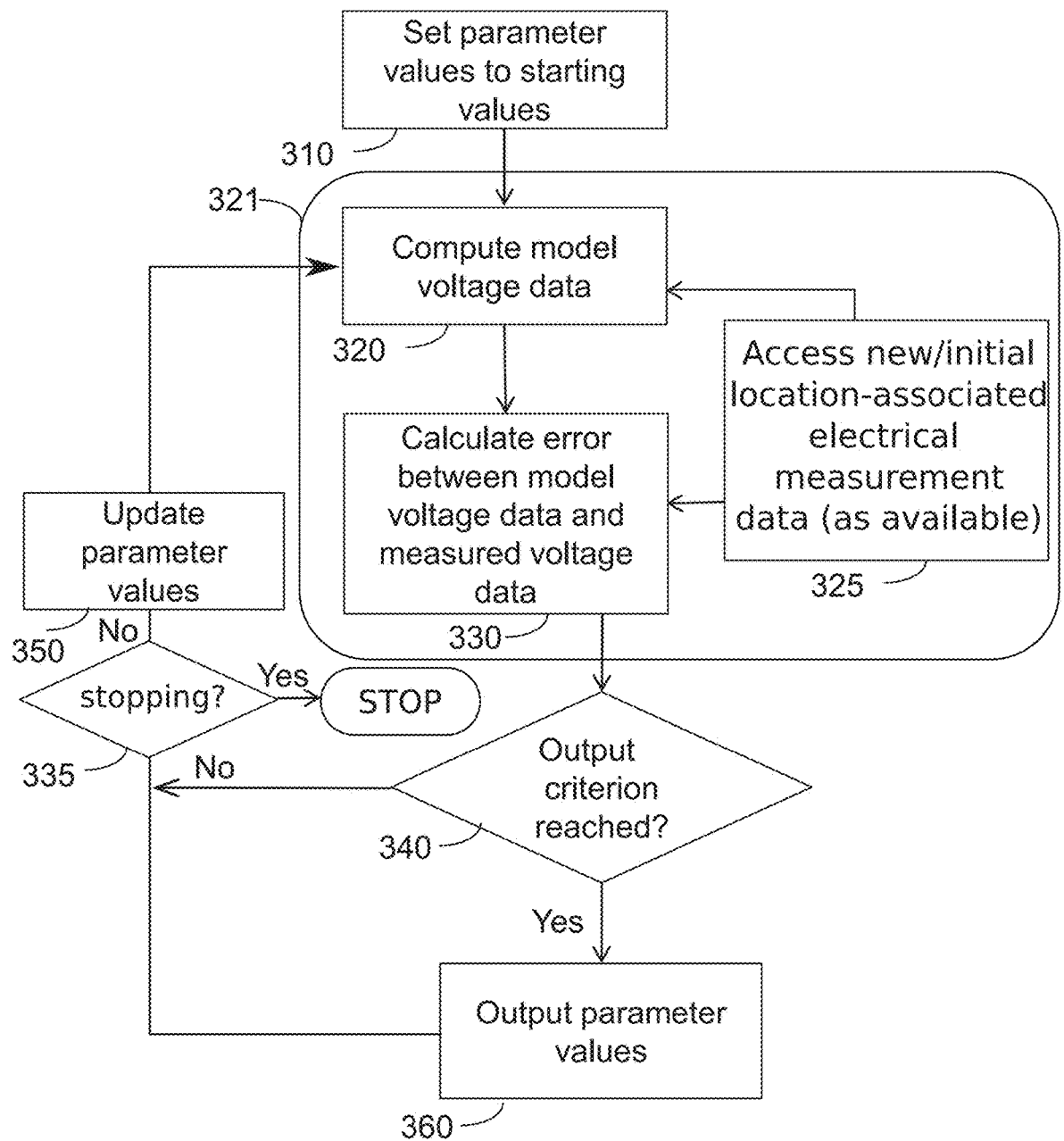
FIG. 3B depicts a flowchart for a method of computing values of one or more model parameters according to some embodiments of the present disclosure.

Reference is now made to FIG. 3B, which schematically illustrates a flowchart of a method of computing the values of the model parameters according to some embodiments of the present disclosure. The method uses accessed voltage data, position data, and current data as described above, and optionally also uses accessed dielectric data to fix the values of model parameters representing corresponding dielectric properties of the structure.

At block 310, in some embodiments, model parameter values are set to starting values. The starting values may be accessed from memory on a computing system or may be inputted by a user. The starting values may be randomly initialized, based on a starting guess and/or may be based on knowledge of the structure. For example, in some embodiments the structure is a blood vessel and the diameter of the blood vessel is modelled by a model parameter. In these embodiments, the starting value for the diameter parameter may therefore be based on knowledge of a typical diameter size. In other embodiments, the structure includes a surgical implement and the position coordinates of the surgical implement is modelled, either in a reference frame or relative to other position coordinates of the model determined for a different set of voltage measurements (e.g. taken when the one or more tools are in different positions). In these embodiments, the starting values for the position parameters may be set to zero. Alternatively, the position parameter values may be initialized to a set of coordinates based on an approximate location of the structure and/or part of the structure.

The starting values for the model parameters representing dielectric properties of the structure (if not fixed using predefined dielectric data) may be based on knowledge of the structure. For example, in some embodiments the structure is a blood vessel and the starting values may be based on knowledge of dielectric properties of blood. In other embodiments, the structure is a surgical implement and the starting values may be based on knowledge of the dielectric properties of the material or materials constituting the implement.

At block 320, in some embodiments, the model voltage data is calculated for each of a plurality of locations, based on the parameter values determined at block 310. The selection of which locations to calculate voltages for within the model is optionally influenced by which positions are represented in the location-associated electrical measurement data of block 325. Positions calculated may be the same as were measured, for example; or, for example, calculations may be performed at greater or lower spatial densities in certain regions depending on the positions for which corresponding electrical measurements are available.

The model voltage data represents the voltages expected to be sensed by the field-sensing electrodes based on the currents applied at the field-supplying electrodes, the position data for the electrodes, and the values of the structural model parameters. The model voltage values for each field-sensing electrode are calculated using physics knowledge apparent to the skilled person, such as Maxwell's equations or Laplace's equations. The model voltage data for the voltages expected to be sensed by each field-sensing electrode is calculated given the locations of the field-sensing electrodes in a reference frame (or given the locations of the electrodes relative to one another), and is based on current data indicative of currents applied to the field-supplying electrodes at known positions. The model voltage data is further based on the model of the structure, specifically the parameters representing the structural and dielectric properties of the structure. In practice, the electric field supplied by the field-supplying electrodes will interact with the structure and thus the structural and dielectric properties of the structure may affect the voltages sensed at the field-sensing electrodes, and the resulting measured voltages based on the sensed voltages. The effect that the structure has on the measured voltages is therefore reflected in the model voltage data simulating the voltages sensed by the field-sensing electrodes, since the model voltage data is calculated based on the structural and dielectric properties of the model.

At block 330, in some embodiments, the error between the model voltage data and the measured voltage data is determined for each field-sensing electrode. The error signal is computed as a function of the magnitude of the difference between measured and modelled voltage values. The function may be simple, for example the absolute or squared difference, or may include further terms to guide optimization as is well known in the art of function optimization. The error may also be calculated along with error functions related to the model template, for example, to penalize parameters and parameter combinations that deviate from predetermined constraints like preferred orientations, reasonable size ranges, concentricity and/or relative distance of model template parts, and so on.

In some embodiments, the choice of model instance locations to simulate measurements for is influenced by circumstances of the procedure. It may be useful to simulate measurements directly at positions corresponding to real-measurement positions. This has the potential effect of biasing the model to more accurately fit regions which are most-visited, potentially conferring an automatic preferential treatment to the areas which the physician's own movements indicate is of greatest interest to the current procedure. Optionally, older measurements are gradually reduced in weighted importance. A potential result of this is that errors inherent to the parametric model's limitations are preferentially "assigned" to regions of the model instance which are not of current particular interest. Simulated-measurement locations in the model instance can also be compared to measurement values which are interpolated between actual measurements, e.g., interpolated in space by a function spline (e.g., a linear, quadratic, trinomial, or spline fit).

As numbers of actual measurements increase, there may potentially be a drop-off in update rate, with voltage measurement simulations coming to take up more and more processing time, so that time saved, e.g., by use of a parametric model, becomes less important. There are various ways to "claw back" at least some of this calculation time. One is to bin together (e.g., average) measurements positioned near each other, reducing the recalculation of redundant information. Another is to adopt a modeling approach that slows or stops the recalculation of simulated values which have ceased to undergo much change from iteration to iteration. Thus, for example, simulated measurements corresponding to new actual measurement locations may be calculated immediately upon new measurements becoming available, and optionally on every iteration for a few iterations. As the parametric model "settles in" in the new location, the interval of checking can be increased. If, on the other hand, intermittent checks show that some "aged out" locations are beginning to contribute more error again, their checking duty cycle can be correspondingly increased.

A further feature—and potential advantage—of the parametric modelling approach is that the parameters can be flagged already in the model template according to their importance to the overall stability and/or quality of the model. While gross metrics can be calculated, e.g., from point cloud or 3-D mesh representations, there may arise a problem of determining, reproducibly and on the fly, which particular gross metric should be calculated (e.g, from which point to which point a "diameter" should be calculated). In the parametric model, a clear diameter is predetermined.

This opens up the opportunity to "probe" key metrics for their robustness in the face of changes to the underlying set of measurements. For example, key features such as vascular aperture diameters may be expected, in a stabilized model fit, to remain relatively constant (e.g., within about 1%-5% from iteration to iteration, or better). If stability is within a satisfactory range, then it may be beneficial to begin discarding some data (optionally checking on the effect of stability each time and/or over time), in order to reduce wasted computational effort. The recovered computational resources can be devoted instead to maintaining or increasing model update speeds, and/or to focusing fitting of existing and/or addition of new parametric features on regions from which measurements are being more actively obtained.

At block 340, in some embodiments, an output criterion is checked. The output criterion may be that the error has fallen below a threshold value, or the error is changing by less than a threshold amount compared to previous iterations. The output criterion may also be based on a number of iterations of the method, by an elapsed time (e.g., a second or less, in order to provide quickly updating output) or may be any other suitable stopping criterion apparent to the skilled person.

If the output criterion has not been met, the method proceeds, in some embodiments, to block 335, where stopping is evaluated. In the case of a one-pass implementation of the algorithm (e.g., where there are no real-time constraints and/or no new data), the output criterion of block 340 may also be the stopping criterion. In some embodiments, the method of FIG. 3B continues for as long as a procedure continues, and/or for as long as there is new data being acquired, as discussed below in relation to block 325.

The main loop of the method continues with block 350, at which the parameter values are updated. If there exist two or more parameters, one, some or all of the parameter values may be updated (for use in testing a new parameter configuration at block 330). Any parameters that may have been fixed already, for example using predefined data, are not updated. In some embodiments, updating the parameter values involves using an optimization process to determine new parameter values. The error signal may be used to control updating the model parameter values using gradient descent on a gradient of the error or other well-known optimization techniques (treating the model parameters as the optimization parameters, that is, as parameters with values that are changed to reach the stopping criterion). Specifically, in some examples, the optimization technique may be an Adam optimization technique, otherwise known as an adaptive moment estimation optimization technique. Reference is made to King ma, D. P. & Ba, J. (2014), 'Adam: A Method for Stochastic Optimization', which outlines the method of Adam optimization. Alternatively, any appropriate optimization technique apparent to the skilled person may be used to determine new parameter values.

Once the parameter values have been updated, the method continues at block 321, which encapsulates blocks 320, 325, 330 to show that they may be repeated in common upon re-entry to these operations from block 350. At block 320, new model voltage data are calculated based on the updated parameter values. The update may also include accessing new location-associated electrical measurement data as available at block 325, in the case that the computation of model voltage data is guided, e.g., by the positions found in the location-associated electrical measurement data.

The method proceeds to block 330 at which the new error is calculated between the measured voltage data (optionally now supplemented by new voltage data accessed at block 325, e.g., if any has been acquired since the last iteration) and the new model voltage data, and the stopping criterion is again checked at block 340. This process is repeated and the parameter values are iteratively updated until the stopping criterion has been reached.

Once the output criterion has been met, the method proceeds, in some embodiments, to block 360, at which the current parameter values (the parameter values set in the last iteration of the process, or the parameter values set at block 320 if there are no iterations) are outputted. If model parameters have been fixed, for example based on pre-defined dielectric data or other knowledge of the structure, these parameters may not be output since they are already known. Outputting the parameter values may involve storing the values in memory in a computing system, and/or may involve printing the values, for example to a display of a computing system.

Outputting may be used to generate a display indication of the shape of the model instance, e.g., for use in guiding a medical procedure. Optionally, the display includes indication of a tool position with respect to the shape of the model instance, the tool position being determined, for example, as described in relation to FIG. 6, and/or 7A-7D.

With reference to the parameter values, the outputted parameter values represent estimates of the corresponding structural and dielectric properties of the modelled structure and are indicative of that structural or dielectric property. For example, if the diameter of a blood vessel is modelled and the diameter is represented by a parameter, the outputted value of that parameter is an estimate of the actual blood vessel diameter. The error in that estimate may be given by the calculation made at block 330.

With reference to any dielectric parameter values, the outputted values represent estimates of the corresponding dielectric properties of the modelled structure. For example, if a blood vessel is modelled and the dielectric properties of the material inside and outside of the blood vessel are modelled, the outputted parameter values are estimates of the respective dielectric properties inside and outside of the blood vessel, with an error given by the calculation made at block 330.

Figure 3C:
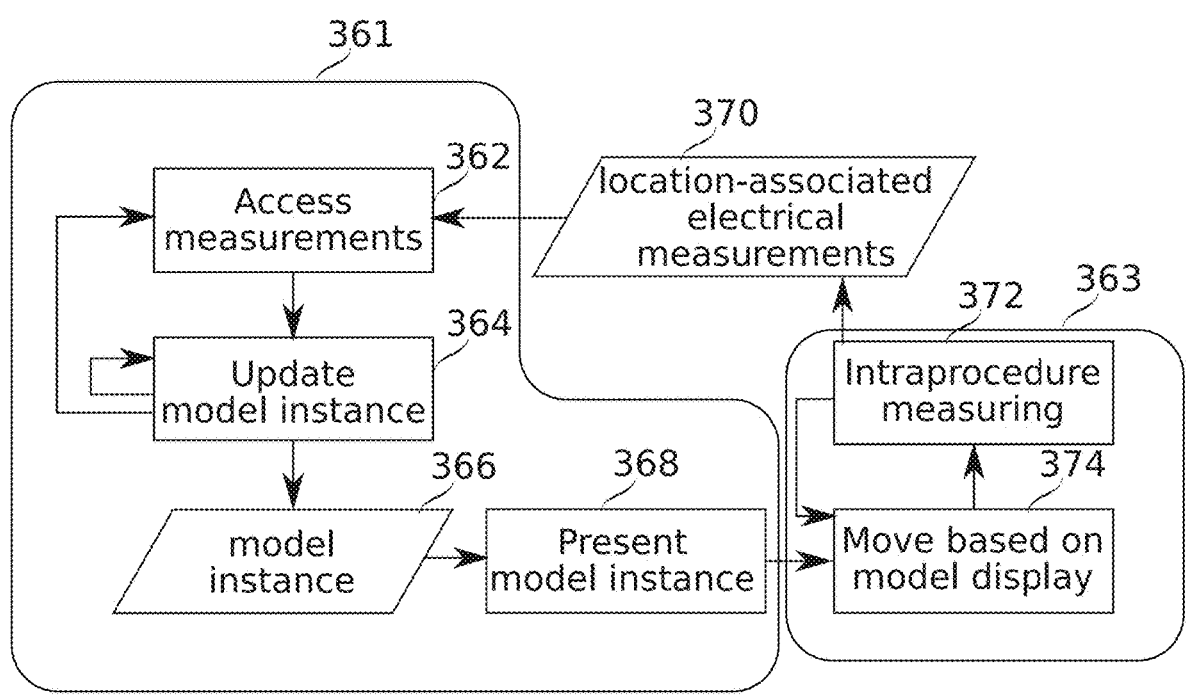
FIG. 3C schematically represents guidance of an intralumenal surgical tool, according to some embodiments of the present disclosure.

Reference is now made to FIG. 3C, which schematically represents guidance of an intralumenal surgical tool, according to some embodiments of the present disclosure.

Block 361 depicts operations of a computer-implemented modelling system, and block 363 depicts operations guided by the modelling system, which in turn provide inputs back to the modelling system.

At block 362, the modelling system accesses location-associated electrical measurements represented by data block 370; for example as described in relation to blocks 210, 220, 230, and/or block 235 of FIG. 3A; and/or block 325 of FIG. 3B.

At block 364, the model instance is updated, for example including operations as described in relation to blocks 320, 330, 340, 350, and 360 of FIG. 3B and/or in relation to FIG. 1B.

It is noted that block 364 may form a loop within itself, wherein the model instance is updated more than once (e.g., as part of a gradient-descent error minimization function), optionally without one or either of accessing new measurements or outputting a new version of the model instance. A second loop returns to access (new) measurements 362 so that they can be incorporated into additional model updating. It should be understood that the two loops may operate in the alternative, or asynchronously.

The model instance itself (the version available for use in presentation) is represented as data block 366. Optionally, this is the version which is directly operated on as block 364 performs its updating function; or it may be a copied and/or post-processed model instance which is updated less often than a version of the model instance internal to the operations of block 364.

At block 368, in some embodiments, the model instance is presented. Presentation may comprise showing on a computer display a 3-D image calculated by a computer processor using parameter values of the model instance.

In some embodiments, the operations of block 361 are performed iteratively at the same time as a procedure which uses the model instance is being performed. At block 374, in some embodiments, movement of a surgical implement (e.g., surgical implement 700, illustrated in FIG. 7A, configured with an electrode and/or for use as an electrode) is carried out based on a position of the tool shown in the model instance. The tool may also be a non-electrode tool, the position of which is known by a non-electrical measurement-based method.

In the case of a surgical tool also equipped to make electrical measurements of the type entered into block 370, the movement at block 374 may have the effect of bringing the tool into a position at which new intra-procedure measuring can be performed (at block 372). The new measuring produces new measurements to add to data block 370, which can then feed into the operations of block 361.

There is thus a synergistic technical effect which can be achieved or enhanced when the cycle of measuring, model instance updating, moving, and measuring again can be performed in real time (e.g., at least one update cycle per two seconds, or one second), and preferably smoothly in real time (e.g., at least 5, 10, 15, 20, 25 or 30 or more update cycles per second). Before a certain region is even visited, the parametric model updated within block 361 may still show potential targets with sufficiently accurate size and/or position to guide the movement of block 374.

As a probe (e.g., an electrode-equipped surgical tool) moves to approach a target area and/or as it remains there, the parametric model may be gradually refined. Measuring may performed more intensively in some zone represented by the model instance, perhaps simply because that is a place of particular interest for a current procedure. That leads to the region being better characterized (in terms of electrical measurements); and that potentially allows the model updating of block 361 to produce a model which more accurately indicates the region being visited.

Figure 4:
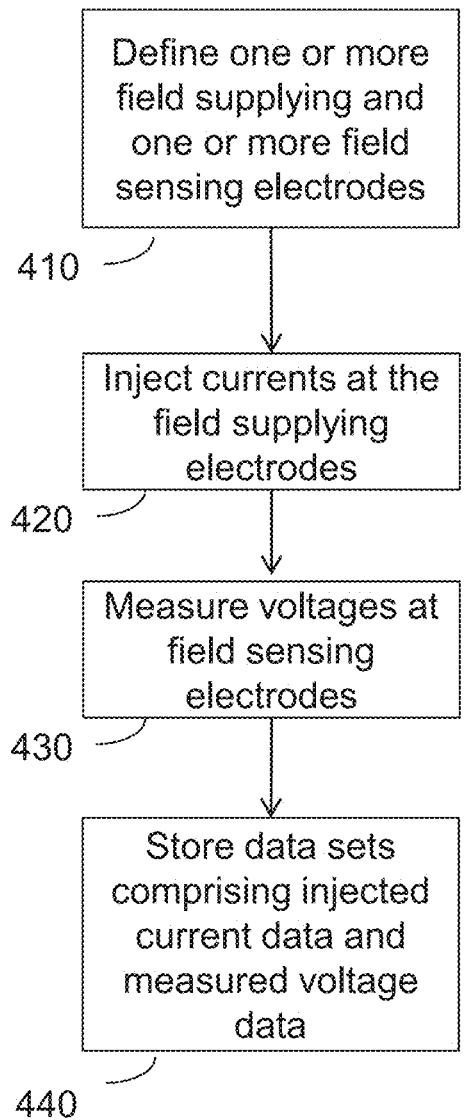
FIG. 4 depicts a flowchart for a method of accessing a measured voltage data according to some embodiments of the present disclosure.

Reference is now made to FIG. 4, which depicts a flowchart describing a method comprising operations for measuring voltage data using voltages sensed by field-sensing electrodes in response to electric fields supplied by field-supplying electrodes disposed on one or more tools in or near the structure. The operations described and/or depicted in this flowchart may be performed, for example, as a precursor to the operations of blocks 210-240 of FIG. 12 in order to generate the measured voltage data accessed at block 210. Operations may alternatively occur at a separate point in time to obtain the measured voltage data which is then stored, for example in a computer system memory. The measured voltage data may then be accessed at a later time when the method of FIG. 3A is carried out.

At block 410, in some embodiments, one or more field-supplying and field-sensing electrodes are defined. As discussed above, the electrodes are disposed on one or more tools positioned relative to the structure such that electric fields supplied by the one or more field-supplying electrodes interact with the structure and the one or more field-sensing electrodes are able to sense the resulting voltage at the respective positions of the field-sensing electrodes. The one or more tools carrying the electrodes may already be positioned relative to the structure, and in particular in the vicinity of the structure, or block 410 may involve positioning the tool in or near the structure. For example, if the electrodes are disposed on one or more catheters, operations of block 410 involve inserting the catheter(s) in the relevant portion of the body, for example a heart chamber. In other examples, some of the electrodes are surface electrodes, for example surface pads configured to be placed on the surface of the body. In these examples, block 410 may involve placing the surface pads on the body, optionally at predetermined locations on the body. For example, surface pads may be placed in specific locations on the body, such as having one electrode placed on the chest just above the heart, one on the back, and two at the two sides of the patient. In some embodiments, a wearable garment with electrodes is worn on the body.

The positions of each electrode with respect to the tool on which it is disposed, or with respect to a reference frame may be known. In some embodiments, the reference frame is fixed relative to the tool on which the electrodes are disposed, or may be fixed relative to the body. It should be noted that the reference frame need not be fixed relative to any known entity such as a tool or the body, but may be any reference frame that is common for all of the electrodes. In particular, if measurements are acquired as electrodes are moved to different positions, a common reference frame for all of the electrodes at each respective position can be determined, and the positions of the electrodes are defined in this reference frame. Thus, the positions of each electrode may be known relative to one another. Defining the one or more field-supplying and field-sensing electrodes comprises assigning each of the electrodes as a field-supplying or field-sensing electrode. Each electrode is therefore assigned as a field-supplying electrode at which currents are injected, or a field-sensing electrode at which voltages are sensed. In some embodiments, one or more electrodes may instead be assigned as a ground electrode. The assignment may be based on a specific excitation scheme which defines the magnitude, duration and frequency of current applied at the field-supplying electrodes, and further defines which electrodes are to function as field-supplying electrodes and which electrodes are to function as field-sensing electrodes (and optionally, which electrodes are to function as ground electrodes). Some or all of the electrodes disposed on the tools may be assigned. It would be appreciated that any given electrode may be assigned as a field-supplying electrode for a first frequency and a field-sensing electrode for one or more other frequencies, optionally, different from the first. In other words, an electrode may function as both a field-supplying and field-sensing electrode simultaneously, transmitting (i.e. supplying an electric field) at a first frequency and simultaneously receiving (i.e. sensing an electric field) at all other frequencies, and optionally also at the first frequency. Thus, in a system with multiple electrodes, each electrode may transmit at a unique frequency, which may be sensed by all the other electrodes in the system.

In a system of multiple electrodes according to some embodiments, a series of different frequencies may be used, each electrode supplying an electric field at one of those frequencies in the series. In some examples, the difference between adjacent frequencies in the series is 800 Hz. It would be appreciated that the different between adjacent frequencies must be sufficiently large to avoid cross-talk between the electric fields generated at different frequencies. At the same time, the difference between adjacent frequencies may need to be sufficiently small in order to provide a sufficient number of frequencies in a given frequency band.

The method, in some embodiments, further comprises injecting currents and measuring voltages; respectively at blocks 420 and 430. Specifically, at block 420, currents are injected/applied to the assigned field-supplying electrodes in accordance with the excitation scheme, for example at a given magnitude, frequency, and relative phase, and the results are stored at block 440. At block 430, the assigned field-sensing electrodes sensed voltages resulting from the electric fields excited by the filed supplying electrodes. The voltages sensed by the field-sensing electrodes is then recorded as measured voltage data, which, along with the applied current data are then stored at block 440; for example in a memory of a computing system, for use in the methods described with reference to FIGS. 3A, 3B, and 3C.

The operations of blocks 420 and/or 430 may be repeated after one or more of the electrodes are moved to a new position relative to the structure. For example, the measured voltage data may comprise voltages measured using a one or more field-sensing electrodes each at a plurality of different positions at different points in time.

Figure 5:
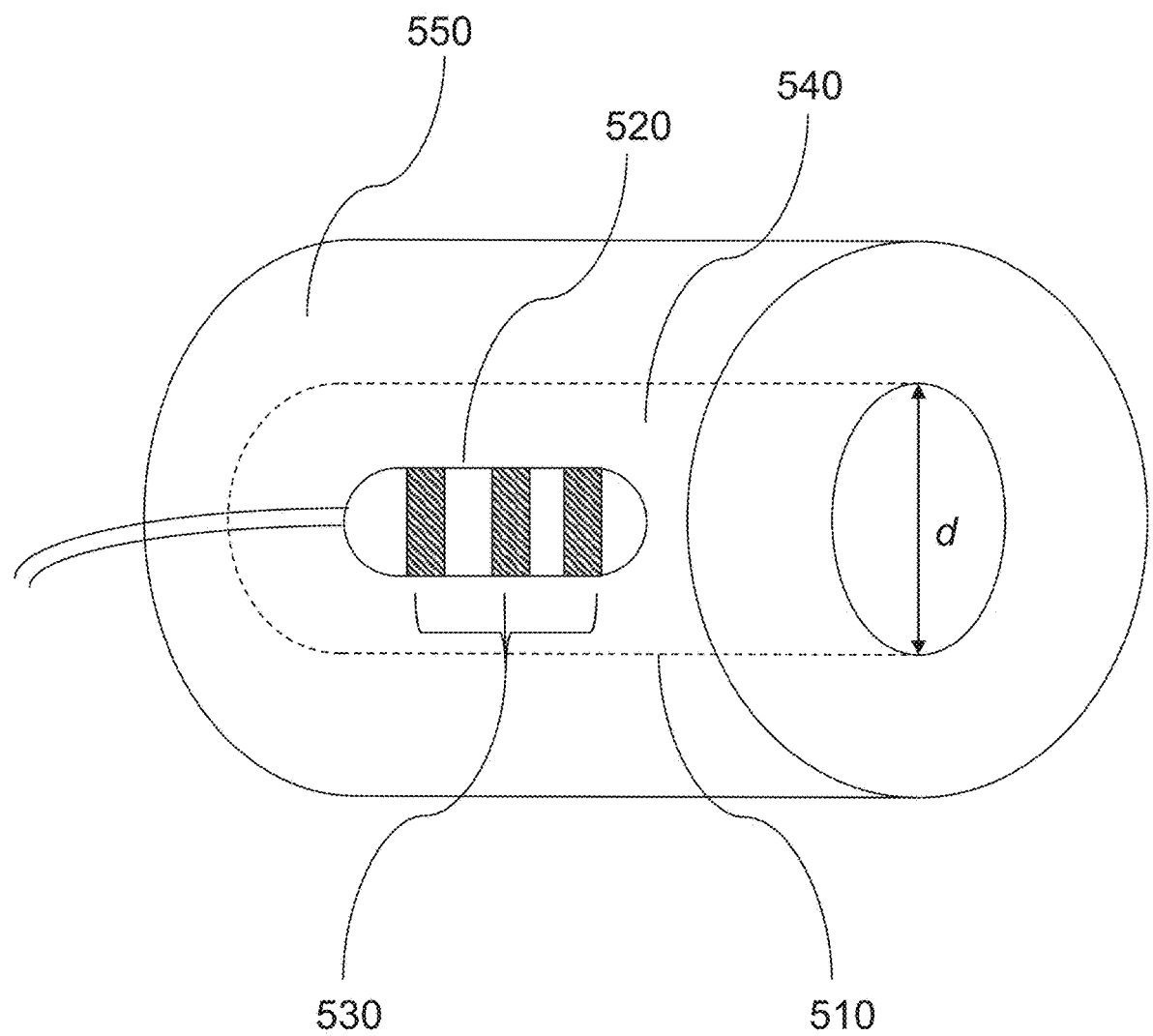
FIG. 5 is a schematic diagram of a blood vessel useful in understanding some embodiments of the present disclosure.

FIG. 5 illustrates a structure in a human or animal body, as may be measured according to some embodiments of the present disclosure. The illustrated structure 510 is, for example, a blood vessel or a portion of a blood vessel. It should be appreciated that in other examples the structure may be a different body part inside the body, for example a vein, an artery, an organ, a heart chamber wall, or a portion thereof. The model of the structure is characterized by a parameter representing the diameter of the blood vessel 510. In other words, the model models the blood vessel or portion of the blood vessel 510 as a cylinder, wherein the diameter of the cylinder is defined by a parameter d. In this embodiment, methods of the present disclosure may therefore be used to find the diameter of the modelled blood vessel (or portion thereof), assuming that the blood vessel is cylindrical. In practice, the blood vessel may not be perfectly cylindrical and thus it may be considered that methods of the present disclosure are used to estimate a diameter of the blood vessel.

Other parameters may be part of the model too, optionally as fixed parameters, or free parameters (which may be free only within certain constraints, e.g., a range of plausible values). The other parameters may include, for example, dielectric properties of the blood, and/or additional geometric properties, such as the thickness of the blood vessel wall and/or outer diameter of the blood vessel.

Referring back to FIG. 12 and specifically block 210 discussed above, the measured voltage data is measured using electrodes 530 disposed on one or more tools 520, such as a catheter, positioned inside the blood vessel 510. In the illustrated example, the tool 530 comprises both field-supplying electrodes that generate an electric field as a result of currents applied to those electrodes, and field-sensing electrodes that sense a voltage as a result of the generated electric field interacting with the blood vessel. Then, at block 230, the position data maybe indicative of the location of the electrodes in a reference frame, for example a reference frame common for a plurality of different positions of each electrode (e.g. as the tool moves along the blood vessel). With reference to optional block 235, the dielectric data may be accessed which defines a value of a dielectric property of the material inside the blood vessel 540 (i.e., the blood inside the blood vessel) and further defines a value of the dielectric property of the tissue forming the blood vessel wall 550. In other words, the dielectric data provides a distribution of values for a dielectric property associated with the structure, where there is a first value for the material 540 within diameter d and a second dielectric value for the material 550 outside of diameter d. Corresponding model parameters (representing these dielectric properties of the blood vessel (model parameters defining a dielectric property of the volume of material inside the blood vessel and further parameters defining a dielectric property of the volume of material outside the blood vessel) may be fixed based on this dielectric data. Alternatively, if predefined dielectric data is not available, the values of these model parameters may be determined in addition to determine the diameter of the blood vessel.

It would be understood from the laws of electromagnetism that the diameter of the blood vessel, i.e. the distance from the electrodes at which there is a step-change in a dielectric property such as conductivity, can affect the resulting voltages sensed by the field-sensing electrodes in response to the electric fields supplied by the field-supplying electrodes. For instance, for a given current applied at an electrode at a given distance, an electrode closer to the circumference of the blood vessel (where the step-change occurs) will give a different voltage measurement compared to an electrode further from the circumference. Using sets of voltage measurements at given field-sensing electrodes based on currents applied at given field-supplying electrodes, it is therefore possible to model the diameter of the blood vessel, as well as the radial position of the tool within the blood vessel, using the methods described herein.

Figure 6:
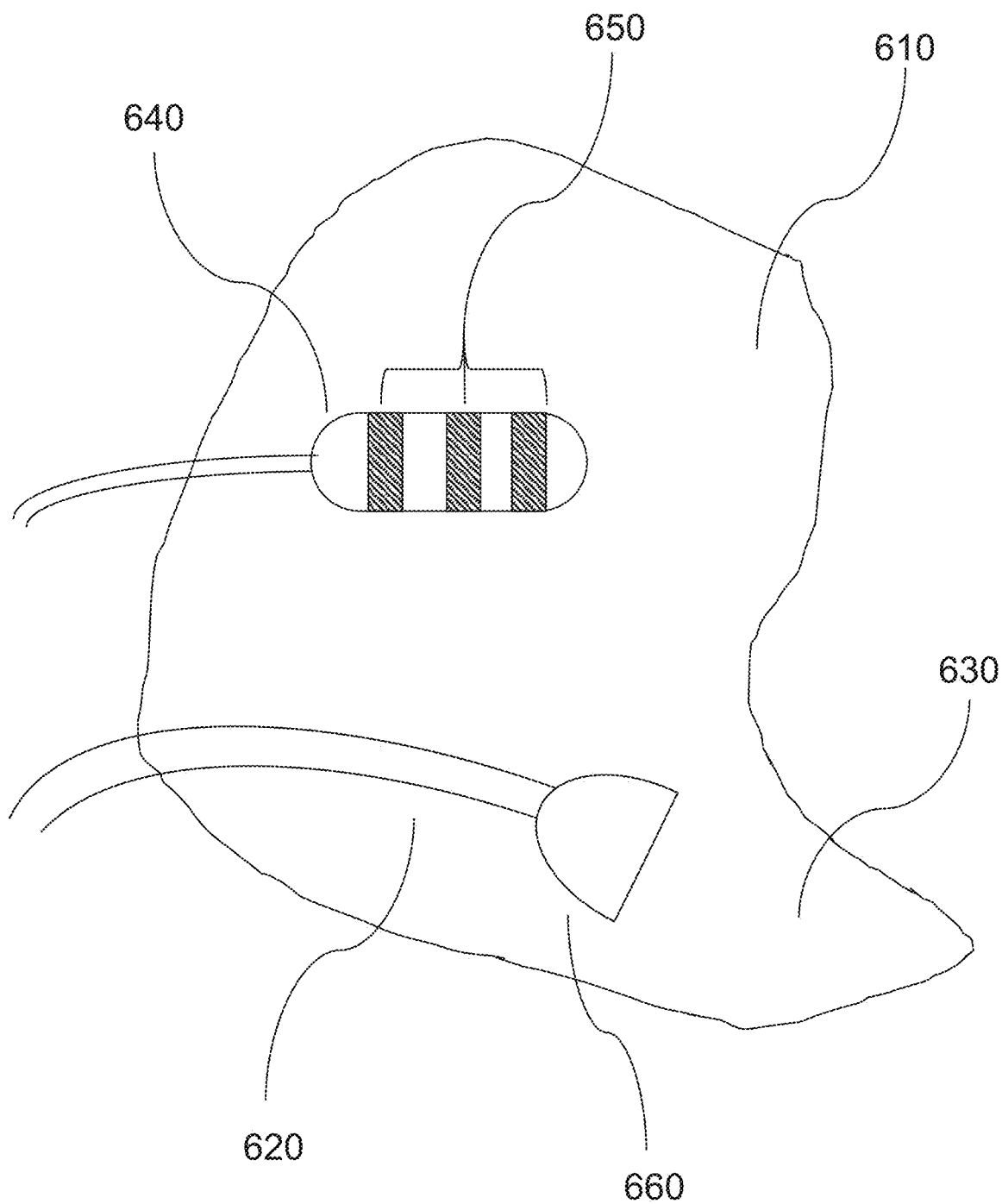
FIG. 6 is a schematic diagram of a surgical implant useful in understanding some embodiments of the present disclosure.

FIG. 6 illustrates a structure in a human or animal body according to some embodiments of the present disclosure is shown. The structure is a surgical implement 620 situated inside the body. The surgical implement may be temporally situated inside the body, for example the surgical implement may be a surgical instrument used during a surgical procedure, such as an endoscopic instrument. The surgical implement, in some specific examples, comprises an implant such as a Watchman™ left atrial appendage occluder configured to be implanted in a portion of the heart chamber such as the left atrial appendage to prevent blood clots formed in the appendage from reaching the left atrium or other portions of the heart. Other examples of surgical implants to be implanted in the heart to which embodiments of the present disclosure relate include an atrial septal defect occluder, a patent foramen occluder, a ventricular septal defect occluder, aortic valve replacement or repair device, mitral valve replacement or repair device, and a tricuspid valve replacement or repair device.

In the embodiment illustrated in FIG. 6, the model of the implant is characterized by a parameter or parameters representing the position and/or the orientation of the implant relative to one or more tools 640 carrying electrodes 660. In some embodiments, the tool or tools 640 may be a Lasso™ catheter, pig tail catheter, basket catheter, or spiral catheter. Optionally, the position of the tools are known relative to the body, or relative to a reference frame independent of the body. The position and orientation of the implant may be modelled relative to the tools or relative to heart chamber 610 of the body, and more specifically relative to portion 630 of the heart chamber where the implant is to be placed. The position and/or orientation of the implant may also be modelled relative to an earlier position and/or orientation of the tool, that is, independent of the body or any other fixed entity.

Referring back to block 210 of FIG. 3A, in the example illustrated in FIG. 6, the measured voltage data is measured using electrodes 650 disposed on a tool 640, such as a catheter, positioned inside the same heart chamber as the surgical implement 620. It would be appreciated that more than one tool may be used, each tool carrying only field-supplying electrodes, field-sensing electrodes, or a combination of both. In some embodiments, the electrodes are disposed on two tools positioned in the chamber 610 and on opposite sides of the surgical implement. In other embodiments, one or more tools may instead be positioned in adjacent heart chambers (not shown) or even in another region in the body. It would be appreciated that in any case, the one or more tools on which the electrodes are disposed are separate and distinct entities to the surgical implement that is modelled. The model of the surgical implement may include parameters that represent the position and/or orientation of the surgical implement relative to the one or more tools, and thus the model models the relative position and/or orientation between the surgical implement and the tool. In the illustrated example, the tool 640 comprises both field-supplying electrodes that generate an electric field as a result of currents applied to those electrodes, and field-sensing electrodes that are used measure a voltage as a result of the generated electric field interacting with the surgical implement 620. Then, at block 230, the position data maybe indicative of the location of the electrodes in a reference frame, for example a reference frame common for a plurality of different positions of each electrode (e.g. as the tool moves along the blood vessel). Alternatively, the position data maybe indicative of the location of the electrodes on the tool, for example the order of the electrodes, their position relative to one another and/or their position relative to a fixed point on the tool, and the position of the tool may be defined relative to a reference frame fixed relative to the body, such that the position of the electrodes relative to the body can be obtained. With reference to optional block 235, the dielectric data may be accessed which defines a value or values of a dielectric property of one or more portions, or the whole of the surgical implement, and more specifically the implant 660. Corresponding model parameters (representing the dielectric properties of respective portions of the implement) may be fixed based on this dielectric data. Alternatively, if predefined dielectric data is not available, the values of these model parameters may be determined in addition to determining structural properties of the implant (such as position and orientation).

In some examples, the implant is an expanding implant, such as a Watchman implant. In these examples, the model may include parameters that model a degree of expansion of the implant, a size, shape and/or some other dimension of the implant. For example, the model parameters may include a parameter representing a diameter of a portion of the expanding implant. The model of the structure may model such additional structural properties of the implant in addition to the position and/or orientation of the implant. The Watchman implant comprises a nitinol wire frame with defined values of various dielectric properties, such as conductivity. These dielectric properties of the implant may be included in accessed dielectric data or may be modelled in addition to the structural properties of the implant. The implant may comprise further known materials that also have defined dielectric properties that are included in the accessed dielectric data or are modelled.

It would be understood from the laws of electromagnetism that the distance between the catheter 640 carrying the electrodes 650 and the expanding implant 660 will affect the resulting voltages sensed by the field-sensing electrodes in response to the electric fields supplied by the field-supplying electrodes. The expanding implant is not an infinitesimal point with a given dielectric property (provided by the dielectric data), nor is the expanding implant a sphere with a uniform value of a dielectric property. Accordingly, the specific position and orientation of the implant relative to the catheter will affect the measured voltages, as will the degree of expansion of the implant. Using sets of voltage measurements at given field-sensing electrodes based on currents applied at given field-supplying electrodes, it is therefore possible to model the position and orientation of the implant relative to the tool, as well as other geometrical properties such as the degree of expansion of the implant, using the methods described herein.

Figure 7A:
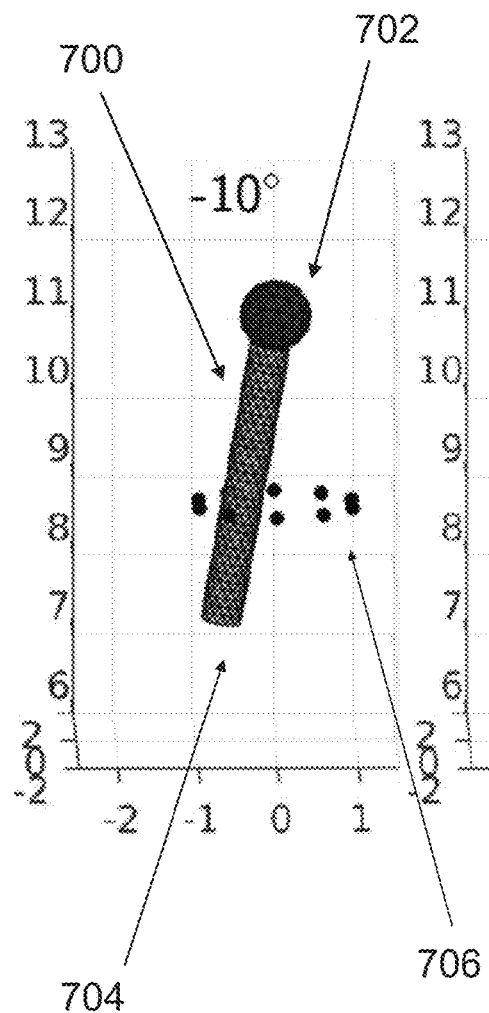
FIGS. 7A-7C are schematic diagrams of a surgical implement useful in understanding some embodiments of the present disclosure.
Figure 7B:
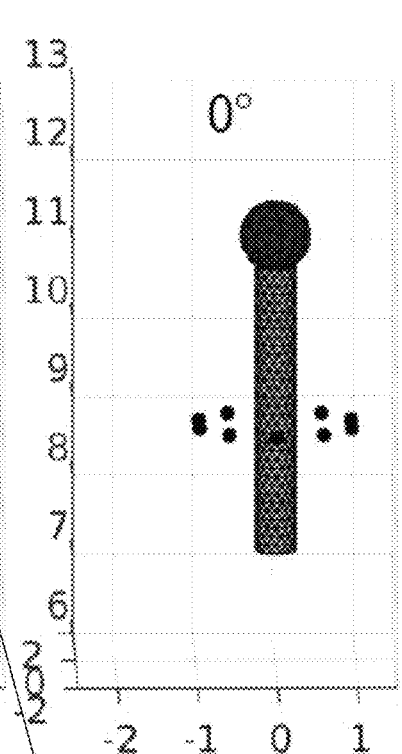
Figure 7C:
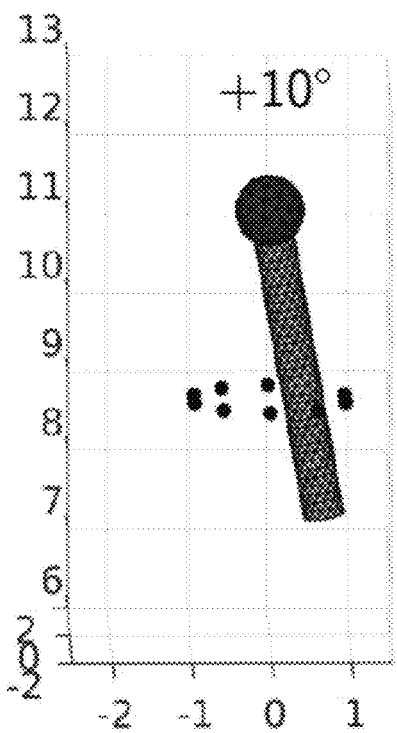

FIGS. 7A-7C show diagrams illustrating a structure in a human or animal body. In this example, the structure is a surgical implement 700 comprising a metallic portion 702 protruding from a sheath 704. The implement is surrounded by electrodes 706 that are disposed on a deck-polar catheter (not shown). It can be seen that the orientation of the implement with respect to the electrodes is different in each of the FIGS. 7A, 7B, and 7C.

Figure 7D:
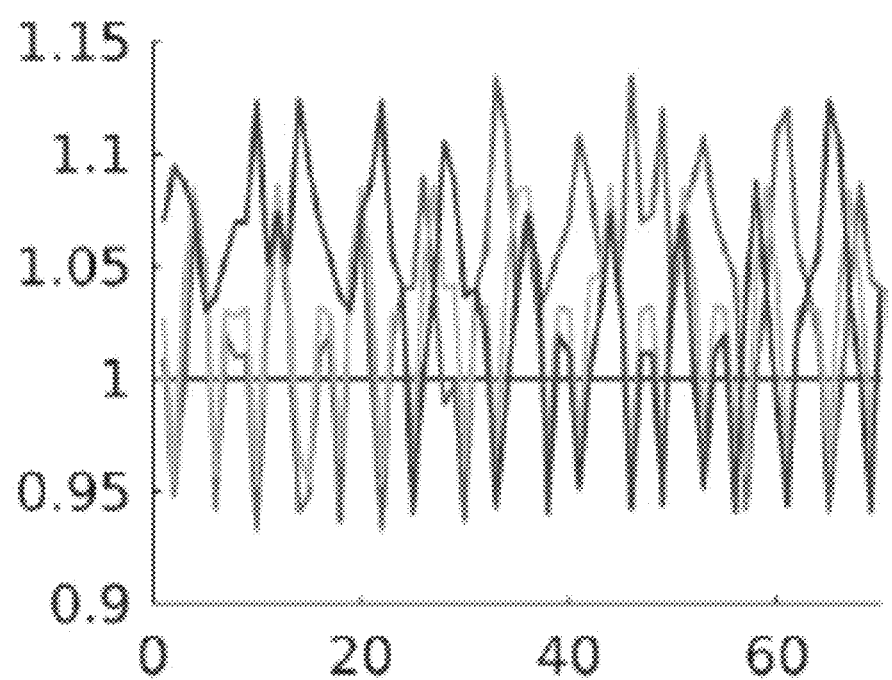
FIG. 7D is a graph depicting model voltage measurements for different orientations of the surgical implement depicted in FIGS. 7A-7C.

With reference to FIG. 7D, model voltages that represent voltages expected to be measured from voltages sensed by the field-sensing electrodes of the electrodes 706 in response to currents applied at field-supplying electrodes of the electrodes 706 are shown for each orientation of the implement. Each line depicted on the graph of FIG. 7D represents model voltages for a different orientation of the model of the surgical implement with respect to the arrangement of electrodes and corresponds to one of the FIGS. 7A-7C. It can be seen that the model voltages depend on the orientation of the implement, due to the interaction of the implement with the electric field supplied by the field-supplying electrodes. Given the dependency of the voltage on the orientation, as indicated by the modelled voltages, methods of the present disclosure can be used to determine the orientation of the implement with respect to the electrodes. Referring back to FIG. 3A, in this embodiment, the model parameters determined at block 240 represent an orientation of the implement relative to the electrode arrangement, and the values of the parameters may be determined so as to minimize an error between measured voltages and the model voltages calculated based on the parameter values.

In another embodiment of the present disclosure, the modelled structure may be a heart or portion of a heart, such as a heart chamber, and the model may model the heart or heart portion as well as the surrounding region. In an exemplary embodiment, the modelled structure is a wall of a heart chamber. The model parameters include a parameter representing thickness of the wall of the heart/heart chamber, and may further include a model parameter or parameters that represent the conductivity or other dielectric property of the medium outside of the heart wall, for example, neighboring the heart wall from its other side, that is, other than the side at which the electrodes are. The model may also further include a parameter or parameters defining the conductivity or other dielectric property of the heart wall itself. Methods of the present disclosure can be used to determine values of the thickness of the heart chamber, the conductivity (or other dielectric property) of the medium outside the heart/heart chamber, and/or the conductivity (or other dielectric property) of the heart wall of the heart/heart chamber. These methods may involve applying currents using field-supplying electrodes disposed on a catheter (e.g., a Lasso catheter, basket catheter, spiral catheter, or pig tail catheter, for example) contacting the inside of the heart wall, and measuring voltages using field-sensing electrodes disposed on the catheter. For example, each electrode of the catheter may act as a field-supplying electrode at a unique frequency, and each other electrode acts as a field-sensing electrode for that frequency. In other words, all of the field-supplying electrodes and all of the field-sensing electrodes may be disposed on the catheter disposed inside the heart chamber, or more generally inside the body cavity. This is an example of an embodiment where the one or more tools inside the body on which the field-supplying electrodes are disposed may consist of a single catheter disposed inside the body cavity that carries all of the electrodes.

Embodiments wherein the field-supplying and the field-sensing electrodes are inside the body, and particularly when electrodes that sense a certain field are on the same tool as the electrodes supplying the certain field (e.g., embodiments where the one or more tools, on which the field-supplying electrode are disposed, consists of a single catheter) are particularly advantageous because they allow making voltage measurements using field-sensing electrodes that are very close to the field-supplying electrodes so that the resulting measurements are affected less by long-range noise (e.g. noise as a result of a patient's thorax moving, due to breathing) since the electrodes are in close proximity (e.g. less than 5 cm away from one another) and, depending on the specific type of catheter used, they may be in a fixed position relative to one another. With all of the electrodes disposed on a single catheter, the measurements made using the field-sensing electrodes are 'local', since they are made as a result of an electric field produced by field-supplying electrodes that are close to the field-sensing electrodes. This means that the measured voltages are a result of the electric field interacting with tissue local to the electrodes. Therefore, distanced tissues and events have less of an impact on the resulting measurements. Additionally, in certain embodiments the catheter carrying all of the electrodes may be positioned very close to the structure of interest (e.g. the particular part of a heart chamber wall that is to be modelled), and possibly contacting the structure (e.g. contacting the wall). This can also improve the accuracy of measurements by reducing the effect of noise.

Therefore, in the embodiments described above and below, it is advantageous for field-supplying and field-sensing electrodes to be disposed on the same disposed inside the body cavity, or at least on multiple catheters very close together and very close to the structure of interest inside the body cavity. Other arrangements of the electrodes, for example any other arrangement of one or more tools disposed inside the body and optionally one or more surface electrodes, may also be used.

In some embodiments, methods disclosed herein may be applied to models of a heart wall (or more generally any surface inside a body) in terms of the heart wall thickness, wall dielectric properties, and/or dielectric properties of a medium adjacent to the wall at its other side. Applying the methods to such models may allow to distinguish between walls of different portions of the heart wall, to the extent these differ from each other by measurable differences in respective properties.

As a consequence of modelling such parameters of the heart wall or of the other side of the heart wall, different heart chambers or different portions of the same heart chamber may be distinguished from one another by their respective wall thicknesses and/or conductivities. It is therefore possible to determine from the values of these model parameters which heart chamber or which portion of a heart chamber the catheter is contacting. It is also possible to determine which heart chamber or portion of a heart chamber the catheter is being contacted by modelling a dielectric property of the medium on the other side of the wall. In particular, the conductivity of the medium on the opposite side (on the outside of the heart chamber) can be used to distinguish between a heart chamber wall bordering with the esophagus (with a generally high impedance due to the air in the esophagus) and a heart chamber wall bordering other heart chambers (with a lower impedance due to the blood in those chambers).

In the above examples, the model parameter values may be determined based on a catheter contacting the wall, such that the catheter is 'flush' to the wall (i.e. in the context of the electrodes lying in a plane, such as in the example of a Lasso catheter, that electrode plane and the plane of the wall are parallel and the electrodes are in contact with the wall). Alternatively, in practice the catheter may not be perfectly 'flush' to the wall, leaving an angle between the respective planes of the wall and the electrodes. Therefore, in some examples, an additional model parameter may represent the angle between the two planes. In some embodiments, the angle is an angle between the plane of the electrodes and the normal to the plane of the wall.

In some embodiments, different electrodes disposed on the same catheter may be contacting different walls of the heart (or other cavity inside the body). In these embodiments, is possible to gather information (such as wall thickness or other information as described above) on each wall separately while obtaining measurements from the respective electrodes contacting each respective wall at the same time, or on one wall each time.

In a further embodiment involving a wall and more specifically a heart wall, a catheter (e.g., a lasso catheter) may be disposed at a distance from the wall. In this embodiment, the model of the wall may include model parameters representing a position and/or orientation of the wall relative to the catheter. In more detail, the model parameters may include a parameter representing the distance between the catheter and the wall, and a parameter representing the angle between the respective planes of the catheter (when the catheter electrodes lie in a plane, such as in the case of a Lasso Catheter or a spiral catheter) and the wall. In embodiments where a lasso catheter is used, the distance may be defined as the distance between the center of the lasso catheter (the center of the loop portion 1120 of the lasso catheter in FIGS. 11A and 11B) and the wall. The angle may be defined as the angle between the plane defined by the loop portion of the lasso catheter and the normal to the plane of the wall. These two model parameters define a vector with a direction along the normal to the plane of the wall and a magnitude of the distance between the wall and the catheter.

Methods disclosed herein can be used to find the vectors between the plane of a wall and the lasso catheter (or other suitable catheter) for multiple wall portions, each at different respective distances and at different respective angles to the catheter. In particular, voltages measured using the electrodes disposed on the catheter may be fit to a model comprising multiple planar wall surfaces, each having a different angle and distance relative to the catheter. The model comprises model parameters representing the distance and angle to each plane. The values of the parameters are then evaluated for each plane based on the measured voltages and using the disclosed methods. Based on the parameter values and the resulting normal vectors for each plane, a model of a curved surface can be built from the multiple planar surfaces.

In some embodiments, instead of fitting multiple planar walls to measured data, a mesh of polygons may be used to model the surface of the wall. Each polygon in the mesh may have its own one or more respective parameters, such as 3-D coordinates of the corners of the polygon, or vectors representing a relative angle and distance between the catheter and the polygon. In any event, the number of model parameters should not be larger, and is preferably smaller, than the number of measurements.

The above examples relating to modelling a heart wall (or any other wall of a body cavity) can also be carried out using a roving catheter instead of a stationary catheter (either contacting the wall or disposed away from the wall). Specifically, measured voltage data may be obtained using a roving catheter configured to move around within the body cavity and take measurements at different locations within the cavity. Position data corresponding to the measurements taken at different locations can be obtained using known measurement-to-location techniques, for example, techniques described herein and as disclosed in WO2019034944A1, or other suitable techniques available to the skilled person. The above examples relating to modelling the thickness, and dielectric properties of the wall and medium on the other side of the wall may be carried out using a roving catheter instead of a stationary catheter contacting to or positioned away from the wall. As discussed above, all of the field-supplying electrodes and field-sensing electrodes may be disposed on the roving catheter, to achieve the benefit of reducing the effect of noise on the measurements (since the field-supplying electrodes are very close to the field-sensing electrodes).

The above examples relate to modelling a surface of a heart wall or more generally any surface inside a body. Where reference is made above to a heart wall, it would be understood that the above embodiments may apply more generally to any structure comprising an internal tissue surface of a body cavity. That is, the above embodiments in which the modelled structure is a heart wall are non-limiting illustrative examples. In other embodiments, the modelled structure may be leaflet in a heart, or the surface of the heart leaflet may be modelled. More specifically, the above embodiments may apply to a tricuspid or mitral leaflet (also known as a tricuspid or mitral valve) of a heart.

Generally, the modelled structure may be or may comprise a surface of a portion of a body, for example an interior or exterior surface of an organ or portion of an organ, or the interior of any other body cavity.

The following embodiments relate to modelling any general structure inside a body, and to use modelling with a selection of candidate models to improve model fit and/or classify body structures.

In some embodiments, the present methods can be used to classify the type of structure according to the type of model that provides the best fit between measured voltages and calculated voltages for that model. In this embodiment, a structure in the body can be modelled using a plurality of different types of candidate model structure, each candidate model structure being characterized by different model parameters.

For each of the candidate models, computed voltages based on those models can be 'fit' to measured voltages (e.g., comparison with measured voltages to determine an error, update the model parameters using an optimization process and repeating). A comparison between fit of the different models to the measured voltages can give an indication of the suitability of that model for modelling the structure, and hence can give an indication of the geometric properties (i.e. the general shape) and even type of structure being modelled. For example, the magnitude of the error between computed and measured voltages, or the time/number of iterations required to converge on model parameter values that give rise to an error below a threshold, may indicate how suitable any given model is for modelling the structure.

Thus, the most suitable model from a plurality of candidate models can be found for accurately modelling the structure, and based on which model is the most suitable model, the type of structure being modelled can be classified.

As an illustrative example, the structure may be a blood vessel. Blood vessels in the body are generally cylindrical structures and hence it is appropriate to model the blood vessel as a cylinder, as described in relation to FIG. 5. However, in reality it may be the case that a blood vessel is not cylindrical but is instead frustoconical and resembles a truncated cone, in which case a cylindrical model is not suitable for modelling the blood vessel and for determining properties of the blood vessel.

Some embodiments allow the shape of a blood vessel to be classified (i.e. whether the blood vessel more closely resembles a cylinder or a truncate cone) by modelling the blood vessel as both a cylinder and a truncated cone and determining which model fits the measured data best. Each of the cylinder model and truncated cone models are different types of model defined different respective model parameters. Voltages measured inside the blood vessel can be used in the disclosed methods to find the values of the model parameters of both the cylinder and truncated cone models. The error signal computed for each model, or the number of iterations required to converge on parameter values which give rise to error signals below a threshold value, may serve as an indication of the suitability of the model for modelling the blood vessel. For example, if the cylinder model has a lower error signal or takes less time to converge on accurate parameter values compared to the truncated cone model, then modelling the blood vessel as a cylinder may be more suitable than modelling the blood vessel as a truncated cone. It may also be the case that one or more types of model do not converge at all, in which case it would be understood that such models are not suitable for modelling the structure. By determining the best fit or by eliminating one or more candidate models if parameter values do not converge, it is possible to determine the most suitable type of model (among the candidates) for modelling the blood vessel, and thus infer the general shape of the blood vessel from that model. In other words, based on which model is most suited to modelling the structure, the type of structure can be classified from the candidate model structure (in this example whether the blood vessel is cylindrical or frustoconical).

In another illustrative example, a heart chamber wall may be modelled by a plurality of candidate models, a first being a flat surface, a second being a portion of a cylindrical surface and a third being a portion of a spherical surface. In addition, different candidate models may comprise different features, such as the presence or absence of an opening (i.e. a hole) in the wall. Thus, the disclosed methods can be used to determine whether the wall should be modelled as a flat, cylindrical or spherical surface, and whether there exists an opening in the heart chamber wall. In other words, the wall can be classified as a flat, cylindrical or spherical surface, and can be classified as comprising an opening or not. A practical application of the latter is to determine whether the portion of the heart chamber wall being modelled has such an opening, such as a pulmonary vein ostium.

Thus, for any given structure in a body, a plurality of different candidate models may be 'tested' to see whether those models can be fit to the measured voltages. This allows one to find the most suitable model out of the plurality of candidate models that may lead to the most accurate results for the values of the model parameters. In turn, the structure being modelled can be classified as the candidate model structure of the most suitable model (e.g. blood vessel structure classified as a cylinder or cone, heart wall classified as flat, spherical or cylindrical).

Figure 8:
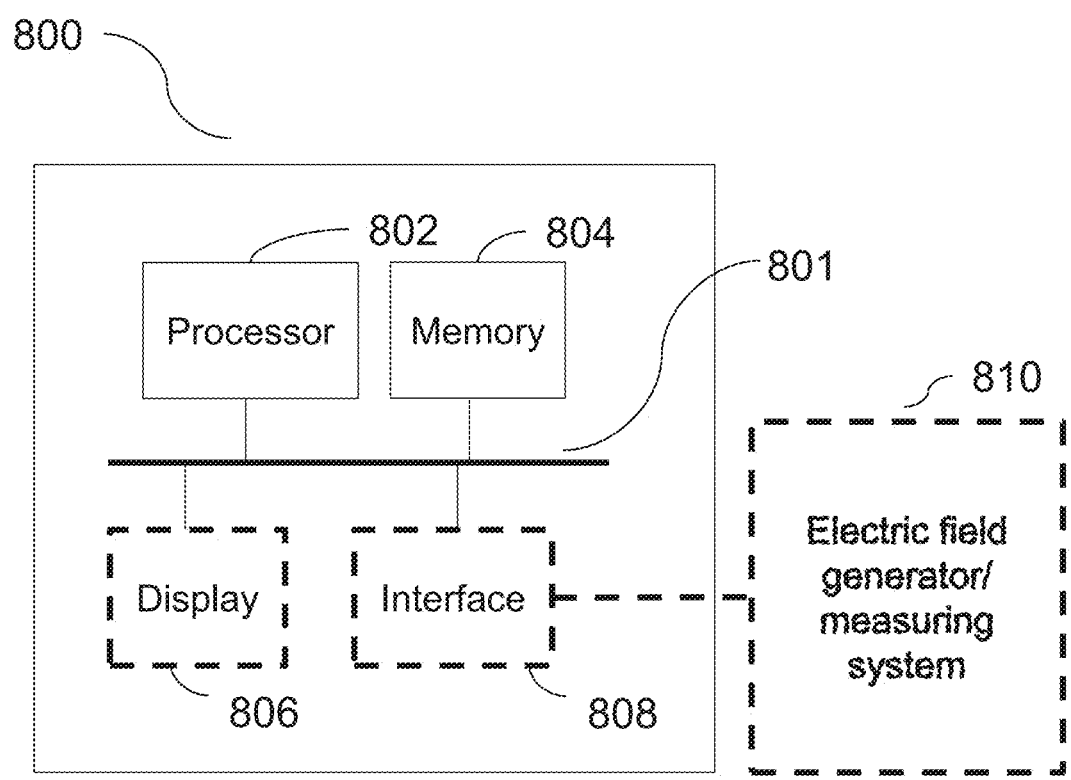
FIG. 8 is a schematic block diagram of a computer system configured to perform methods of the present disclosure.

With reference to FIG. 8, a system 800 for carrying out any one or more of the may be a computing device 802 within which are a set of instructions, for causing the computing device to perform any one or more of the methodologies discussed herein. The computing device may be a personal computer (PC), a tablet computer, a cellular telephone, a web appliance, a server, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein. For example, the apparatus may be configured to carry out any or all of the methods discussed herein.

The system 800 comprises at least a processor 802 configured to carry out a method according to the present disclosure, for example the method described above with reference to FIG. 3A or FIG. 3B. The system further comprises a memory 804 configured to store information for use in the methods of the present disclosure. For example, the memory 804 is configured to store voltage data for the voltages sensed by the field-sensing electrodes and corresponding current data for the currents applied at the field-supplying electrodes, as well as position data for the electrodes and optionally dielectric data comprising values of dielectric properties for one or more portions of the modelled structure. Memory 804 is also configured to store values of the model parameters defining the structural properties of the structure and/or values of model parameters defining dielectric properties of the structure.

The system 800 may optionally further comprise a display 806 for displaying the outputted values of the model parameters (for example as outputted at block 360 of FIG. 3B). The system 800 may also optionally comprise an interface 808 for interfacing with an electric field generating/measuring system 810, such as a system described below with reference to FIG. 9. The electric field generating/measuring system 810 is optionally also part of system 800. The components of the system 800 are able to communicate with one another via a bus 801.

Figure 9:
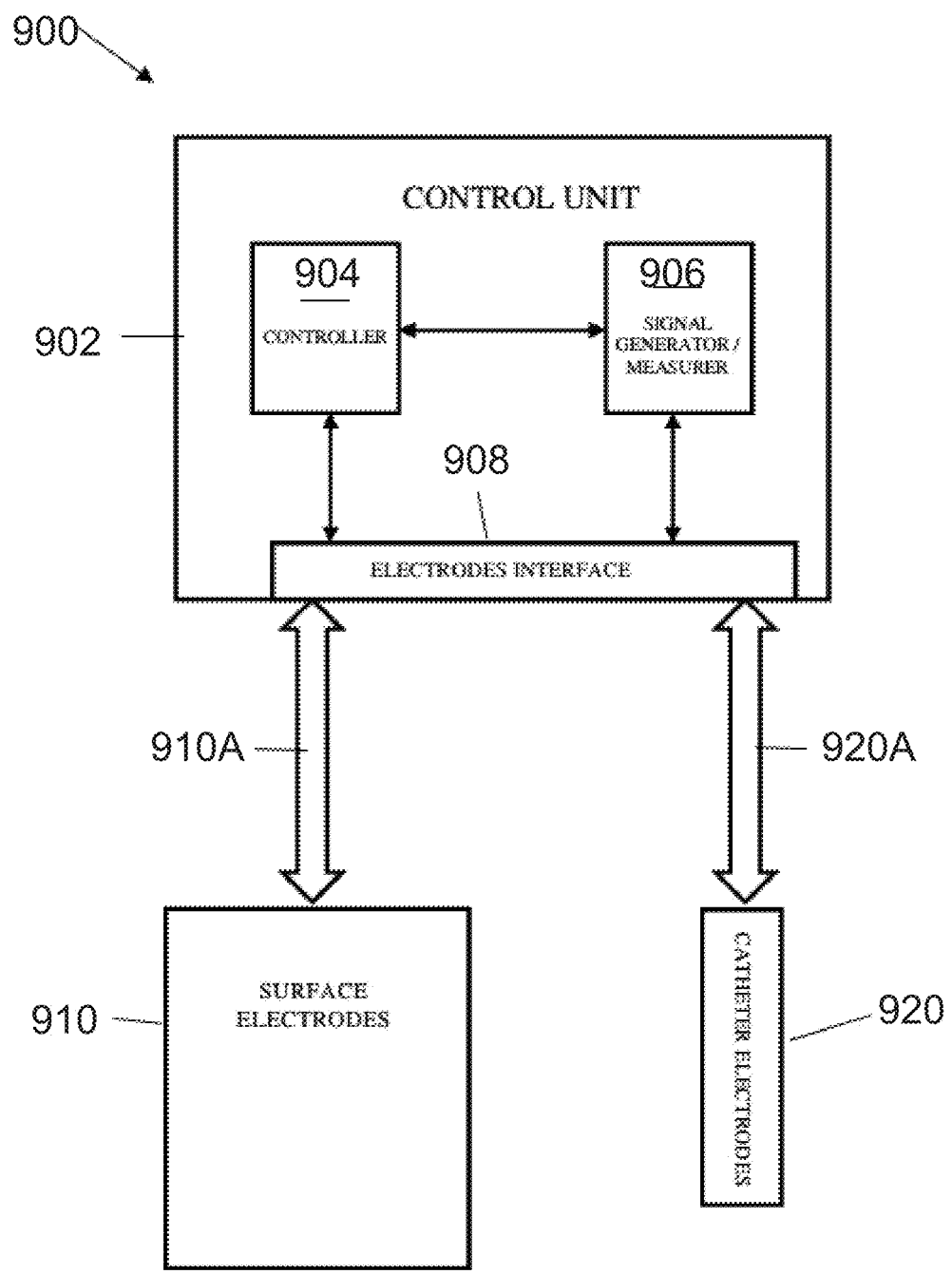
FIG. 9 is a schematic block diagram of a system configured to perform methods of the present disclosure.

FIG. 9 illustrates a schematic of an electric field generating/measuring system 900, such as electric field generating/measuring system depicted at 810 in FIG. 8. In some embodiments, the system 900 is part of system 810 and is configured to carry out some of the operations of the methods disclosed herein. For example, the system 900 may be used to carry out application of currents at the field-supplying electrodes and measuring voltages using the field-sensing electrodes disposed on one or more tools in or near the modelled structure.

The system 900 may comprise a main control unit 902 in active communication with a surface electrodes unit 910 (where present) and an intra-body electrodes unit 920 via communication channels 910A and 920A1 respectively. The main control unit 902 may comprise a processor 904 and a signal generator/measurer 906, such as the arrangement described below with reference to FIG. 10, connectable via an electrodes I/O interface unit 908. The control unit 902 may include a processor that may be, for example, a central processing unit processor (CPU), a chip or any suitable computing or computational device, equipped with an operating system, a memory, an executable code, and a storage (not shown in order to not obscure the drawing). The main control unit 902 may be configured to carry out methods described herein, and/or to execute or act as the various modules, units, etc. More than one computing device may be included in the system, and one or more computing devices may act as the various components of the system.

The signal generator/measurer 906 is configured to apply currents to surface electrodes 910 or intra-body electrodes 920 acting as field-supplying electrodes in accordance with an excitation scheme. The processor 904 may be configured to control the signal generator/measurer 906 to apply a certain current to one or more field-supplying electrodes defined by the excitation scheme. The current may be applied at a certain strength and at a certain frequency according to the excitation scheme. The signal generator is further configured to record voltage data for the voltages sensed by the electrodes acting as field-sensing electrodes, and the one or more field-sensing electrodes may be defined in accordance with the excitation scheme. The signal generator/measurer 906 may further be configured to cause two electrodes to transmit signals each at a different frequency, and receive (and measure) at this frequency, and at the frequency transmitted by the other electrode. In other words, a first signal may be transmitted by a first electrode, and a second signal transmitted by a second electrode. The first electrode may receive (and measure) the signal transmitted by the second electrode at the second frequency and the second electrode may receive and measure the signal transmitted by the first electrode at the first frequency. A voltage can be measured as the amplitude of each signal received at each electrode. In this manner, each electrode can act as a field-supplying electrode at a first frequency and a field-sensing electrode at a second frequency.

Data including the currents applied at the field-supplying electrodes and the voltages measured at the field-sensing electrodes can then be stored by the processor 904, or sent to a computing device such as the system 800 depicted in FIG. 8 for storing in memory 804. The data provided by the electric field generator/measurer 900 can then be used in the methods described with reference to FIGS. 3A, 3B, and 3C.

Figure 10:
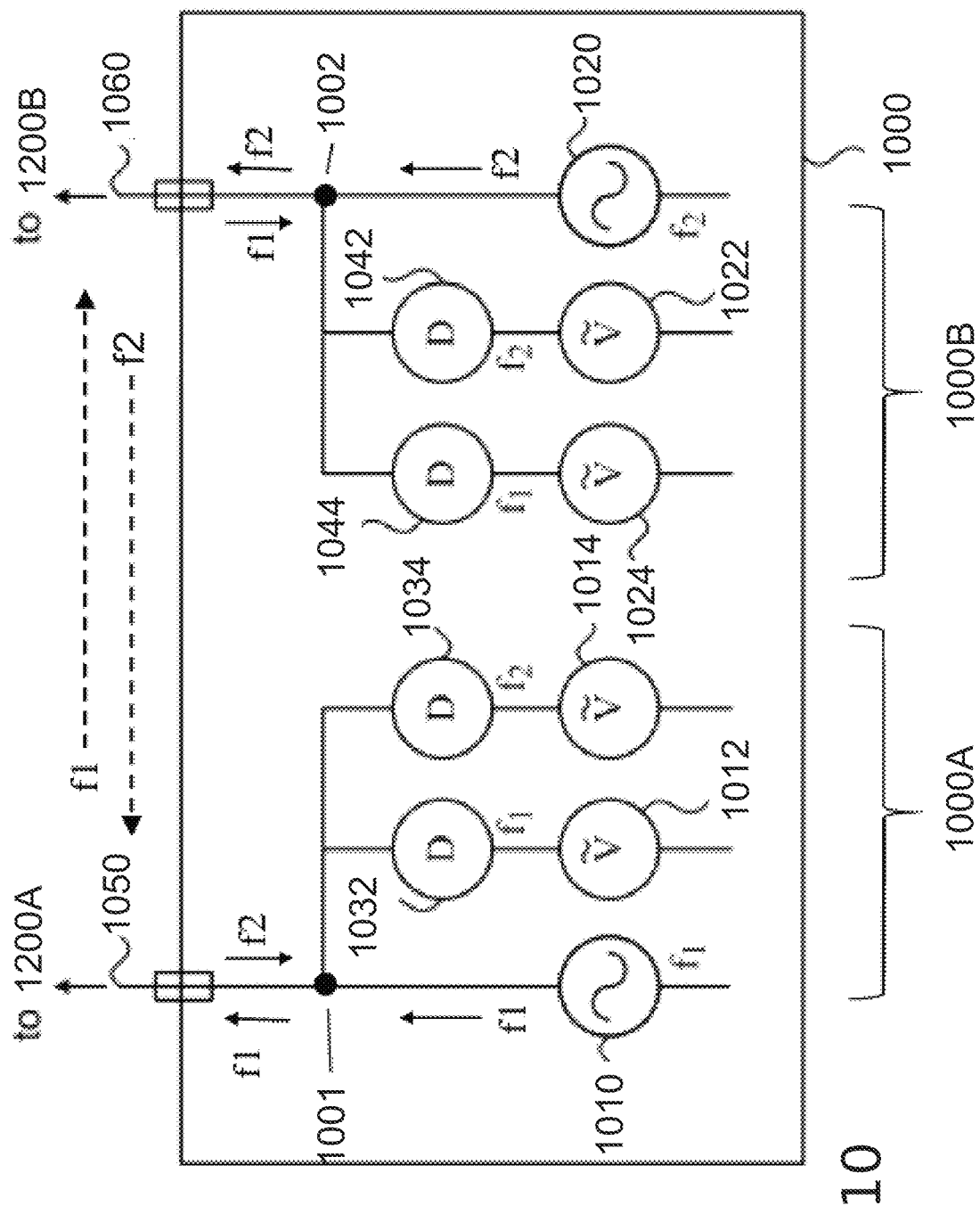
FIG. 10 illustrates a signal generator/measurer that enables two electrodes or two groups of one or more electrodes to be configured to transmit each at a different frequency, and receive (and measure) at both frequencies.

With reference to FIG. 10, a signal generator/measurer 1000 is depicted that enables two electrodes or two groups of one or more electrodes to be configured to transmit each at a different frequency, and receive (and measure) at both frequencies. Specifically, the signal measurer/generator is connected to the electrodes and is configured to measure and transmit voltages at different frequencies via the electrodes. In this sense, it can be considered that the electrodes are configured to transmit and/or sense voltages at different frequencies at the same time by means of the signal generator/measurer to which the electrodes are connected. In more detail, the signal generator/measurer comprises a signal source 1010 configured to provide a first frequency f1. This signal is fed to one or more electrodes 1200A, such as electrodes disposed on a catheter or on surface pads, via terminal point 1050. The signal at frequency f1 reaches another one or more electrodes 1200B and is received by it. Similarly, signal source 1020 provides signal in frequency f2. This signal is fed to one or more electrodes 1200B via terminal point 1060 and the signal reaches electrode 1200A and is received by it. As a result, junction points 1001 and 1002 experience a multiplexed signal comprised of frequencies f1 and f2. D is a demultiplexer that is configured to receive, in the current example, multiplexed signal (comprising signals in frequencies f1 and f2) and enable only signal in one of the frequencies to pass through—signal in frequency f1 passes via D 1032 and D 1044 and signal in frequency f2 passes via D 1034 and D 1042. Accordingly, voltmeter 1012 measures the amplitude of the signal in frequency f1, as originated from signal source 1010 and received by electrode 1200A, and voltmeter 1014 measures the amplitude of signal in frequency f2 as originated from signal source 1020 and received by electrode 1200A. The demultiplexing of the signals at section 1000B of electric field generator/measurer 1000 is done in the same manner. Namely, voltmeter 1024 measures the amplitude of the signal in frequency f1, as received by electrode 1200B, and voltmeter 1022 measures the amplitude of signal in frequency f2 as originated from signal source 1020 and received by electrode 1200B. It will be apparent that for exciting more electrodes the sections 1000A, 1000B of the electric field generator/measurer 1000 may be repeated. In some embodiments, other signal demultiplexers may be used, as is known in the art.

Figure 12:
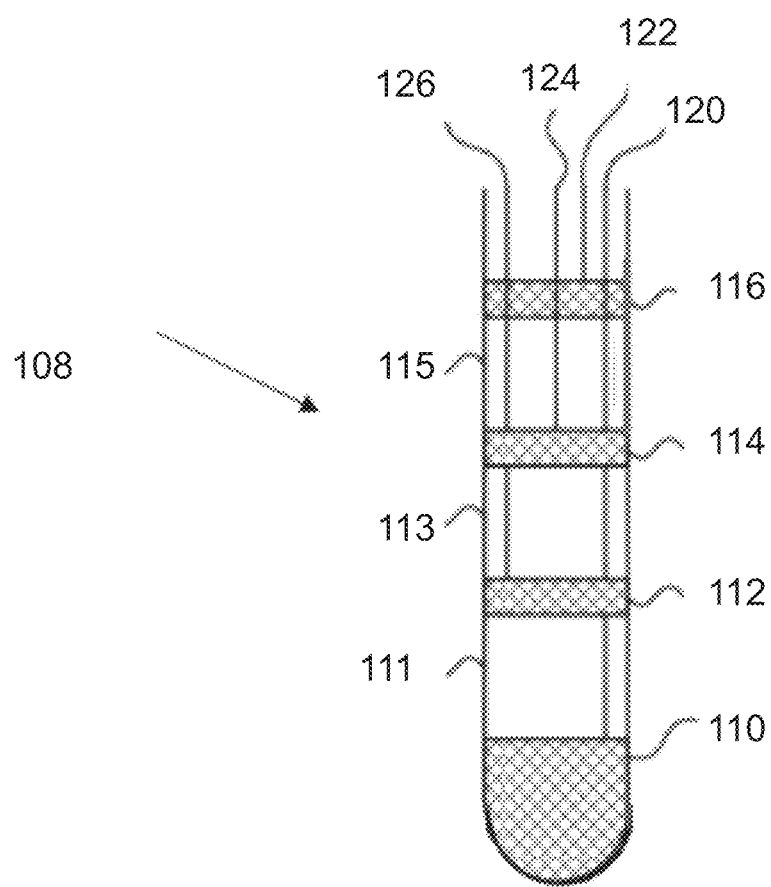
FIG. 12 is a schematic illustration of a catheter useful in some embodiments of the present disclosure.

Reference is now made to FIG. 12, which schematically illustrates a catheter 108 comprising one or more electrodes, useful according to some embodiments of the present disclosure. In the illustrated example the catheter 108 comprises four electrodes 110, 112, 114, 116. It will be understood that embodiments of the present disclosure may employ catheters comprising more or fewer than four electrodes. In accordance with some embodiments, the field-supplying and field-sensing electrodes used in the disclosed methods may be disposed on one or more catheters such as the catheter 108. Each of the electrodes may have a connection wire 120, 126, 124, 122, respectively, to enable connecting to electrical signal source and/or receiver unit, such as electric field generator/measurer. Each electrode may be configured to be connected to an electric field generator for applying currents to one or more field-supplying electrodes such that the electrodes supply an electric field, and each electrode may otherwise or also be connected to an electric field measurer for recording voltages sensed by one or more field-sensing electrodes in response to the electric field supplied by the field-supplying electrodes. Each electrode may therefore be configured to function as a field-supplying and a field-sensing electrode at the same time (optionally at different frequencies) or at different times (i.e. an electrode can function as a field-supplying electrode at a first time, and a field-sensing electrode at a second time different from the first). Electrodes 110, 112, 114, 116 may be disposed spaced from each other along the longitudinal axis of catheter 108 by longitudinal distances 111, 113, 115. The longitudinal distances may be, for example, in the range of lower than 1 millimeter or few millimeters and up to 1-2 cm or up to 4-6 cm between the farthest intra-body electrodes. In some embodiments, the electrodes may be arranged in pairs with the electrodes in each pair spaced about 2-3 cm apart, with about 8 mm between different pairs. The electrodes may have a length of 0.5-2.5 cm. In some embodiments, the electrodes may be annular in shape and may be disposed across the catheter with their outer surface substantially flush with the catheter. In some embodiments, these annular electrodes may be dimensioned and spaced as described above.

Figures 11A, 11B:
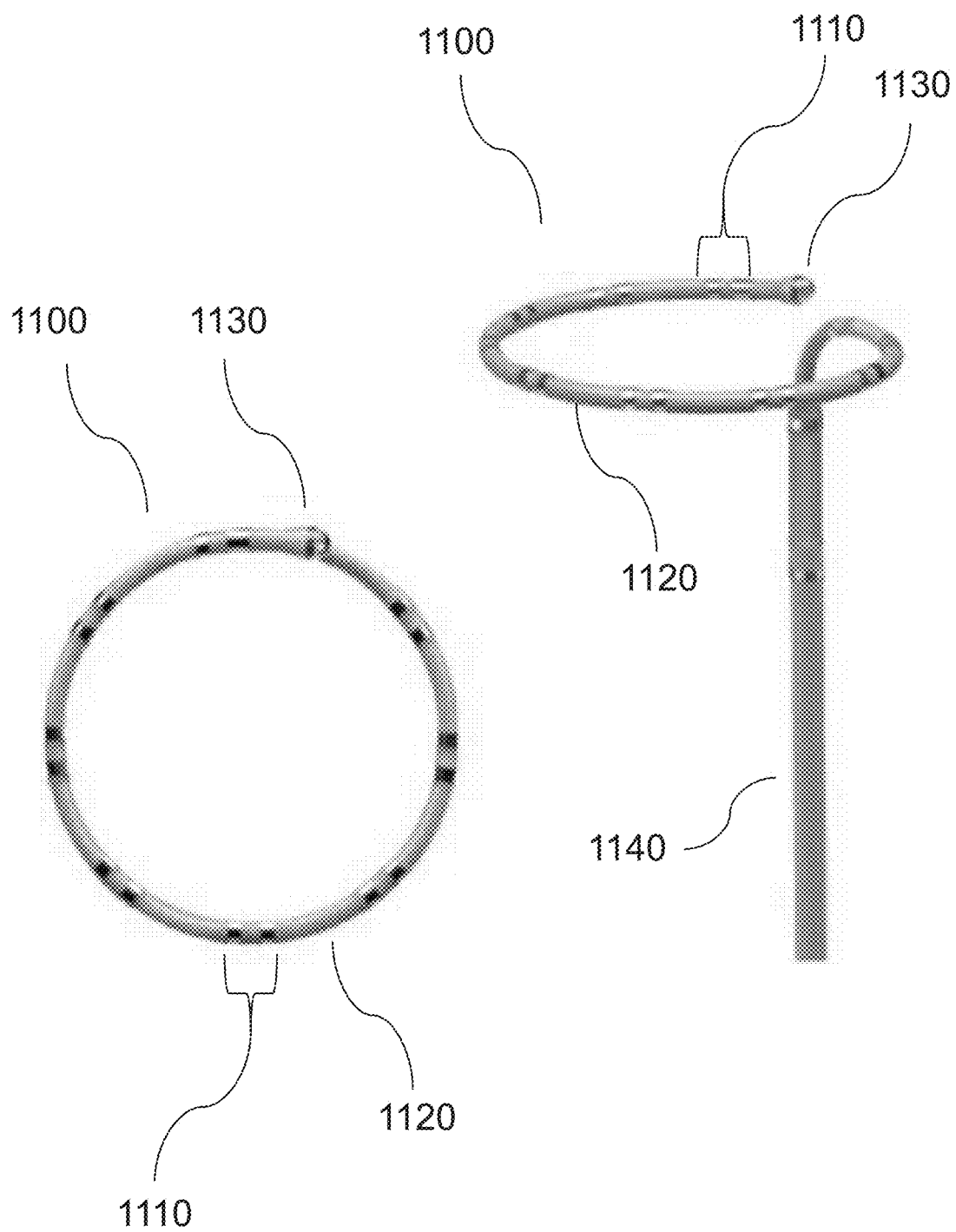
FIGS. 11A-11B schematically illustrate a Lasso® catheter from different views.

In some specific examples, the one or more tools disposed inside the body may comprise a loop catheter (e.g., a Lasso® catheter by Biosense Webster or an ORBITER PV Variable Loop Mapping catheter by Boston Scientific), for example as depicted in FIGS. 11A and 11B. FIG. 11A depicts a top-view of a Lasso® catheter whilst FIG. 11B depicts a side view of a Lasso® catheter. As can be seen from these drawings, the catheter 1100 comprises electrode pairs 1110 each comprising two electrodes, wherein the pairs are disposed on a loop portion 1120. The electrodes disposed on the loop portion may lie substantially flat in a plane defined by the loop. In other words, in some embodiments the loop portion 1120 is considered as a ring of electrodes that lie in a plane. This plane in which the electrodes lie and as defined by the loop is referred to herein as the lasso plane. It will be appreciated that other geometries that define a catheter plane can be used in place of the lasso catheter in these specific examples. A tip electrode 1130 is also provided which is disposed at the end of the loop portion as illustrated. In the example depicted in FIG. 11A, the catheter comprises 8 pairs of electrodes and a tip electrode, and in the example depicted of FIG. 11B, the catheter comprises 10 pairs of electrodes and a tip electrode. In other examples (not depicted), the catheter may comprise 5 pairs of electrodes (i.e. 10 electrodes and a tip electrode), or any number of pairs up to 10 pairs plus a tip electrode. In examples, the diameter of the loop may be between 10 and 40 mm, and more specifically may be 12 mm, 15 mm, 20 mm, 25 mm, or 35 mm. In examples, the spacing between each pair 1110 of electrodes is between 4 mm and 11 mm, and more specifically may be 4 mm, 4.5 mm, 6 mm, 8 mm or 11 mm. The catheter may comprise a stem portion 1140 to which an end of the loop portion (the opposite end to which the tip electrode is disposed) is attached.

Knowledge of the relative distances between electrodes may be used as part of the methods of the present disclosure. These relative distances may be derived from the position data, indicative of the positions of the electrodes at the time the voltages were measured. Specifically, as would be appreciated by the skilled person, the distance between a field-sensing electrode and a field-supplying electrode can be used to determine the expected electric field at the field-sensing electrode as a result of a current applied at the field-supplying electrode. Specifically, the skilled person would understand how to apply the laws of electromagnetics to determine the expected electric field at a given location (the field-sensing electrode) relative to an electric field source (the field-supplying electrode), based on a current applied to the field-supplying electrode. Moreover, the skilled person would understand how to apply the spatial distribution of dielectric properties of the material(s), defined by the model parameters, in between and surrounding the field-supplying and field-sensing electrodes in order to determine the expected electric field at the field-sensing electrode location as a result of the currents applied to the field-supplying electrodes.

Schemes of electrical excitations of field-supplying surface or intra-body electrodes (also referred herein as excitation scheme or scheme of excitation) yield voltages measurable on one or more field sensing surface or intra-body field-sensing electrodes. The voltage readings (voltages sensed by the field-sensing electrodes) may be used to reconstruct a spatial distribution of the electrical conductivity or other dielectric property of tissues/materials through which the electrical signals pass. Schemes of excitation may comprise one or more of: selection of the field-supplying electrode(s) and field-sensing electrodes, selection of the frequency of the transmitted signals, selection of the amplitude of each of the transmitted signals, selected duration of the transmission, selection phase differences (or de-phasing) between signals transmitted concurrently from two or more field-supplying electrodes at a same frequency, and the like. A particular excitation scheme may involve a plurality of electrodes each supplying an electric field at a respective frequency at the same time. Considering the specific example of the electrode arrangement on the catheter in FIG.

12, excitation schemes may be used to invoke transmission from, for example, at least one electrode (110) acting as a field-supplying electrode and the resulting voltages developing on at least the remaining electrodes (112, 114, 116) may be recorded, thereby providing an indication of the conductivity of the material surrounding the catheter along three respective signal paths. In this specific example, a ground electrode may be positioned on the surface of the body to function as a field sink for the generated electric fields. Alternatively one of the electrodes on the probe (112, 114, 116), other than the field-supplying electrode, may function as the ground electrode. Each of the electrodes may have different roles for different frequencies. For example, each electrode (110, 112, 114, 116) may simultaneously function as a field-supplying electrode at a different frequency, and each electrode may function as a field-sensing electrode for the frequencies other than the frequency that electrode is transmitting at. In other words, four different frequencies may be transmitted and sensed at the same time using the four electrodes in this specific example. In other words, each of the electrodes supplying a field at a respective frequency may simultaneously function as a field-sensing electrode that senses voltages resulting from the electric fields supplied by the remaining electrodes at the other respective frequencies. In some examples, each electrode transmitting at a given frequency may also simultaneously act as a field-sensing electrode for that same frequency. In other words, an electrode transmitting at a frequency can also be used to measure a voltage at the same transmitted frequency.

It would therefore be appreciated that reference to field-supplying electrodes and field-sensing electrodes refers to the function of an electrode. Thus a reference to a field-supplying electrode and a field-sensing electrode may actually refer to the same electrode which is functioning as a field-supplying electrode at one frequency and is simultaneously also functioning as a field-sensing electrode at other frequencies, and optionally at the same frequency. Furthermore, reference to a field-supplying electrode and a field-sensing electrode may actually refer to the same electrode which is functioning as a field-supplying electrode at one point in time and is functioning as a field-sensing electrode at another point in time, optionally at the same or at a different frequency. It will be appreciated that excitation schemes may vary in terms of the placement and identity of electrodes used. In some embodiments, both surface and intra-body electrodes are used. In some embodiments, the intra-body electrodes are disposed on a moveable catheter or tool, which is moved from one position to the next to acquire respective sets of data.

Transmitted signals may be transmitted from one or more of the field-supplying electrodes, and voltages developing on one or more of the field-sensing electrodes during the excitation may be received and recorded for further processing, e.g., for determining model parameters. The further processing may occur on-line, i.e. in real time as the voltages are recorded, or may occur off-line, i.e. at a later time (not in real time, e.g., when the electrodes are no longer in the body). The voltages may be indicative of the conductivity or other dielectric property of the material (e.g. body tissue or surgical implement that is a separate implement to a tool or tools carrying the electrodes) through which the electrical signals have passed. Since the conductivity along any electrical path of a signal is indicative of the nature of the material along that path, the more different signal paths are sampled (i.e. between different combinations of field-supplying and field-sensing electrodes), the richer the data is regarding the nature of the material through which the different electrical signals have passed. In other words, sampling a number of signal paths between different ones of the field-supplying and field-sensing electrodes at different locations results in voltage data indicative of the spatial distribution of the conductivity (or other dielectric property) of the material through which the electrical signals travel. If the values of conductivity of the material is already known, it is possible to use these values to fix the values of corresponding model parameters that represent dielectric properties of the structure, which can be used as a constraint to obtain information on the spatial distribution of the known dielectric property of the material through which the electrical signals have travelled and thus build a physical picture of the material, by comparing the measured voltages to modelled voltages, wherein the model voltages are calculated based on the structural and dielectric parameters, including those that are fixed. Otherwise, if the values of conductivity of the material are not known, it is possible to determine the values of the parameters representing dielectric properties of the structure together with solving for the other model parameters to obtain information on the spatial distribution of the dielectric property of the material through which the electrical signals have travelled. Specifically, solving for the parameters of the model involves adjusting the values of those parameters in order to reduce a difference between measured voltages and modelled voltages, wherein the modelled voltages are voltages predicted to be measured based on the model or the structure (based on the values of the parameters). In some embodiments, values of one or more of the parameters, such as dielectric properties or dimensions of the structure are not known, but are expected to be within a known range. The calculations can be constrained to find values of the parameters within these ranges that minimize the difference between calculated and measured voltages. In other words, the optimization process may have constraints imposed on it such that the values of these parameters are found within the respective predefined range.

While reference is made herein to a 'known' conductivity, impedance, or other dielectric property of the structure, it would be appreciated that the 'known' values may not reflect the exact value of the dielectric property of the structure, but may be a value that has been otherwise predetermined, for example as an estimation or approximation, or an assumption of the real value. The 'known' values of the dielectric properties of the structure that may be used to fix the values of corresponding model parameters therefore refer to predefined values that are not necessarily the exact real values for the structure but may instead be assumed values based on an estimation or knowledge of the material of the structure. Furthermore, instead of accessing 'known' predefined dielectric data for the structure, the values of the dielectric properties of the structure may be model parameters to be solved using the disclosed methods in addition or as an alternative to the structural properties of the structure. It would be appreciated that solving for the values of the dielectric properties involves analogous operations to those discussed in relation to solving for the values of the structural properties of the structure.

The paths along which transmitted signals pass are not known, as the signals do not travel in straight lines, but mainly along paths of minimal resistivity. However, obtaining a number of voltage measurements using different field-sensing electrodes as a result of electric fields supplied by different field-supplying electrodes provides data indicative of the spatial distribution of dielectric properties of the material in the region of the electrodes. Thus for a structure in the region of the electrodes, it is possible to determine values of model parameters characterizing the structural properties and/or the dielectric properties of the whole structure, or of portions of the structure using voltages calculated based on the known currents supplied and starting values for the parameters. The parameter values can then be iteratively updated by comparing the calculated voltages with the measured voltages in order to increase the accuracy of the parameter values to more closely resemble the corresponding real structural and dielectric properties of the structure.

The methods referred to herein generally refer to computing model parameters of a model of a structure, the parameters defining structural properties and dielectric properties of a structure in a body. In other words, the methods refer to determining the structural and dielectric properties of a structure given the positions of field sources (resulting from injected currents) and the positions of field (voltage) measurements. An approach to determining the structural and dielectric properties of the structure involves a form of optimization to find parameters for the model that give rise to calculated voltages consistent with measured voltages. For example, a model of the structure may be initialized with parameter starting values that may be based on a starting guess and then optimized to be consistent with measured voltage data.

General As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the present disclosure may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments may be presented with reference to a range format. It should be understood that the description in range format is merely for convenience and brevity and should not be construed as an inflexible limitation on the scope of descriptions of the present disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although descriptions of the present disclosure are provided in conjunction with specific embodiments, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

It is appreciated that certain features which are, for clarity, described in the present disclosure in the context of separate embodiments, may also be provided in combination in a single embodiment. Conversely, various features, which are, for brevity, described in the context of a single embodiment, may also be provided separately or in any suitable subcombination or as suitable in any other described embodiment of the present disclosure. Particular features described in the context of various embodiments are not to be considered essential features of those embodiments, unless the embodiment is inoperative without those elements.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of computing the shape of a structure within a human or animal body for real-time use in a medical procedure, the method comprising:
accessing a model which models the structure as a spatially related collection of structural and dielectric properties, at least one of the properties being specified as at least one corresponding parameter;
accessing location-associated voltage measurements made in the vicinity of the structure by one or more in-body field sensing electrodes:
including a plurality of measurements for each sensing electrode at a corresponding plurality of associated locations, and
wherein the measurements are responsive to currents applied to one or more field-supplying electrodes; and
computing parameter values for the at least one parameter by adjusting the parameter values to fit predicted voltage values at model-defined locations to the accessed voltage measurements at their associated locations, wherein the predicted voltage values are predicted from the model for the currents applied to the field supplying electrodes; and
provide the model with its parameter values for use in display, thereby providing an indication of the structural environment within which the location-associated voltage measurements were obtained.

2. The method of claim 1, wherein the model comprises at least two parameters: one contributing only to the modeling of a first portion of the structure, and another contributing to the modeling of the first portion as well as an additional portion of the structure.

3. The method of claim 1, wherein the model comprises at least three parameters: a first and a second parameter, each respectively contributing only to the modeling of first and second portions of the structure, respectively, and a third parameter, which contributes to the modeling of both the first and second portions.

4. The method of claim 1, wherein the model comprises a first parameter which is associated to an error cost for some of its values; and wherein the adjusting takes the error cost into account.

5. The method of claim 1, wherein the model comprises a first parameter and a second parameter, and a computable relationship between the first and second parameters is associated to an error cost for some of its values; and wherein the adjusting takes the error cost into account.

6. The method of claim 1, wherein parameters of the model define parameterized geometrical shapes assigned to a respective plurality of portions of the model, and the adjusting adjusts the geometrical shapes to approximate the positions of surfaces of the structure.

7. The method of claim 1, wherein the number of accessed voltage measurements used in the computing exceeds the number of parameters by a factor of at least three.

8. The method of claim 1, wherein the number of parameters is below 100, and above 6.

9. The method of claim 1, comprising iteratively:
accessing of the location-associated voltage measurements while new location-associated voltage measurements are being obtained;
re-computing the parameter values using the new location-associated voltage measurements; and
providing new versions of the model with its parameter values for use in display.

10. The method of claim 9, wherein the new location-associated voltage measurements are obtained from locations of the structure represented in a previous display of the model, but not among locations for which location-associated voltage measurements were previously available.

11. The method of claim 10, wherein the represented locations of the structure were, in the previous display of the model, at least 1 cm away from the closest locations for which location-associated voltage measurements were previously available.

12. The method of claim 1, wherein the at least one parameter comprises one or more model parameters defining dielectric properties of the structure.

13. The method of claim 12, wherein the at least one parameter comprises two or more parameters defining dielectric properties of respective different portions of the structure.

14. The method of claim 12, wherein the dielectric properties comprise dielectric properties corresponding to the tissue of one or more of:
heart cardiac muscle,
vascular wall,
heart valve annulus, and
heart valve leaflet.

15. A method according to claim 1, wherein the one or more field supplying electrodes comprise a plurality field supplying electrodes, wherein the current applied to each field supplying electrode was at a different respective frequency such that each field supplying electrode supplied an electric field at the frequency of the respective applied current.

16. A method according to claim 15, wherein, when the voltages were measured, each of the one or more field sensing electrodes sensed voltages in response to each of the electric fields supplied at the different frequencies.

17. A method according to claim 1, wherein the one or more field sensing electrodes were disposed on one or more tools positioned inside the body at the time that the accessed voltage measurements were measured, and configured to move within the body.

18. A method according to claim 1, wherein the accessed voltage measurements comprise voltage measurements recorded at different times using the same one or more field sensing electrodes.

19. A method according to claim 18 wherein at each of the different times at which voltage measurements were recorded, the one or more field sensing electrodes are disposed at different positions in the body.

20. A method according to claim 1, wherein, when the accessed voltage measurements were measured, voltage measurements were sampled at a sampling rate of between 300 kHz and 500 kHz.

21. A method according to claim 20, further comprising performing signal processing on the voltage measurements and updating the voltage measurements at a rate of at least 100 times a second.

22. A method according to claim 1, wherein, when the accessed voltage measurements were measured, applied current measurements indicative of the currents applied to the one or more field supplying electrodes were sampled at a sampling rate of between 300 kHz and 500 kHz.

23. A method according to claim 22, further comprising performing signal processing on the current measurements and updating the applied current data at a rate of at least 100 times a second.

24. A method according to claim 1, wherein the structure is a surgical implement.

25. A method according to claim 1, wherein the structure comprises an internal tissue surface.

26. A method according to claim 25, wherein structure is a wall of a body cavity, and wherein the tissue surface is an internal surface of the wall.

27. A method according to claim 26, wherein the structure is a leaflet in a heart cavity and wherein the tissue surface is a surface of the leaflet.

28. A method according to claim 1 wherein when the accessed voltage measurements were measured, the one or more field supplying electrodes and one or more field sensing electrodes were disposed within a cavity of a heart and on a tool and in a plane; and wherein the at least one parameter comprises a parameter representing a distance between the tool and the internal tissue surface, and a parameter representing an angle between the plane of the electrodes and the internal tissue surface.

29. A method according to claim 28, wherein the at least one parameter comprises a parameter representing a distance between the tool and the internal tissue surface, and a parameter representing an angle between the plane of the electrodes and the internal tissue surface, and wherein the internal tissue surface is modelled as a plurality of planar surfaces, each surface having a respective model parameter representing a distance between the tool and the surface, and a respective model parameter representing an angle between the tool and the surface.

30. A method according to claim 26, wherein the at least one parameter comprises a parameter representing a dielectric property of a material on the side of the wall outside of the body cavity.

31. A method according to claim 1 wherein computing the parameter values is performed in real-time as the accessed voltage measurements are measured.

32. A system for determining the values of one or more model parameters associated with a model of an object in a region of an organ of a human or animal body, the system comprising:
 a processor configured to implement a method according to claim 1; and
 a memory for storing the voltage measurements, the position data, the current data, and the values of the one or more model parameters.

33. A system according to claim 32, further comprising:
 a plurality of electrodes disposed on one or more tools;
 an electric field generator configured to apply currents to the electrodes, and
 an electric field receiver configured to receive voltages measured at the electrodes.

34. A non-transitory computer readable medium carrying instructions that, when executed by one or more processors, cause the processors to carry out a method according to claim 1.

* * * * *